(12) United States Patent
Tatsuta et al.

(10) Patent No.: US 7,996,177 B2
(45) Date of Patent: Aug. 9, 2011

(54) INFORMATION DISPLAY SYSTEM

(75) Inventors: Seiji Tatsuta, Hachioji (JP); Ryohei Sugihara, Machida (JP); Yoichi Iba, Hachioji (JP)

(73) Assignee: Olympus Corporation, Tokyo (JP)

( * ) Notice: Subject to any disclaimer, the term of this patent is extended or adjusted under 35 U.S.C. 154(b) by 1260 days.

(21) Appl. No.: 11/396,217

(22) Filed: Mar. 31, 2006

(65) Prior Publication Data
US 2006/0230108 A1 Oct. 12, 2006

(30) Foreign Application Priority Data

Apr. 7, 2005 (JP) .................................. 2005-111044

(51) Int. Cl.
G01C 17/00 (2006.01)

(52) U.S. Cl. ....................................................... 702/150

(58) Field of Classification Search .................. 702/150, 702/155, 158–160, 179, 181; 345/2.1–2.3; 701/201–202, 207–211
See application file for complete search history.

(56) References Cited

U.S. PATENT DOCUMENTS

| | | | |
|---|---|---|---|
| 6,336,072 B1 | 1/2002 | Takayama et al. | |
| 6,607,484 B2 | 8/2003 | Suzuki et al. | |
| 6,697,731 B2 | 2/2004 | Takayama et al. | |
| 6,748,316 B2 | 6/2004 | Takayama et al. | |
| 6,925,603 B1 | 8/2005 | Naito et al. | |
| 6,942,615 B2 | 9/2005 | Suzuki et al. | |
| 7,596,450 B2 * | 9/2009 | Hong ............................. | 701/209 |
| 2001/0049471 A1 | 12/2001 | Suzuki et al. | |
| 2001/0056443 A1 | 12/2001 | Takayama et al. | |
| 2002/0099499 A1 | 7/2002 | Takayama et al. | |
| 2002/0103597 A1 | 8/2002 | Takayama et al. | |
| 2003/0194205 A1 | 10/2003 | Suzuki et al. | |
| 2003/0195398 A1 | 10/2003 | Suzuki et al. | |
| 2003/0204132 A1 | 10/2003 | Suzuki et al. | |
| 2005/0020279 A1 * | 1/2005 | Markhovsky et al. ...... | 455/456.1 |
| 2007/0135225 A1 * | 6/2007 | Nieminen et al. ............ | 473/212 |
| 2008/0190202 A1 * | 8/2008 | Kulach et al. ............. | 73/514.01 |

FOREIGN PATENT DOCUMENTS

| | | |
|---|---|---|
| JP | 2000-215211 | 8/2000 |
| JP | 2001-092878 A | 4/2001 |
| JP | 2001-092978 A | 4/2001 |
| JP | 2001-344352 A | 12/2001 |
| JP | 2002-034073 A | 1/2002 |

(Continued)

OTHER PUBLICATIONS

Japanese Office Action dated Aug. 2, 2010 (and English translation thereof) in counterpart Japanese Application No. 2005-111044.

(Continued)

*Primary Examiner* — Aditya Bhat

(74) *Attorney, Agent, or Firm* — Holtz, Holtz, Goodman & Chick, PC

(57) ABSTRACT

An information display system includes a sensor which measures a state of each part of a body of a user, an active state identifying section which identifies an active state of the user based on a measurement result, an information estimating section which estimates information required by the user based on the active state identified by the active state identifying section, a database which stores at least the information required by the user, an information selecting section which selects the information required by the user from a plurality of information stored in the database, and an information display section which displays the information required by the user selected by the information selecting section.

33 Claims, 61 Drawing Sheets

FOREIGN PATENT DOCUMENTS

| | | |
|---|---|---|
| JP | 2003-050867 A | 2/2003 |
| JP | 2003-167900 A | 6/2003 |
| JP | 2003-303265 A | 10/2003 |
| JP | 2005-050050 A | 2/2005 |

OTHER PUBLICATIONS

Japanese Office Action (Decision of Refusal) dated Oct. 27, 2010 (and English translation thereof) in counterpart Japanese Application No. 2005-111044.

"Design and Implementation of a Context-Aware Content Delivery Service Using Tiny Mobile Sensors": Tomoaki Hayashi: Technical research report at a congress of the Society of Information and Communication; Society of Information and Communication, Japan; (Feb. 24, 2005); vol. 104; No. 691; pp. 149-154.

"A Context-Aware Content Delivery Service Using Off-the-shelf Sensors": Yoshihiro Kawahara et al.; In Proceedings of The Second International Conference on Mobile Systems, Applications, and Services; Boston, USA: (Jun. 2004).

* cited by examiner

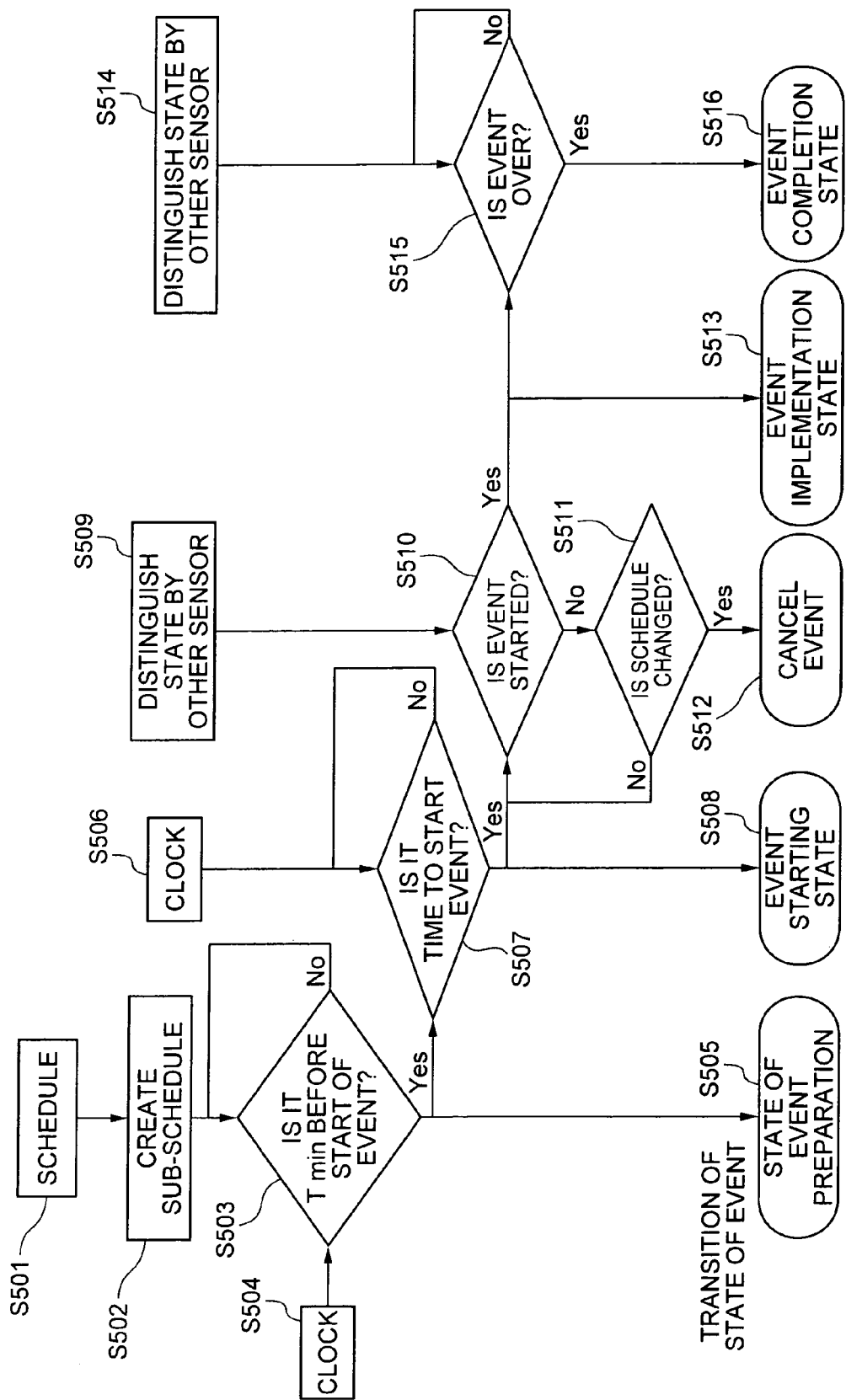

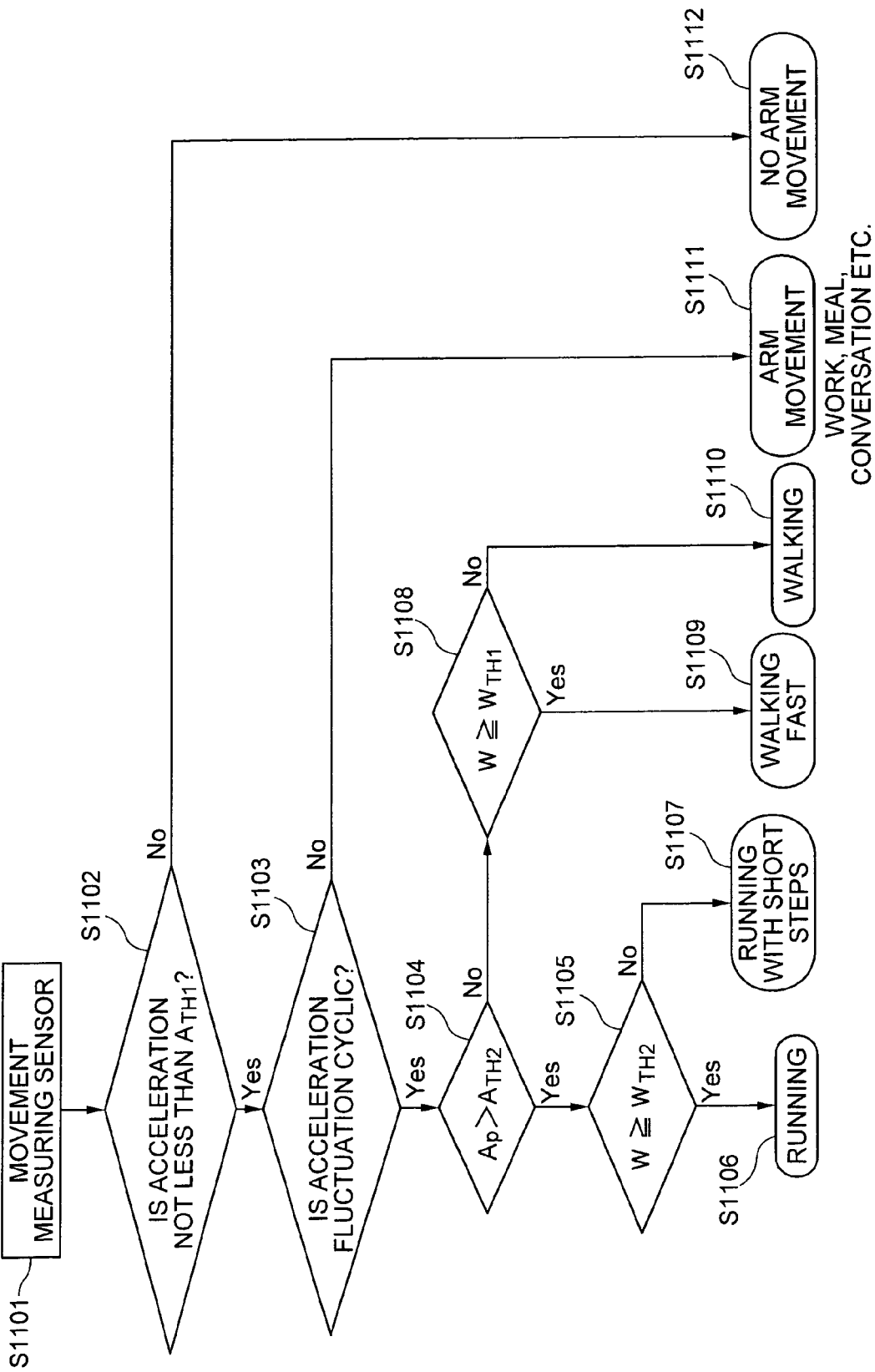

FIG. 15

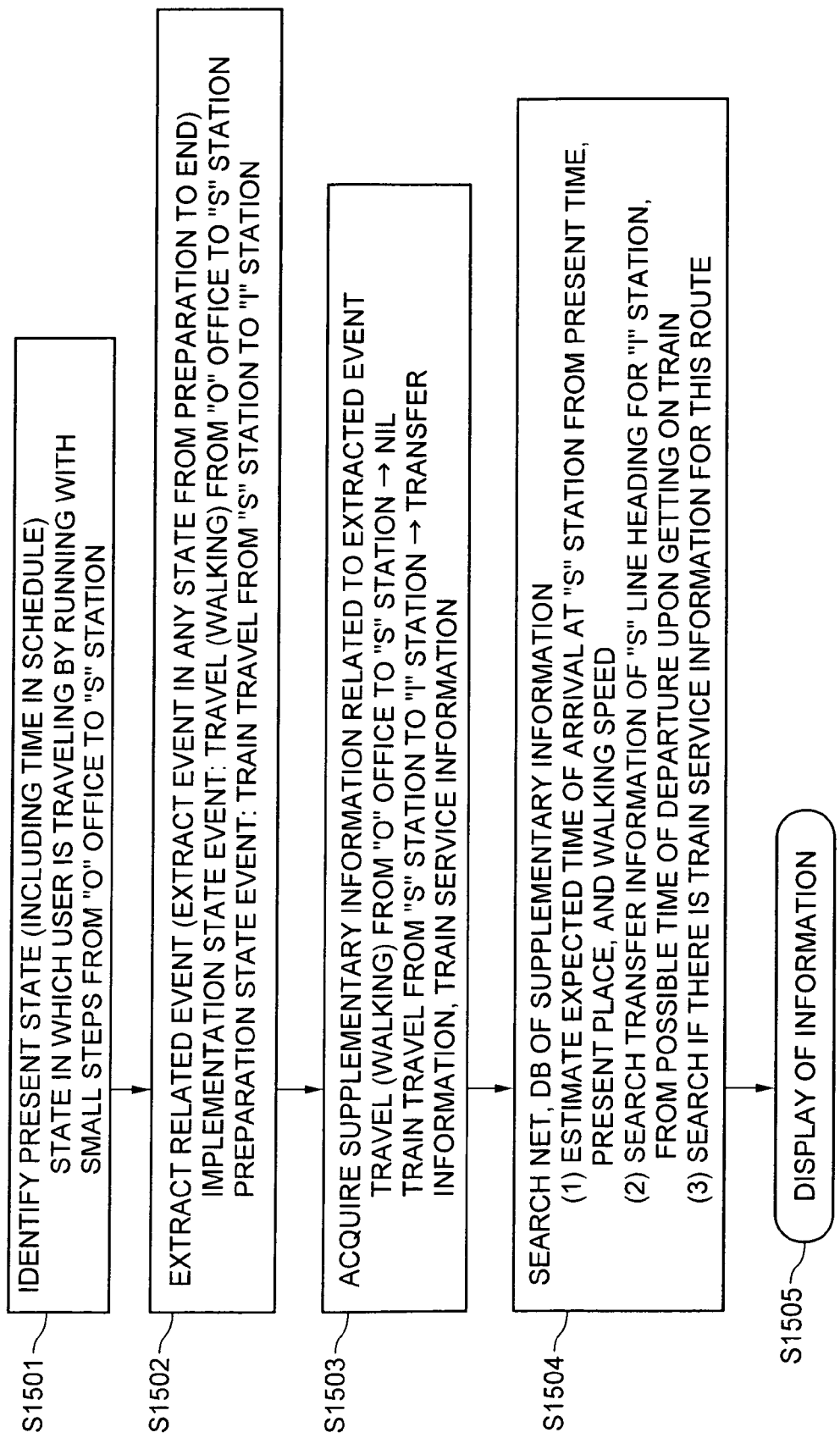

S1501 — IDENTIFY PRESENT STATE (INCLUDING TIME IN SCHEDULE) STATE IN WHICH USER IS TRAVELING BY RUNNING WITH SMALL STEPS FROM "O" OFFICE TO "S" STATION

S1502 — EXTRACT RELATED EVENT (EXTRACT EVENT IN ANY STATE FROM PREPARATION TO END) IMPLEMENTATION STATE EVENT: TRAVEL (WALKING) FROM "O" OFFICE TO "S" STATION PREPARATION STATE EVENT: TRAIN TRAVEL FROM "S" STATION TO "I" STATION

S1503 — ACQUIRE SUPPLEMENTARY INFORMATION RELATED TO EXTRACTED EVENT TRAVEL (WALKING) FROM "O" OFFICE TO "S" STATION → NIL TRAIN TRAVEL FROM "S" STATION TO "I" STATION → TRANSFER INFORMATION, TRAIN SERVICE INFORMATION

S1504 — SEARCH NET, DB OF SUPPLEMENTARY INFORMATION
(1) ESTIMATE EXPECTED TIME OF ARRIVAL AT "S" STATION FROM PRESENT TIME, PRESENT PLACE, AND WALKING SPEED
(2) SEARCH TRANSFER INFORMATION OF "S" LINE HEADING FOR "I" STATION, FROM POSSIBLE TIME OF DEPARTURE UPON GETTING ON TRAIN
(3) SEARCH IF THERE IS TRAIN SERVICE INFORMATION FOR THIS ROUTE

S1505 — DISPLAY OF INFORMATION

FIG. 18A

| EVENT | PREPARATION STATE | STARTING STATE |
|---|---|---|
| WAKE-UP | | ALARM CLOCK (ALARM) |
| TRAVEL BY TRAIN (BUS) | STATION OF GETTING ON/GETTING OFF TRAIN, TIME OF DEPARTURE/ARRIVAL, TIME REQUIRED, FARE, SERVICE CONDITION, PLATFORM (TERMINAL) | NOT IN PARTICULAR |
| TRAVEL BY WALKING | PLACE OF DEPARTURE/ARRIVAL, DEPARTURE/ARRIVAL TIME, TIME REQUIRED, ROUTE INFORMATION | NOTIFICATION OF DEPARTURE TIME (ALARM) |
| CONFERENCE, MEETING | NOTIFICATION OF PREPARATION TIME (ALARM), ITEMS SET BEFOREHAND BY USER SUCH AS MATERIAL AND OTHER PREPARATION ETC. | NOTIFICATION OF SHIFT TO WORK MODE (ALARM) |
| WORK | SCHEDULE AND TASK HEREAFTER | NOTIFICATION OF SHIFT TO WORK MODE (ALARM) |
| BREAK DURING WORK | NOT IN PARTICULAR | NOT IN PARTICULAR |
| MEAL | ADVICE REGARDING MEAL ACCORDING TO HEALTH CONDITION, DIETARY RESTRICTIONS, HISTORY AND PREFERENCE, INFORMATION ABOUT NEARBY EATING PLACES WHILE BEING OUTSIDE | RECOMMENDED MENU |
| TRAVEL INSIDE FACILITY (STATION, HOTEL, THEME PARK ETC.) | INFORMATION ABOUT HP (TENANTS, ENTERTAINMENT ETC.) AND NEAREST ENTRANCE FROM PRESENT PLACE, INFORMATION ABOUT FACILITY | NOT IN PARTICULAR |
| WATCHING MOVIE ETC. | INFORMATION SET BY USER | NOTIFICATION OF SHIFT TO SLEEP MODE (ALARM) |
| JOGGING | MOTIVATION STIMULATING INFORMATION | NOTIFICATION OF STARTING TIME (ALARM) |
| GO TO BED | NEXT DAY'S SCHEDULE, WEATHER, AND SCHEDULED WAKE-UP TIME | NOTIFICATION OF TIME FOR GOING TO BED (TO PREVENT SITTING UP TILL LATE) |

FIG. 18B

| EVENT | IMPLEMENTATION STATE | COMPLETION STATE | NOTE |
|---|---|---|---|
| WAKE-UP | TIME, WEATHER FORECAST, EXTERNAL CONDITION, (WEATHER), HEALTH CONDITION, THAT DAY'S SCHEDULE | NOT IN PARTICULAR | IMPLEMENTATION STATE IS STATE FROM STOPPING ALARM CLOCK TILL STARTING ACTIVITIES (OR LEAVING BED ROOM) |
| TRAVEL BY TRAIN (BUS) | INFORMATION SET BY USER SUCH AS STATION OF GETTING OFF TRAIN, TIME OF ARRIVAL, MAIL, AND NEWS | NOTIFICATION OF GETTING OFF (ALARM) | STATE FROM GETTING ON TO GETTING OFF TRAIN IS IMPLEMENTATION STATE |
| TRAVEL BY WALKING | ROUTE INFORMATION, SCHEDULED TIME OF ARRIVAL, DIFFERENCE FROM EXPECTED TIME OF ARRIVAL | NOT IN PARTICULAR | ROUTE INFORMATION IS NOT DISPLAYED FOR PLACES WHICH ARE FREQUENTED SUCH AS HOME AND OFFICE |
| CONFERENCE, MEETING | ITEMS SET BEFOREHAND BY USER SUCH AS MATERIAL (EMOTIONAL CONTROL INFORMATION) | SCHEDULE HEREAFTER | EMOTIONAL INFORMATION IS INFORMATION FOR COOLING DOWN TEMPER UPON GETTING EXTREMELY TENSED OR ANGRY |
| WORK | WORK MODE (DISPLAY OF ANY INFORMATION NOT RELATED TO WORK EXCEPT EMERGENCY INFORMATION IS PROHIBITED) | RECOVERY FROM WORK MODE | |
| BREAK DURING WORK | INFORMATION FOR DIVERTING MIND SET BEFOREHAND BY USER | NOTIFICATION TO EVOKE COMPLETION (ALARM TO PREVENT EXCESSIVE BREAK) | |
| MEAL | INFORMATION SET BY USER SUCH AS MAIL AND NEWS | SCHEDULE HEREAFTER | |
| TRAVEL INSIDE FACILITY (STATION, HOTEL, THEME PARK ETC.) | INFORMATION ABOUT INSIDE OF FACILITY (TENANTS, ELEVATOR, ESCALATOR, TOILET ETC.) | NOT IN PARTICULAR | TENANT INFORMATION ETC. DISPLAYED BASED ON ACTION HISTORY AND PREFERENCE OF INDIVIDUAL |
| WATCHING MOVIE ETC. | SLEEP MODE (DISPLAY OF INFORMATION OTHER THAN EMERGENCY INFORMATION IS PROHIBITED) | RECOVERY FROM SLEEP MODE | CHANGED TO STARTING STATE FOR ENTERING SHOP WHILE BEING OUT |
| JOGGING | PACE, EXERCISE LOAD, MOTIVATION MAINTENANCE INFORMATION | NOTIFICATION TO EVOKE COMPLETION (ALARM TO PREVENT EXCESSIVE EXERCIESE), DISPLAY OF EFFORT EFFECT, COMPENSATION | |
| GO TO BED | NOT IN PARTICULAR | NOT IN PARTICULAR | |

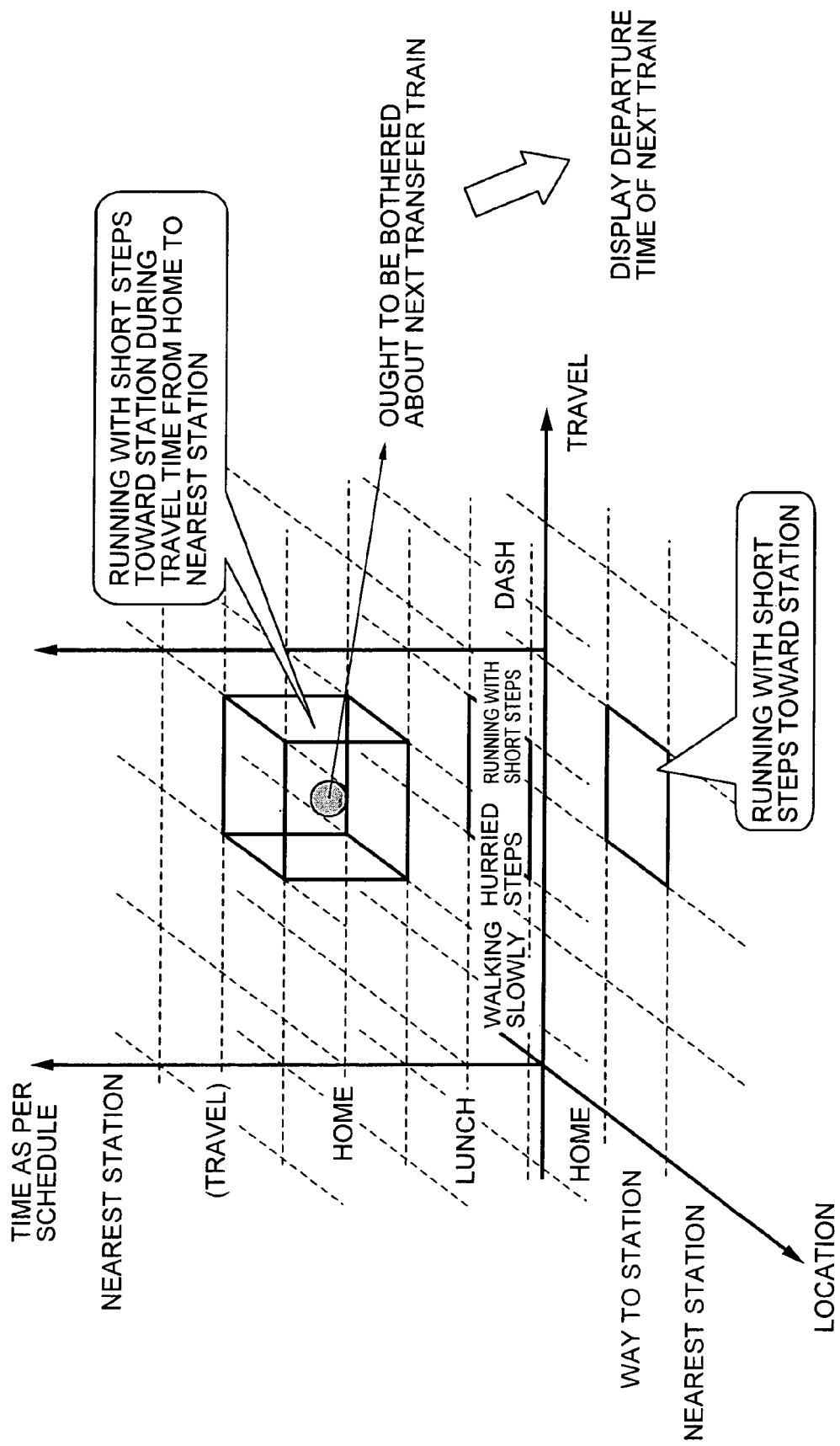

FIG. 20A

| TPO FACTOR AXES | | POSITION ON AXIS | CLOCK · SCHEDULE | OUTDOOR POSITION GPS | INDOOR-OUTDOOR SENSOR |
|---|---|---|---|---|---|
| TIMING | | | TIME · DAY · DATE AND ACTION | HOME · STATION · TOWN · TRAVEL DESTINATION | INDOOR / OUTDOOR |
| | CONVERSATION | TALKING / LISTENING / NIL | | | |
| TIME AND DATE | | | | | |
| | HOLIDAY | WEEK DAY / WEEKEND / HOLIDAY / FIRST DAY AFTER HOLIDAY | RELATION WITH HOLIDAY | UNDERSTANDING OF AS TO AT WHICH STAGE ONE IS AT PRESENT | |
| | DAILY LIFE TIME | WAKE-UP ~ BREAKFAST ~ LUNCH ~ DINNER ~ GO TO BED (POSITIONING IN CONTINUOUS TIME) | RELATION OF PRESENT TIME AND ACTION | RELATION OF OUTDOOR POSITION WITH ACTION | RELATION OF INDOOR-OUTDOOR AND ACTION |
| | DAILY WORKING TIME | GO TO WORK ~ TRAVEL ~ EVENT (BUSINESS TRIP / LEISURE ETC.) ~ TRAVEL ~ RETURN HOME | | | |
| | NON-DAILY TIME | DEPARTURE ~ TRAVEL ~ EVENT (BUSINESS TRIP / LEISURE ETC.) ~ TRAVEL ~ RETURN | | | |
| PLACE | | | | | |
| | LOCATION | HOME (BED ROOM / LIVING ROOM / DINING ROOM / OTHERS) / STATION / SHOP / HOSPITAL / OFFICE ROOM / CONFERENCE ROOM / RESTING ROOM / OTHERS) / MOVIE THEATRE / APART FROM THIS INDOOR STADIUM / SIGHTSEEING SPOT / TOWN / SEA · MOUNTAIN / OUTDOOR OTHER THAN THESE | POSITION AS PER SCHEDULE | HOME · STATION · TOWN · TRAVEL DESTINATION | INDOOR / OUTDOOR |
| | TRAVEL | PUBLIC TRANSPORT / DRIVE BY SELF (CAR · VEHICLE) / WALKING (SLOWLY ↔ DASH) / NO TRAVEL | TRAVEL AS PER SCHEDULE | TRAVELLING SPEED · ROUTE | PLATFORM, IN CAR ETC. |

FIG. 20B

| TPO FACTOR AXES | | POSITION ON AXIS | MOVEMENT MEASUREMENT SENSOR<br>SHAKING OF ARM (BODY MOVEMENT) | EXTERNAL SOUND MIC<br>DEGREE OF TENSION ACCORDING TO SURROUNDING SOUND / VOICE | BONE CONDUCTION MIC<br>SOUND EMITTED FROM BODY | FOOT PRESSURE SENSOR<br>WALKING, STANDING UPRIGHT, WEIGHT, LOAD |
|---|---|---|---|---|---|---|
| TIMING | | | | | | |
| | CONVERSATION | TALKING / LISTENING / NIL | | IN CONVERSATION | IN CONVERSATION | |
| TIME AND DATE | | | | | | |
| | HOLIDAY | WEEK DAY / WEEKEND / HOLIDAY / FIRST DAY AFTER HOLIDAY | | | | |
| | DAILY LIFE TIME | WAKE-UP ~ BREAKFAST ~ LUNCH ~ DINNER ~ GO TO BED (POSITIONING IN CONTINUOUS TIME) | | RELATION BETWEEN SURROUNDING SOUND AND ACTION | MEAL | |
| | DAILY WORKING TIME | GO TO WORK ~ TRAVEL ~ EVENT (BUSINESS TRIP / LEISURE ETC.) ~ TRAVEL ~ RETURN HOME | | | | |
| | NON-DAILY TIME | DEPARTURE ~ TRAVEL ~ EVENT (BUSINESS TRIP / LEISURE ETC.) ~ TRAVEL ~ RETURN | | | | |
| PLACE | | | | | | |
| | LOCATION | HOME (BED ROOM / LIVING ROOM / DINING ROOM / OTHERS) / STATION / SHOP / HOSPITAL / OFFICE ROOM / CONFERENCE ROOM / RESTING ROOM / OTHERS) / MOVIE THEATRE / APART FROM THIS INDOOR STADIUM / SIGHTSEEING SPOT / TOWN / SEA · MOUNTAIN / OUTDOOR OTHER THAN THESE | | | | |
| | TRAVEL | PUBLIC TRANSPORT / DRIVE BY SELF (CAR · VEHICLE) / WALKING (SLOWLY  DASH) / NO TRAVEL | FLUCTUATION (CHANGE) PATTERN | | | |

FIG. 21

| TPO FACTOR AXES | | POSITION ON AXIS | INFORMATION | | NEWS | | | MAIL | |
|---|---|---|---|---|---|---|---|---|---|
| | | | NAVIGATION | TRAFFIC INFORMATION | IMMEDIATE NEWS DIRECTLY RELATED TO WORK | NEW · HOBBY INFORMATION | URGENT · IMPORTANT MAIL | GENERAL WORK AND OTHER MAIL |
| TIMING | CONVERSATION | TALKING / LISTENING / NIL | | NOT TALKING | NOT TALKING | NO CONVERSATION | NOT TALKING | NO CONVERSATION |
| TIME AND DATE | HOLIDAY | WEEK DAY / WEEKEND / HOLIDAY / FIRST DAY AFTER HOLIDAY | | | | | | |
| | DAILY LIFE TIME | WAKE-UP ~ BREAKFAST ~ LUNCH ~ DINNER ~ GO TO BED (POSITIONING IN CONTINUOUS TIME) | | | | STIPULATED TIME | | STIPULATED TIME |
| | DAILY WORKING TIME | GO TO WORK ~ TRAVEL ~ EVENT (BUSINESS TRIP / LEISURE ETC.) ~ TRAVEL ~ RETURN HOME | | | | | | |
| | NON-DAILY TIME | DEPARTURE ~ TRAVEL ~ EVENT (BUSINESS TRIP / LEISURE ETC.) ~ TRAVEL ~ RETURN | DESTINATION | | | NOT DISPLAYED DURING LEISURE TIME | | |
| PLACE | LOCATION | HOME (BED ROOM / LIVING ROOM / DINING ROOM / OTHERS) / STATION / SHOP / HOSPITAL / OFFICE ROOM / CONFERENCE ROOM / RESTING ROOM / OTHERS) / MOVIE THEATRE / APART FROM THIS INDOOR STADIUM / SIGHTSEEING SPOT / TOWN / SEA · MOUNTAIN / OUTDOOR OTHER THAN THESE | IT IS AN UNFAMILIAR PLACE. PRESENT PLACE | | | NOT DISPLAYED FOR SIGHTSEEING SPOT · SEA MOUNTAIN ETC. | | |
| | TRAVEL | PUBLIC TRANSPORT / DRIVE BY SELF (CAR · VEHICLE) / WALKING (SLOWLY↔DASH) / NO TRAVEL | WALKING | | | | | |

FIG. 24A

| LIFE SCENE OF USER | FUNCTION OF SYSTEM (PROVIDING INFORMATION, ENVIRONMENT CONTROL, ACTION SUPPORT) | SENSOR BASED DATA USED ||||||||
|---|---|---|---|---|---|---|---|---|---|
| | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION |
| | | | | | | | | | OTHER SENSOR INFORMATION: AWAKE |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | AT HOME, BEFORE LEAVING FOR WORK | | | | | | | | |
| 1 I DID NOT HAVE TO BE AWAKEN BY THE ALARM BELL, AND TODAY ALSO I WOKE UP NATURALLY AND IN A PLEASANT MOOD | CONTROLLING ENVIRONMENT SUCH AS LIGHT, SOUND, SMELL, AND TEMPERATURE AND PROVIDING PLEASANT WAKE UP | A | | B | A | A | B | A | B |
| 2 AS I WOKE UP, TIME AND TODAY'S WEATHER WERE DISPLAYED ON THE BACKGROUND OF OUTSIDE CONDITIONS | DETECTING WAKING UP AND PROVIDING INFORMATION REQUIRED AS FIRST THING IN THE MORNING | A | | A | B | A | | B | |
| 3 IT'S HALF PAST SIX, AND SLIGHTLY EARLIER THAN USUAL. TODAY IT LOOKS LIKE IT IS GOING TO RAIN FROM THE MORNING. | SETTING WAKE-UP TIME ACCORDING TO SCHEDULE, WEATHER, AND TRAFFIC CONDITIONS | A | A | | | | | | |
| 4 AS I HEADED TO THE WASH BASIN, PHYSICAL CONDITION MONITOR WAS DISPLAYED. IN PASSING, I CHECKED MY FACIAL COMPLEXION IN THE MIRROR. PREVIOUS DAY I HAD A BIT TOO MUCH OF ALCOHOL, BUT BECAUSE OF THE SOUND SLEEP, MY PHYSICAL CONDITION SEEMS TO BE GOOD. | DISPLAY OF SLEEPING CONDITION AND HEALTH CONDITION BY PHYSICAL CONDITION MONITOR | | A | B | A | A | A | B | |

FIG. 24B

| LIFE SCENE OF USER | FUNCTION OF SYSTEM (PROVIDING INFORMATION, ENVIRONMENT CONTROL, ACTION SUPPORT) | SENSOR BASED DATA USED ||||||||
|---|---|---|---|---|---|---|---|---|---|
| | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |

SETTING: 35 YEAR OLD SALESMAN WORKING AWAY FROM HOME. HOBBY IS WATCHING BASEBALL. STARTED DEALING IN STOCKS HALF YEAR AGO, DUE TO NATURE OF WORK, MANY OCCASIONS TO DRINK ALCOHOL. HAS BEEN PUTTING ON WEIGHT RECENTLY. TRYING TO CONTROL WEIGHT.

| Scene | Function | Hour·Time | Position·Location | Walking·Movement State | Circulatory Organ Condition | Respiratory Organ Condition | Eye | Body Temp | GSR | Other |
|---|---|---|---|---|---|---|---|---|---|---|
| AT HOME, BEFORE LEAVING FOR WORK | | | | | | | | | | |
| 5 HOWEVER, SINCE THERE IS AN INDICATION OF VITAMIN C AND WATER REPLENISHMENT, LET'S HAVE FRESH JUICE IN THE MORNING | DISPLAY OF EATING ADVICE IS BY PHYSICAL MONITOR | | | | | | | | | |
| 6 WHEN I SAT ON THE TABLE, TODAY'S SCHEDULE WAS DISPLAYED. TODAY THERE IS A MEETING FROM THE MORNING | CALLING AND DISPLAYING SCHEDULE INFORMATION | B | B | | | | | | | |
| 7 I HAVE ALREADY CHECKED NEWLY ARRIVED MAIL. PREPARATION FOR THE PRESENTATION IN THE MEETING IS THOROUGHLY DONE. STILL, LET'S GO THROUGH THE MATERIAL ONE MORE TIME. | CALLING AND DISPLAYING INFORMATION SET BEFOREHAND SUCH AS MAIL, NEWS, AND PERSONAL INFORMATION | A | A | A | A | A | | | | |
| 8 AS THE TIME FOR LEAVING GOT CLOSER, AN ICON WAS DISPLAYED. I HAVE TO START PREPARING. IT'S A BIT EARLY, BUT IT LOOKS LIKE TRAINS ARE DELAYED DUE TO AN ACCIDENT | SETTING AND DISPLAYING DEPARTURE TIME ACCORDING TO THE SCHEDULE, WEATHER FORECAST, AND TRAFFIC CONDITION | A | A | A | | | | | | |
| 9 AS I HEADED FOR THE ENTRANCE OF THE HOUSE, A LIST OF THINGS TO BE CARRIED WAS DISPLAYED. TAKE AN UMBRELLA… OH NO! I WAS ABOUT TO FORGET THE INVITATION CARD FOR THE RECEPTION IN THE EVENING. | CHECKING THINGS TO BE CARRIED ACCORDING TO THE SCHEDULE | A | A | | | | | | | |

FIG. 24C

| | | Scenario 1 | Scenario 2 | Scenario 3 | Scenario 4 |
|---|---|---|---|---|---|
| NON-SENSOR BASED DATA USED (KNOWLEDGE DB ETC.) (INFORMATION USED FOR JUDGMENT AND PROVIDING) | OTHER | ENVIRONMENT CONTROL | | | |
| | ADVICE DB | | | | |
| | WEB CAMERA | | △ | | |
| | HISTORY INFORMATION | | | | PHYSICAL CONDITION |
| | PERSONAL INFORMATION DB | | | | |
| | TRAFFIC INFORMATION | | | △ | |
| | WEATHER FORECAST | | △ | △ | |
| | MAIL · NEWS | | | | |
| | TIMETABLE · TRANSFER | | | | |
| | SCHEDULE | | △ | △ | |
| | SHOP · FACILITY INFORMATION | | | | |
| | MAP INFORMATION | | | | |
| FUNCTION OF SYSTEM (PROVIDING INFORMATION, ENVIRONMENT CONTROL, ACTION SUPPORT) | | CONTROLLING ENVIRONMENT SUCH AS LIGHT, SOUND, SMELL, AND TEMPERATURE AND PROVIDING PLEASANT WAKE UP | DETECTING WAKING UP AND PROVIDING INFORMATION REQUIRED AS FIRST THING IN THE MORNING | SETTING WAKE-UP TIME ACCORDING TO SCHEDULE, WEATHER, AND TRAFFIC CONDITIONS | DISPLAY OF SLEEPING CONDITION AND HEALTH CONDITION BY PHYSICAL CONDITION MONITOR |
| LIFE SCENE OF USER — SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | AT HOME, BEFORE LEAVING FOR WORK | 1. I DID NOT HAVE TO BE AWAKEN BY THE ALARM BELL, AND TODAY ALSO I WOKE UP NATURALLY AND IN A PLEASANT MOOD | 2. AS I WOKE UP, TIME AND TODAY'S WEATHER WERE DISPLAYED ON THE BACKGROUND OF OUTSIDE CONDITIONS | 3. IT'S HALF PAST SIX, AND SLIGHTLY EARLIER THAN USUAL. TODAY IT LOOKS LIKE IT IS GOING TO RAIN FROM THE MORNING. | 4. AS I HEADED TO THE WASH BASIN, PHYSICAL CONDITION MONITOR WAS DISPLAYED. IN PASSING, I CHECKED MY FACIAL COMPLEXION IN THE MIRROR. PREVIOUS DAY I HAD A BIT TOO MUCH OF ALCOHOL, BUT BECAUSE OF THE SOUND SLEEP, MY PHYSICAL CONDITION SEEMS TO BE GOOD. |

FIG. 24D

| | | | | | NON-SENSOR BASED DATA USED (KNOWLEDGE DB ETC.) (INFORMATION USED FOR JUDGMENT AND PROVIDING) | | | | | | | | | FUNCTION OF SYSTEM (PROVIDING INFORMATION, ENVIRONMENT CONTROL, ACTION SUPPORT) |
|---|---|---|---|---|---|---|---|---|---|---|---|---|---|---|
| LIFE SCENE OF USER SETTING: 35 YEAR OLD SALESMAN. WORKING AWAY FROM HOME. HOBBY IS WATCHING BASEBALL. STARTED DEALING IN STOCKS HALF YEAR AGO DUE TO NATURE OF WORK, MANY OCCASIONS TO DRINK ALCOHOL. HAS BEEN PUTTING ON WEIGHT RECENTLY. TRYING TO CONTROL WEIGHT. | | OTHER | ADVICE DB | WEB CAMERA | HISTORY INFORMATION | PERSONAL INFORMATION DB | TRAFFIC INFORMATION | WEATHER FORECAST | MAIL·NEWS | TIMETABLE·TRANSFER | SCHEDULE | SHOP·FACILITY INFORMATION | MAP INFORMATION | |
| AT HOME, BEFORE LEAVING FOR WORK | | | | | | | | | | | | | | |
| 5 | HOWEVER, SINCE THERE IS AN INDICATION OF VITAMIN C AND WATER REPLENISHMENT, LET'S HAVE FRESH JUICE IN THE MORNING | | MEAL | | | | | | | | | | | DISPLAY OF EATING ADVICE IS BY PHYSICAL MONITOR |
| 6 | WHEN I SAT ON THE TABLE, TODAY'S SCHEDULE WAS DISPLAYED. TODAY THERE IS A MEETING FROM THE MORNING | | | | A | | | | | | | | | CALLING AND DISPLAYING SCHEDULE INFORMATION |
| 7 | I HAVE ALREADY CHECKED NEWLY ARRIVED MAIL. PREPARATION FOR THE PRESENTATION IN THE MEETING IS THOROUGHLY DONE. STILL, LET'S GO THROUGH THE MATERIAL ONE MORE TIME. | | | | | MATERIAL | | | A | | | | | CALLING AND DISPLAYING INFORMATION SET BEFOREHAND SUCH AS MAIL, NEWS, AND PERSONAL INFORMATION |
| 8 | AS THE TIME FOR LEAVING GOT CLOSER, AN ICON WAS DISPLAYED. I HAVE TO START PREPARING. IT'S A BIT EARLY, BUT IT LOOKS LIKE TRAINS ARE DELAYED DUE TO AN ACCIDENT | | | | WALKING SPEED | | A | | | A | A | | | SETTING AND DISPLAYING DEPARTURE TIME ACCORDING TO THE SCHEDULE, WEATHER FORECAST, AND TRAFFIC CONDITION |
| 9 | AS I HEADED FOR THE ENTRANCE OF THE HOUSE, A LIST OF THINGS TO BE CARRIED WAS DISPLAYED. TAKE AN UMBRELLA… OH NO! I WAS ABOUT TO FORGET THE INVITATION CARD FOR THE RECEPTION IN THE EVENING. | | | | | THINGS TO BE CARRIED | | | | | A | | | CHECKING THINGS TO BE CARRIED ACCORDING TO THE SCHEDULE |

FIG. 25A

| LIFE SCENE OF USER | | FUNCTION OF SYSTEM (PROVIDING INFORMATION, ENVIRONMENT CONTROL, ACTION SUPPORT) | SENSOR BASED DATA USED | | | | | | | | |
|---|---|---|---|---|---|---|---|---|---|---|---|
| | | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | | |
| DURING COMMUTING | | | | | | | | | | | |
| 10 | AS I STARTED WALKING TOWARDS THE STATION, THE TRANSFER INFORMATION WAS DISPLAYED. THE TRAIN TRAFFIC BEING AFFECTED DUE TO THE ACCIDENT, USE OF A PRIVATE RAILWAY LINE HAS BEEN PROPOSED. AS I DON'T WANT TO BE DELAYED FOR THE MEETING, LET'S USE A PRIVATE RAILWAY LINE. | DETECTING TRAVEL AND DISPLAYING INFORMATION SUPPORTING ACTION ACCORDING TO SCHEDULE THEREAFTER | A | A | A | | | | | | |
| 11 | IT'S A DIFFERENT ROUTE THAN THE USUAL ROUTE, BUT SINCE THE TRANSFER AND THE TIME ARE INFORMED, I AM FEELING AT EASE. | DISPLAYING INFORMATION SUPPORTING THE ACTION, SUITABLE TO THE ACTION | A | A | | | | | | | |
| 12 | THE TRAIN IS CROWDED. BUT, THANKS TO MEG, AS I CAN CHECK MAIL WHILE HOLDING THE STRAP. | DETECTION OF STATIONARY STATE, AND CALLING AND DISPLAYING INFORMATION SUCH AS MAIL AND NEWS. | B | A | A | | | | | | |

FIG. 25B

| LIFE SCENE OF USER | FUNCTION OF SYSTEM (PROVIDING INFORMATION, ENVIRONMENT CONTROL, ACTION SUPPORT) | SENSOR BASED DATA USED ||||||||
|---|---|---|---|---|---|---|---|---|---|
| | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| SETTING : 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | |
| DURING COMMUTING | | | | | | | | | | |
| 13 I CAN ALSO CHECK THE STOCK MARKET. FOR THE STOCKS IN HAND, LET US SEE THE SITUATION FOR A WHILE. | CALLING AND DISPLAYING INFORMATION SET BEFOREHAND, SUCH AS STOCK INFORMATION, AND NEWSPAPER. | B | A | A | | | | | | |
| 14 I HAVE FINISHED GATHERING THE INFORMATION. WHY NOT STUDY FOR THE TOEIC EXAM TO BE HELD NEXT MONTH. | DETECTING FREE TIME AND DISPLAYING INFORMATION WHICH ALLOWS TO RECOLLECT WHAT HAS BEEN THOUGHT OF DOING. SYSTEM RESOURCE BEING COMMON, CAN BE USED FOR LANGUAGE LEARNING DEPENDING ON CONTENTS | B | A | A | | | | | | |
| 15 THE ARRIVING TIME IS COMING CLOSER, AND AN ICON IS DISPLAYED. EVEN IF I CONCENTRATE ON MY STUDIES, NO WAY I AM GOING TO MISS MY STATION. SO, I AM AT EASE. | SETTING AND DISPLAYING TIME OF ACTION ACCORDING TO THE SCHEDULE | A | A | | | | | | | |

FIG. 25C

| LIFE SCENE OF USER | | FUNCTION OF SYSTEM (PROVIDING INFORMATION, ENVIRONMENT CONTROL, ACTION SUPPORT) | NON-SENSOR BASED DATA USED (KNOWLEDGE DB ETC.) (INFORMATION USED FOR JUDGMENT AND PROVIDING) | | | | | | | | | | |
|---|---|---|---|---|---|---|---|---|---|---|---|---|---|
| | | | MAP INFORMATION | SHOP · FACILITY INFORMATION | SCHEDULE | TIMETABLE · TRANSFER | MAIL · NEWS | WEATHER FORECAST | TRAFFIC INFORMATION | PERSONAL INFORMATION DB | HISTORY INFORMATION | WEB CAMERA | ADVICE DB | OTHER |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | | | | | |
| DURING COMMUTING | | | | | | | | | | | | | | |
| 10 | AS I STARTED WALKING TOWARDS THE STATION, THE TRANSFER INFORMATION WAS DISPLAYED. THE TRAIN TRAFFIC BEING AFFECTED DUE TO THE ACCIDENT, USE OF A PRIVATE RAILWAY LINE HAS BEEN PROPOSED. AS I DON'T WANT TO BE DELAYED FOR THE MEETING, LET'S USE A PRIVATE RAILWAY LINE. | DETECTING TRAVEL AND DISPLAYING INFORMATION SUPPORTING ACTION ACCORDING TO SCHEDULE THEREAFTER | A | | A | A | | | | | | | | |
| 11 | IT'S A DIFFERENT ROUTE THAN THE USUAL ROUTE, BUT SINCE THE TRANSFER AND THE TIME ARE INFORMED, I AM FEELING AT EASE. | DISPLAYING INFORMATION SUPPORTING THE ACTION, SUITABLE TO THE ACTION | A | | A | A | | | | | | | | |
| 12 | THE TRAIN IS CROWDED. BUT, THANKS TO MEG, AS I CAN CHECK MAIL WHILE HOLDING THE STRAP. | DETECTION OF STATIONARY STATE, AND CALLING AND DISPLAYING INFORMATION SUCH AS MAIL AND NEWS. | | | B | | A | | | | | | | |

FIG. 25D

| | | 13 | 14 | 15 |
|---|---|---|---|---|
| NON-SENSOR BASED DATA USED (KNOWLEDGE DB ETC.) (INFORMATION USED FOR JUDGMENT AND PROVIDING) | OTHER | | LEARNING MATERIAL | |
| | ADVICE DB | | | |
| | WEB CAMERA | | | |
| | HISTORY INFORMATION | | | |
| | PERSONAL INFORMATION DB | PREFERENCE | PLAN | |
| | TRAFFIC INFORMATION | | | |
| | WEATHER FORECAST | | | |
| | MAIL · NEWS | A | A | |
| | TIMETABLE · TRANSFER | | | A |
| | SCHEDULE | B | B | A |
| | SHOP · FACILITY INFORMATION | | | |
| | MAP INFORMATION | | | |
| | FUNCTION OF SYSTEM (PROVIDING INFORMATION, ENVIRONMENT CONTROL, ACTION SUPPORT) | CALLING AND DISPLAYING INFORMATION SET BEFOREHAND, SUCH AS STOCK INFORMATION, AND NEWSPAPER. | DETECTING FREE TIME AND DISPLAYING INFORMATION WHICH ALLOWS TO RECOLLECT WHAT HAS BEEN THOUGHT OF DOING. SYSTEM RESOURCE BEING COMMON, CAN BE USED FOR LANGUAGE LEARNING DEPENDING ON CONTENTS | SETTING AND DISPLAYING TIME OF ACTION ACCORDING TO THE SCHEDULE |
| LIFE SCENE OF USER SETTING : 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | DURING COMMUTING | 13 I CAN ALSO CHECK THE STOCK MARKET. FOR THE STOCKS IN HAND, LET US SEE THE SITUATION FOR A WHILE. | 14 I HAVE FINISHED GATHERING THE INFORMATION. WHY NOT STUDY FOR THE TOEIC EXAM TO BE HELD NEXT MONTH. | 15 THE ARRIVING TIME IS COMING CLOSER, AND AN ICON IS DISPLAYED. EVEN IF I CONCENTRATE ON MY STUDIES, NO WAY I AM GOING TO MISS MY STATION. SO, I AM AT EASE. |

FIG. 26A

| LIFE SCENE OF USER | FUNCTION OF SYSTEM (PROVIDING INFORMATION, ENVIRONMENT CONTROL, ACTION SUPPORT) | SENSOR BASED DATA USED ||||||||  |
|---|---|---|---|---|---|---|---|---|---|
| SETTING : 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| IN OFFICE | | | | | | | | | | |
| 16 WHILE I WAS ARRANGING THE MATERIAL, AN ICON WAS DISPLAYED. IN A MOVEMENT, IT'S TIME FOR THE MEETING. LET'S MAKE A MOVE. | SETTING AND DISPLAYING ACTION TIME ACCORDING TO SCHEDULE | A | A | | | | | | | |
| 17 NEXT, IT'S GOING TO BE MY PRESENTATION, AND "TENSION" ICON IS DISPLAYED. I AM BIT TENSED, BUT I MANAGED TO COOL DOWN WHEN I ADJUSTED MY BREATH ACCORDING TO THE RESPIRATION ADVICE. | MAKING JUDGMENT AND ADVICE ACCORDING TO HEART BEAT AND PERSPIRATION | | | | A | A | A | | A | TENSION |
| 18 SINCE MEG ACTS AS A PROMPTER DURING THE PRESENTATION, IT IS POSSIBLE TO SPEAK RIGHT TO THE POINT. MY PRESENTATION WAS RECEIVED QUITE WELL. | CALLING AND DISPLAYING PERSONAL DB INFORMATION | | | | | | | | | |

FIG. 26B

| LIFE SCENE OF USER SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | FUNCTION OF SYSTEM (PROVIDING INFORMATION, ENVIRONMENT CONTROL, ACTION SUPPORT) | SENSOR BASED DATA USED ||||||||  |
|---|---|---|---|---|---|---|---|---|---|
| | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| | | | | | | | | | | TENSION |
| IN OFFICE | | | | | | | | | | |
| 19 THE PRESENTATION WENT WELL. SO LET'S TAKE A BREATHER IN THE RESTING PLACE. MY CHILD'S SMILING FACE WAS DISPLAYED ON THE DISPLAY. | DETECTING RELEASING OF TENSION AND DISPLAYING RELAX IMAGE | | ∠ | ∠ | ∠ | ∠ | ∠ | | ∠ | |
| 20 WHEN I RETURNED TO THE DESK, THE SCHEDULE WAS DISPLAYED. SINCE I HAVE TO WORK OUTSIDE IN THE POST LUNCH SESSION, I HAVE TO ARRANGE THE MATERIAL TILL LUNCH TIME AND TO TAKE LUNCH ON SITE. | DETECTING RETURN TO THE DESK, AND CALLING AND DISPLAYING THE SCHEDULE | ∠ | ∠ | ∠ | | | | | | |
| 21 WHILE I WAS ARRANGING THE MATERIAL, AN ICON WAS DISPLAYED. IN A MOVEMENT, IT'S TIME TO LEAVE. NEXT, THE TRANSFER INFORMATION WAS ALSO DISPLAYED. THE RAIN ALSO SEEMS TO HAVE STOPPED. INFORMATION OF CONVENIENT TRANSFER OF METRO BUT WITH SLIGHTLY LONGER WALKING DISTANCE HAS BEEN DISPLAYED | SETTING AND DISPLAYING ACTION TIME ACCORDING TO SCHEDULE, AND POSITION, WEATHER, AND TRAFFIC SITUATION. | ∠ | ∠ | | | | | | | |

FIG. 26C

| | | FUNCTION OF SYSTEM (PROVIDING INFORMATION, ENVIRONMENT CONTROL, ACTION SUPPORT) | | | |
|---|---|---|---|---|---|
| NON-SENSOR BASED DATA USED (KNOWLEDGE DB ETC.) (INFORMATION USED FOR JUDGMENT AND PROVIDING) | OTHER | | | | |
| | ADVICE DB | | | RESPIRATION METHOD | |
| | WEB CAMERA | | | | |
| | HISTORY INFORMATION | | | | |
| | PERSONAL INFORMATION DB | | | | MATERIAL |
| | TRAFFIC INFORMATION | | | | |
| | WEATHER FORECAST | | | | |
| | MAIL · NEWS | | | | |
| | TIMETABLE · TRANSFER | | | | |
| | SCHEDULE | | A | | |
| | SHOP · FACILITY INFORMATION | | | | |
| | MAP INFORMATION | | | | |

| | LIFE SCENE OF USER | FUNCTION OF SYSTEM (PROVIDING INFORMATION, ENVIRONMENT CONTROL, ACTION SUPPORT) |
|---|---|---|
| | SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | |
| IN OFFICE | | |
| 16 | WHILE I WAS ARRANGING THE MATERIAL, AN ICON WAS DISPLAYED. IN A MOVEMENT, IT'S TIME FOR THE MEETING. LET'S MAKE A MOVE. | SETTING AND DISPLAYING ACTION TIME ACCORDING TO SCHEDULE |
| 17 | NEXT, IT'S GOING TO BE MY PRESENTATION, AND "TENSION" ICON IS DISPLAYED. I AM BIT TENSED, BUT I MANAGED TO COOL DOWN WHEN I ADJUSTED MY BREATH ACCORDING TO THE RESPIRATION ADVICE. | MAKING JUDGMENT AND ADVICE ACCORDING TO HEART BEAT AND PERSPIRATION |
| 18 | SINCE MEG ACTS AS A PROMPTER DURING THE PRESENTATION, IT IS POSSIBLE TO SPEAK RIGHT TO THE POINT. MY PRESENTATION WAS RECEIVED QUITE WELL. | CALLING AND DISPLAYING PERSONAL DB INFORMATION |

FIG. 26D

| LIFE SCENE OF USER<br>SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | FUNCTION OF SYSTEM (PROVIDING INFORMATION, ENVIRONMENT CONTROL, ACTION SUPPORT) | NON-SENSOR BASED DATA USED (KNOWLEDGE DB ETC.) (INFORMATION USED FOR JUDGMENT AND PROVIDING) | | | | | | | | | | | |
|---|---|---|---|---|---|---|---|---|---|---|---|---|---|
| | | MAP INFORMATION | SHOP · FACILITY INFORMATION | SCHEDULE | TIMETABLE · TRANSFER | MAIL · NEWS | WEATHER FORECAST | TRAFFIC INFORMATION | PERSONAL INFORMATION DB | HISTORY INFORMATION | WEB CAMERA | ADVICE DB | OTHER |
| IN OFFICE | | | | | | | | | | | | | |
| 19 THE PRESENTATION WENT WELL. SO LET'S TAKE A BREATHER IN THE RESTING PLACE. MY CHILD'S SMILING FACE WAS DISPLAYED ON THE DISPLAY. | DETECTING RELEASING OF TENSION AND DISPLAYING RELAX IMAGE | | | | | | | | PLEASANT IMAGE | | | | |
| 20 WHEN I RETURNED TO THE DESK, THE SCHEDULE WAS DISPLAYED. SINCE I HAVE TO WORK OUTSIDE IN THE POST LUNCH SESSION, I HAVE TO ARRANGE THE MATERIAL TILL LUNCH TIME AND TO TAKE LUNCH ON SITE. | DETECTING RETURN TO THE DESK, AND CALLING AND DISPLAYING THE SCHEDULE | | | △ | △ | | | | | | | | |
| 21 WHILE I WAS ARRANGING THE MATERIAL, AN ICON WAS DISPLAYED. IN A MOVEMENT, IT'S TIME TO LEAVE. NEXT, THE TRANSFER INFORMATION WAS ALSO DISPLAYED. THE RAIN ALSO SEEMS TO HAVE STOPPED. INFORMATION OF CONVENIENT TRANSFER OF METRO BUT WITH SLIGHTLY LONGER WALKING DISTANCE HAS BEEN DISPLAYED | SETTING AND DISPLAYING ACTION TIME ACCORDING TO SCHEDULE, AND POSITION, WEATHER, AND TRAFFIC SITUATION. | △ | | △ | △ | | | △ | PREFERENCE | SELECTION TREND | | | |

FIG. 27A

| LIFE SCENE OF USER | FUNCTION OF SYSTEM (PROVIDING INFORMATION, ENVIRONMENT CONTROL, ACTION SUPPORT) | SENSOR BASED DATA USED ||||||||||
|---|---|---|---|---|---|---|---|---|---|---|---|
| | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION | |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | | |
| TRAVEL TO SALES DESTINATION | | | | | | | | | | | |
| 22 EVEN IN A CASE OF A PLACE VISITING FOR THE FIRST TIME, I AM AT EASE SINCE THE INFORMATION SUCH AS THE MOST SUITABLE PLACE TO GET ON THE MEANS OF TRANSPORT AND EXIT OF METRO IS PROVIDED. | DISPLAYING INFORMATION TO SUPPORT ACTION, ACCORDING TO THE ACTION (NAVIGATION ACCORDING TO TRAVEL) | A | A | A | | | | | | | |
| IN A TOWN NEAR SALES DESTINATION | | | | | | | | | | | |
| 23 I ARRIVED AT THE SITE AS PER THE SCHEDULE. WHEN I FELT THAT I AM HUNGRY, THE INFORMATION OF NEARBY SET MEAL RESTAURANTS WAS DISPLAYED. | DETECTING AND GUIDING TO EATING PLACES BASED ON TIME AND PRESENT PLACE, EMPTY STOMACH CONDITION, AND FURTHERMORE PREFERENCE AND MEAL HISTORY FROM PERSONAL DATABASE | A | A | | | | | | | EMPTY STOMACH · PHYSICAL CONDITION | |

FIG. 27B

| LIFE SCENE OF USER | | FUNCTION OF SYSTEM (PROVIDING INFORMATION, ENVIRONMENT CONTROL, ACTION SUPPORT) | SENSOR BASED DATA USED | | | | | | | |
|---|---|---|---|---|---|---|---|---|---|---|
| | | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |

SETTING : 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT.

| | | | | | |
|---|---|---|---|---|---|
| IN A TOWN NEAR SALES DESTINATION | | | | | |
| 24 | AS I ENTERED THE RESTAURANT, RECOMMENDED MENU WAS DISPLAYED. MAY BE BECAUSE YESTERDAY THERE WAS A DRINKING PARTY, NOT TOO HEAVY EATABLES ARE RECOMMENDED. | MEAL ADVICE BASED ON PHYSICAL CONDITION AND MEAL HISTORY | A | A | |
| 25 | I FELT LIKE NEGLECTING, BUT DEVIATION FROM THE TARGET BODY WEIGHT WAS DISPLAYED. IN FACT, I HAVE BEEN CONTROLLING THE BODY WEIGTH AFTER BEING TOLD BY THE DOCTOR. SINCE STOMACH HAS ALSO BEEN STICKING OUT RECENTLY, LET'S FOLLOW THE INSTRUCTIONS. | PROVIDING STIMULATING INFORMATION TIMELY FOR ENCOURAGING SELF CONTROL | A | A | |

FIG. 27C

SETTING: 35 YEAR OLD SALESMAN WORKING AWAY FROM HOME. HOBBY IS WATCHING BASEBALL. STARTED DEALING IN STOCKS HALF YEAR AGO DUE TO NATURE OF WORK. MANY OCCASIONS TO DRINK ALCOHOL. HAS BEEN PUTTING ON WEIGHT RECENTLY. TRYING TO CONTROL WEIGHT.

| | | | 22 | 23 |
|---|---|---|---|---|
| LIFE SCENE OF USER | | | TRAVEL TO SALES DESTINATION: EVEN IN A CASE OF A PLACE VISITING FOR THE FIRST TIME, I AM AT EASE SINCE THE INFORMATION SUCH AS THE MEANS SUITABLE PLACE TO GET ON THE MEANS OF TRANSPORT AND EXIT OF METRO IS PROVIDED. | IN A TOWN NEAR SALES DESTINATION: I ARRIVED AT THE SITE AS PER THE SCHEDULE. WHEN I FELT THAT I AM HUNGRY, THE INFORMATION OF NEARBY SET MEAL RESTAURANTS WAS DISPLAYED. |
| FUNCTION OF SYSTEM (PROVIDING INFORMATION, ENVIRONMENT CONTROL, ACTION SUPPORT) | | | DISPLAYING INFORMATION TO SUPPORT ACTION, ACCORDING TO THE ACTION (NAVIGATION ACCORDING TO TRAVEL) | DETECTING AND GUIDING TO EATING PLACES BASED ON TIME AND PRESENT PLACE, EMPTY STOMACH CONDITION, AND FURTHERMORE PREFERENCE AND MEAL HISTORY FROM PERSONAL DATABASE |
| NON-SENSOR BASED DATA USED (KNOWLEDGE DB ETC.) (INFORMATION USED FOR JUDGMENT AND PROVIDING) | OTHER | | | |
| | ADVICE DB | | | |
| | WEB CAMERA | | | |
| | HISTORY INFORMATION | SELECTION TREND | | |
| | PERSONAL INFORMATION DB | PREFERENCE | | |
| | TRAFFIC INFORMATION | | | |
| | WEATHER FORECAST | | | |
| | MAIL · NEWS | | | |
| | TIMETABLE · TRANSFER | | A | |
| | SCHEDULE | | | A |
| | SHOP · FACILITY INFORMATION | | | A |
| | MAP INFORMATION | | A | A |

FIG. 27D

| LIFE SCENE OF USER | FUNCTION OF SYSTEM (PROVIDING INFORMATION, ENVIRONMENT CONTROL, ACTION SUPPORT) | NON-SENSOR BASED DATA USED (KNOWLEDGE DB ETC.) (INFORMATION USED FOR JUDGMENT AND PROVIDING) | | | | | | | | | | |
|---|---|---|---|---|---|---|---|---|---|---|---|---|
| | | MAP INFORMATION | SHOP · FACILITY INFORMATION | SCHEDULE | TIMETABLE · TRANSFER | MAIL · NEWS | WEATHER FORECAST | TRAFFIC INFORMATION | PERSONAL INFORMATION DB | HISTORY INFORMATION | WEB CAMERA | ADVICE DB | OTHER |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | | | | |
| IN A TOWN NEAR SALES DESTINATION | | | | | | | | | | | | | |
| 24 AS I ENTERED THE RESTAURANT, RECOMMENDED MENU WAS DISPLAYED. MAY BE BECAUSE YESTERDAY THERE WAS A DRINKING PARTY, NOT TOO HEAVY EATABLES ARE RECOMMENDED. | MEAL ADVICE BASED ON PHYSICAL CONDITION AND MEAL HISTORY | | A | | | | | | PHYSICAL CONDITION | MEAL | | MEAL | |
| 25 I FELT LIKE NEGLECTING, BUT DEVIATION FROM THE TARGET BODY WEIGHT WAS DISPLAYED. IN FACT, I HAVE BEEN CONTROLLING THE BODY WEIGTH AFTER BEING TOLD BY THE DOCTOR. SINCE STOMACH HAS ALSO BEEN STICKING OUT RECENTLY, LET'S FOLLOW THE INSTRUCTIONS. | PROVIDING STIMULATING INFORMATION TIMELY FOR ENCOURAGING SELF CONTROL | | | | | | | | PHYSICAL CONDITION | EXERCISE | | HEALTH CARE | |

FIG. 28A

| LIFE SCENE OF USER | FUNCTION OF SYSTEM (PROVIDING INFORMATION, ENVIRONMENT CONTROL, ACTION SUPPORT) | SENSOR BASED DATA USED | | | | | | | |
|---|---|---|---|---|---|---|---|---|---|
| | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| SETTING : 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | |
| AT SALES DESTINATION | | | | | | | | | | |
| 26 EVEN IN A CASE OF A PLACE VISITING FOR THE FIRST TIME, SINCE THE MEG GUIDES UP TO THE SALES DESTINATION, I DON'T HAVE TO HANG AROUND CARRYING THE MAP. | DISPLAYING INFORMATION TO SUPPORT ACTION ACCORDING TO THE ACTION (NAVIGATION ACCORDING TO TRAVEL) | A | A | | | | | | | |
| 27 SALES AT THE FIRST DESTINATION FAILED. I WAS ALREADY DONE FOR BY THE COMPETITION. LET'S UPDATE THE SALES DB. | MAKING ACCESS TO IN-HOUSE DB BY USING COMMUNICATION FUNCTION. INPUTTING AUTOMATICALLY POSITION, HOUR INFORMATION | A | A | | | | | | | |
| 28 I PULLED MYSELF TOGETHER AND MOVED ONTO THE NEXT SALES DESTINATION. SINCE THE TRANSFER INFORMATION IS DISPLAYED ACCORDING TO THE REQUIREMENT, I CAN CONCENTRATE ON CHECKING THE INFORMATION OF SALES DESTINATIONS EVEN DURING THE TRAVEL. | NAVIGATION AND TRANSFER INFORMATION ACCORDING TO SCHEDULE AND PRESENT POSITION | A | A | | | | | | | |

FIG. 28B

| LIFE SCENE OF USER | | FUNCTION OF SYSTEM (PROVIDING INFORMATION, ENVIRONMENT CONTROL, ACTION SUPPORT) | SENSOR BASED DATA USED ||||||||||
|---|---|---|---|---|---|---|---|---|---|---|---|
| | | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| SETTING : 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. |||||||||||||
| AT SALES DESTINATION |||||||||||||
| 29 | BY THE GRACE OF GOD, THE SALES SUCCEEDED AT FIVE DESTINATIONS AND FAILED AT ONE. WHILE I WAS WAITING AT A SIGNAL, THE SECHEDULE WAS DISPLAYED. IT'S ABOUT TIME TO TRAVEL TO THE RECEPTION VENUE. | DETECTING STATIONARY CONDITION SUCH AS WAITING AT A SIGNAL, AND PROVIDING ACTION SUPPORTING INFORMATION | A | A | A | | | | | | |
| 30 | BECAUSE THE TRAVELLING METHOD IS NAVIGATED EVEN FROM AN UNFAMILIAR SALES DESTINATION, I FEEL AT EASE. | NAVIGATION ACCORDING TO THE SCHEDULE AND PRESENT POSITION, AND AUTOMATIC CREATING AND DISPLAYING OF TRANSFER INFORMATION | A | A | | | | | | | |

FIG. 28C

| | | 26 | 27 | 28 |
|---|---|---|---|---|
| LIFE SCENE OF USER | SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | AT SALES DESTINATION: EVEN IN A CASE OF A PLACE VISITING FOR THE FIRST TIME, SINCE THE MEG GUIDES UP TO THE SALES DESTINATION, I DON'T HAVE TO HANG AROUND CARRYING THE MAP. | SALES AT THE FIRST DESTINATION FAILED. I WAS ALREADY DONE FOR BY THE COMPETITION. LET'S UPDATE THE SALES DB. | I PULLED MYSELF TOGETHER AND MOVED ONTO THE NEXT SALES DESTINATION. SINCE THE TRANSFER INFORMATION IS DISPLAYED ACCORDING TO THE REQUIREMENT, I CAN CONCENTRATE ON CHECKING THE INFORMATION OF SALES DESTINATIONS EVEN DURING THE TRAVEL. |
| FUNCTION OF SYSTEM (PROVIDING INFORMATION, ENVIRONMENT CONTROL, ACTION SUPPORT) | | DISPLAYING INFORMATION TO SUPPORT ACTION ACCORDING TO THE ACTION (NAVIGATION ACCORDING TO TRAVEL) | MAKING ACCESS TO IN-HOUSE DB BY USING COMMUNICATION FUNCTION. INPUTTING AUTOMATICALLY POSITION, HOUR INFORMATION | NAVIGATION AND TRANSFER INFORMATION ACCORDING TO SCHEDULE AND PRESENT POSITION |
| NON-SENSOR BASED DATA USED (KNOWLEDGE DB ETC.) (INFORMATION USED FOR JUDGMENT AND PROVIDING) | MAP INFORMATION | △ | SALES DESTINATION | △ |
| | SHOP·FACILITY INFORMATION | | | |
| | SCHEDULE | | | △ |
| | TIMETABLE·TRANSFER | △ | | △ |
| | MAIL·NEWS | | | |
| | WEATHER FORECAST | | | |
| | TRAFFIC INFORMATION | | | △ |
| | PERSONAL INFORMATION DB | | MATERIAL | MATERIAL |
| | HISTORY INFORMATION | | | |
| | WEB CAMERA | | | |
| | ADVICE DB | | | |
| | OTHER | | SALES DB | |

FIG. 28D

| LIFE SCENE OF USER | | FUNCTION OF SYSTEM (PROVIDING INFORMATION, ENVIRONMENT CONTROL, ACTION SUPPORT) | NON-SENSOR BASED DATA USED (KNOWLEDGE DB ETC.) (INFORMATION USED FOR JUDGMENT AND PROVIDING) | | | | | | | | | | |
|---|---|---|---|---|---|---|---|---|---|---|---|---|---|
| | | | MAP INFORMATION | SHOP · FACILITY INFORMATION | SCHEDULE | TIMETABLE · TRANSFER | MAIL · NEWS | WEATHER FORECAST | TRAFFIC INFORMATION | PERSONAL INFORMATION DB | HISTORY INFORMATION | WEB CAMERA | ADVICE DB | OTHER |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | | | | |
| AT SALES DESTINATION | | | | | | | | | | | | | |
| 29 | BY THE GRACE OF GOD, THE SALES SUCCEEDED AT FIVE DESTINATIONS AND FAILED AT ONE. WHILE I WAS WAITING AT A SIGNAL, THE SECHEDULE WAS DISPLAYED. IT'S ABOUT TIME TO TRAVEL TO THE RECEPTION VENUE. | DETECTING STATIONARY CONDITION SUCH AS WAITING AT A SIGNAL, AND PROVIDING ACTION SUPPORTING INFORMATION | | | A | A | | | | | | | |
| 30 | BECAUSE THE TRAVELLING METHOD IS NAVIGATED EVEN FROM AN UNFAMILIAR SALES DESTINATION, I FEEL AT EASE. | NAVIGATION ACCORDING TO THE SCHEDULE AND PRESENT POSITION, AND AUTOMATIC CREATING AND DISPLAYING OF TRANSFER INFORMATION | A | | | A | | | | | | | |

FIG. 29A

| LIFE SCENE OF USER | FUNCTION OF SYSTEM (PROVIDING INFORMATION, ENVIRONMENT CONTROL, ACTION SUPPORT) | SENSOR BASED DATA USED ||||||||||
|---|---|---|---|---|---|---|---|---|---|---|
| | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | |
| AT RECEPTION VENUE | | | | | | | | | | |
| 31 I HAVE ARRIVED AT THE HOTEL. AS I WAS THINKING OF BUYING A FILM BEFORE GOING TO THE VENUE, THE DISPLAY CHANGED TO THE INFORMATION INSIDE THE FACILITY. | DETECTING AN ENTRY INTO A COMMERCIAL FACILITY, AND CHANGING TO INFORMATION INSIDE THE FACILITY | | A | | | | | | | |
| 32 OH YES! I HAVE HEARD THAT THE BREAD IN THIS HOTEL IS POPULAR. LET'S BUY ONE FOR TOMORROW'S BREAKFAST. | PROVIDING SHOP INFORMATION BASED ON INDIVIDUAL PREFERENCE AND ACTION HISTORY | | A | | | | | | | |

FIG. 29B

| LIFE SCENE OF USER | | FUNCTION OF SYSTEM (PROVIDING INFORMATION, ENVIRONMENT CONTROL, ACTION SUPPORT) | SENSOR BASED DATA USED | | | | | | | |
|---|---|---|---|---|---|---|---|---|---|---|
| | | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | | |
| AT RECEPTION VENUE | | | | | | | | | | | |
| 33 | I ARRIVED AT THE RECEPTION VENUE. THE SYSTEM IS IN THE SLEEP MODE. WITH THIS MODE, NOTHING WILL BE DISPLAYED EXCEPT IN A CASE OF EMERGENCY. | CONTROL OF EQUIPMENT ACCORDING TO TPO | | A | | | | | | |
| 34 | I HAVE GOTTEN SUCCESSFULLY THROUGH THE SPEECH. AS I WAS THINKING SO, I GOT A MAIL FROM THE DIVISION HEAD SAYING "PREPARE THE MATERIAL IMMEDIATELY FOR TOMORROW'S SPECIAL CONFERENCE". LET'S GO BACK TO THE OFFICE. | INTERRUPTION DISPLAY OF URGENT MAIL | | A | | | | | | |

FIG. 29C

LIFE SCENE OF USER

SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT.

AT RECEPTION VENUE

| | Life scene | FUNCTION OF SYSTEM (PROVIDING INFORMATION, ENVIRONMENT CONTROL, ACTION SUPPORT) | NON-SENSOR BASED DATA USED (KNOWLEDGE DB ETC.) (INFORMATION USED FOR JUDGMENT AND PROVIDING) | | | | | | | | | | |
|---|---|---|---|---|---|---|---|---|---|---|---|---|---|
| | | | MAP INFORMATION | SHOP · FACILITY INFORMATION | SCHEDULE | TIMETABLE · TRANSFER | MAIL · NEWS | WEATHER FORECAST | TRAFFIC INFORMATION | PERSONAL INFORMATION DB | HISTORY INFORMATION | WEB CAMERA | ADVICE DB | OTHER |
| 31 | I HAVE ARRIVED AT THE HOTEL. AS I WAS THINKING OF BUYING A FILM BEFORE GOING TO THE VENUE, THE DISPLAY CHANGED TO THE INFORMATION INSIDE THE FACILITY. | DETECTING AN ENTRY INTO A COMMERCIAL FACILITY, AND CHANGING TO INFORMATION INSIDE THE FACILITY | | A | | | | | | | | | | |
| 32 | OH YES! I HAVE HEARD THAT THE BREAD IN THIS HOTEL IS POPULAR. LET'S BUY ONE FOR TOMORROW'S BREAKFAST. | PROVIDING SHOP INFORMATION BASED ON INDIVIDUAL PREFERENCE AND ACTION HISTORY | | A | | | | | | PREFERENCE | PURCHASE | | | |

FIG. 29D

| LIFE SCENE OF USER | FUNCTION OF SYSTEM (PROVIDING INFORMATION, ENVIRONMENT CONTROL, ACTION SUPPORT) | NON-SENSOR BASED DATA USED (KNOWLEDGE DB ETC.) (INFORMATION USED FOR JUDGMENT AND PROVIDING) | | | | | | | | | |
|---|---|---|---|---|---|---|---|---|---|---|---|
| | | MAP INFORMATION | SHOP · FACILITY INFORMATION | SCHEDULE | TIMETABLE · TRANSFER | MAIL · NEWS | WEATHER FORECAST | TRAFFIC INFORMATION | PERSONAL INFORMATION DB | HISTORY INFORMATION | WEB CAMERA | ADVICE DB | OTHER |
| SETTING : 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | | | | |
| AT RECEPTION VENUE | | | | | | | | | | | | | |
| 33 I ARRIVED AT THE RECEPTION VENUE. THE SYSTEM IS IN THE SLEEP MODE. WITH THIS MODE, NOTHING WILL BE DISPLAYED EXCEPT IN A CASE OF EMERGENCY. | CONTROL OF EQUIPMENT ACCORDING TO TPO | | | | | | | | | | | | |
| 34 I HAVE GOTTEN SUCCESSFULLY THROUGH THE SPEECH. AS I WAS THINKING SO, I GOT A MAIL FROM THE DIVISION HEAD SAYING "PREPARE THE MATERIAL IMMEDIATELY FOR TOMORROW'S SPECIAL CONFERENCE". LET'S GO BACK TO THE OFFICE. | INTERRUPTION DISPLAY OF URGENT MAIL | | | | | A | | | | | | | |

FIG. 30A

| LIFE SCENE OF USER | FUNCTION OF SYSTEM (PROVIDING INFORMATION, ENVIRONMENT CONTROL, ACTION SUPPORT) | SENSOR BASED DATA USED ||||||||
|---|---|---|---|---|---|---|---|---|---|
| | | HOUR·TIME | POSITION·LOCATION | WALKING·MOVEMENT STATE | CIRCULATORY ORGAN CONDITION | RESPIRATORY ORGAN CONDITION | EYE CONDITION | BODY TEMPERATURE | GSR·PERSPIRATION | OTHER SENSOR INFORMATION |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | FATIGUE |
| AFTER RETURNING TO OFFICE | | | | | | | | | | |
| 35 I HAVE FINISHED PREPARING 70% OF THE MATERIAL. SINCE THERE IS AN INDICATION FOR A BREAK, LET'S TAKE A BREATHER. | MONITORING PHYSICAL CONDITION EVEN DURING THE WORK TO PREVENT OVERWORK AND DISPLAYING TO ENCOURAGE TIMELY BREAK. | △ | △ | | △ | △ | △ | | | |
| 36 AS I WAS TAKING A BREAK, RESULT OF THE NIGHT GAME WAS DISPLAYED. | GOING INTO WORK MODE AND CUTTING OFF UNNECESSARY INFORMATION WHILE SITTING AT THE DESK. DETECTING A MOVEMENT TO A BREAK CORNER AND DISPLAYING OTHER INFORMATION | | △ | | | | | | | |
| 37 I RETURNED TO THE DESK ONCE AGAIN AND FINISHED PREPARING THE MATERIAL. IT LOOKS LIKE THE DIVISION HEAD IS GOING TO GIVE A TREAT. | CHANGING TO WORK MODE | | △ | | | | | | | |

FIG. 30B

| | | | PHYSICAL CONDITION | MEAL | |
|---|---|---|---|---|---|
| SENSOR BASED DATA USED | | OTHER SENSOR INFORMATION | | | |
| | | GSR・PERSPIRATION | | | |
| | | BODY TEMPERATURE | | ᴀ | |
| | | EYE CONDITION | | | |
| | | RESPIRATORY ORGAN CONDITION | | | |
| | | CIRCULATORY ORGAN CONDITION | | | |
| | | WALKING・MOVEMENT STATE | | ᴀ | |
| | | POSITION・LOCATION | ᴀ | ᴀ | ᴀ |
| | | HOUR・TIME | ᴀ | | ᴀ |
| | FUNCTION OF SYSTEM (PROVIDING INFORMATION, ENVIRONMENT CONTROL, ACTION SUPPORT) | | DISPLAYING INFORMATION SUPPORTING THE ACTION ACCORDING TO TIME AND PLACE | MONITORING INDEX TO BE WARNED | TRANSFER INFORMATION ACCORDING TO THE SCHEDULE, WEATHER FORECAST, AND TRAFFIC CONDITION |
| LIFE SCENE OF USER | SETTING : 35 YEAR OLD SALESMAN WORKING AWAY FROM HOME. HOBBY IS WATCHING BASEBALL. STARTED DEALING IN STOCKS HALF YEAR AGO DUE TO NATURE OF WORK. MANY OCCASIONS TO DRINK ALCOHOL. HAS BEEN PUTTING ON WEIGHT RECENTLY. TRYING TO CONTROL WEIGHT. | IN A TOWN NEAR THE OFFICE | | | |
| | | 38 AS I STOPPED IN FRONT OF A COOKSHOP, INFORMATION OF SEVERAL COOKSHOPS NEARBY WAS DISPLAYED. IT LOOKS LIKE A NEW COOKSHOP HAS OPENED AT A CORNER OF THE NEXT INTERSECTION. LET'S EAT THERE. | | | |
| | | 39 OH, THE BEER IS NICE. BUT THE URIC ACID VALUE WARNING IS DISPLAYED. | | | |
| | | 40 I WAS NEGLECTING, BUT THE INFORMATION ABOUT TIME TO LEAVE WAS DISPLAYED. OH, IT'S LATE. IF I DON'T LEAVE IN A MOMENT, IT LOOKS LIKE I AM NOT GOING TO BE IN TIME FOR THE LAST TRAIN. | | | |

FIG. 30C

| LIFE SCENE OF USER | FUNCTION OF SYSTEM (PROVIDING INFORMATION, ENVIRONMENT CONTROL, ACTION SUPPORT) | NON-SENSOR BASED DATA USED (KNOWLEDGE DB ETC.) (INFORMATION USED FOR JUDGMENT AND PROVIDING) |
|---|---|---|

SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT.

AFTER RETURNING TO OFFICE

| # | Life scene | Function of system | Data used |
|---|---|---|---|
| 35 | I HAVE FINISHED PREPARING 70% OF THE MATERIAL. SINCE THERE IS AN INDICATION FOR A BREAK, LET'S TAKE A BREATHER. | MONITORING PHYSICAL CONDITION EVEN DURING THE WORK TO PREVENT OVERWORK AND DISPLAYING TO ENCOURAGE TIMELY BREAK. | |
| 36 | AS I WAS TAKING A BREAK, RESULT OF THE NIGHT GAME WAS DISPLAYED. | GOING INTO WORK MODE AND CUTTING OFF UNNECESSARY INFORMATION WHILE SITTING AT THE DESK. DETECTING A MOVEMENT TO A BREAK CORNER AND DISPLAYING OTHER INFORMATION | PERSONAL INFORMATION DB: PREFERENCE; MAIL·NEWS: A |
| 37 | I RETURNED TO THE DESK ONCE AGAIN AND FINISHED PREPARING THE MATERIAL. IT LOOKS LIKE THE DIVISION HEAD IS GOING TO GIVE A TREAT. | CHANGING TO WORK MODE | |

Non-sensor based data categories: OTHER; ADVICE DB; WEB CAMERA; HISTORY INFORMATION; PERSONAL INFORMATION DB; TRAFFIC INFORMATION; WEATHER FORECAST; MAIL·NEWS; TIMETABLE·TRANSFER; SCHEDULE; SHOP·FACILITY INFORMATION; MAP INFORMATION

FIG. 30D

| NON-SENSOR BASED DATA USED (KNOWLEDGE DB ETC.) (INFORMATION USED FOR JUDGMENT AND PROVIDING) | 38 | 39 | 40 |
|---|---|---|---|
| OTHER | | | |
| ADVICE DB | | MEAL | |
| WEB CAMERA | | | |
| HISTORY INFORMATION | | MEAL | WALKING SPEED |
| PERSONAL INFORMATION DB | PREFERENCE | PHYSICAL CONDITION | |
| TRAFFIC INFORMATION | | | △ |
| WEATHER FORECAST | | | |
| MAIL · NEWS | | | |
| TIMETABLE · TRANSFER | | | △ |
| SCHEDULE | | | △ |
| SHOP · FACILITY INFORMATION | △ | △ | |
| MAP INFORMATION | △ | | △ |
| FUNCTION OF SYSTEM (PROVIDING INFORMATION, ENVIRONMENT CONTROL, ACTION SUPPORT) | DISPLAYING INFORMATION SUPPORTING THE ACTION ACCORDING TO TIME AND PLACE | MONITORING INDEX TO BE WARNED | TRANSFER INFORMATION ACCORDING TO THE SCHEDULE, WEATHER FORECAST, AND TRAFFIC CONDITION |
| LIFE SCENE OF USER — SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY, TRYING TO CONTROL WEIGHT. | 38 IN A TOWN NEAR THE OFFICE. AS I STOPPED IN FRONT OF A COOKSHOP, INFORMATION OF SEVERAL COOKSHOPS NEARBY WAS DISPLAYED. IT LOOKS LIKE A NEW COOKSHOP HAS OPENED AT A CORNER OF THE NEXT INTERSECTION. LET'S EAT THERE. | 39 OH, THE BEER IS NICE. BUT THE URIC ACID VALUE WARNING IS DISPLAYED. | 40 I WAS NEGLECTING, BUT THE INFORMATION ABOUT TIME TO LEAVE WAS DISPLAYED. OH, IT'S LATE. IF I DON'T LEAVE IN A MOMENT, IT LOOKS LIKE I AM NOT GOING TO BE IN TIME FOR THE LAST TRAIN. |

FIG. 31A

| LIFE SCENE OF USER | | FUNCTION OF SYSTEM (PROVIDING INFORMATION, ENVIRONMENT CONTROL, ACTION SUPPORT) | SENSOR BASED DATA USED | | | | | | | | |
|---|---|---|---|---|---|---|---|---|---|---|---|
| | | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| SETTING : 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | | |
| TO HOME | | | | | | | | | | | |
| 41 | BY USING THE WAITING TIME AND TRAVEL TIME OF THE TRAIN, TODAY'S NEWS IS DISPLAYED. AN IMAGE OF A VISITOR VISITED IN MY ABSENCE IS ALSO DISPLAYED. NOT BEING AT HOME IN THE DAY TIME HELPS ME. | DETECTING STATIONARY STATE AND INDICATING INFORMATION IN HIGHER PRIORITY ORDER | A | | | | | | | | |
| 42 | SOON I AM GOING TO REACH HOME. LIGHTS IN THE ROOMS ARE PUT ON AND I RECEIVED A TRANSMITTED IMAGE OF A WEB CAMERA. SINCE IT'S DANGEROUS, IT'S BETTER TO CHECK THE SITUATION BEFORE RETURNING HOME. | DETECTING REACHING CLOSER TO HOME, AND CHECKING SITUATION AT HOME BY A HOME SENSOR | A | A | A | | | | | | |
| 43 | I ARRIVED AT HOME. THE PORCH LIGHT IS ALSO PUT ON, AND THE ROOM TEMPERATURE IS ALSO PLEASANT. SINCE IT'S LATE, THE HOT WATER BATH IS ALSO READY. | DETECTING REACHING CLOSER TO HOME, AND PERFORMING CONTROL SUCH AS LIGHTS, AIR-CONDITIONING, AND WATER HEATER ACCORDING TO TIME AND ROOM TEMPERATURE | A | A | | | | | | | |

FIG. 31B

| LIFE SCENE OF USER | | FUNCTION OF SYSTEM (PROVIDING INFORMATION, ENVIRONMENT CONTROL, ACTION SUPPORT) | SENSOR BASED DATA USED | | | | | | | | |
|---|---|---|---|---|---|---|---|---|---|---|---|
| | | | HOUR · TIME | POSITION · LOCATION | WALKING · MOVEMENT STATE | CIRCULATORY ORGAN CONDITION | RESPIRATORY ORGAN CONDITION | EYE CONDITION | BODY TEMPERATURE | GSR · PERSPIRATION | OTHER SENSOR INFORMATION |
| SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | | | | | | | | | | | |
| TO HOME | | | | | | | | | | | |
| 44 | AS I CHANGED MY CLOTHES AND SETTLED, TOMORROW'S SCHEDULE WAS DISPLAYED. TOMORROW, THE SPECIAL CONFERENCE IS FROM 8 O'CLOCK. SCHEDULED TIME FOR LEAVING HAS ALREADY BEEN SET. | PREPARES AN ACTION PROGRAM FOR THE FOLLOWING DAY ACCORDING TO THE SCHEDULE | A | | | | | | | | |
| 45 | IT LOOKS LIKE IT WOULD BE BETTER TO TAKE THE HOT TUB BATH AT ONCE AND GO TO SLEEP. THE ADVICE DISPLAYED IS SAYING THE SAME THING. | ADVISING TIMING FOR ACTION ACCORDING TO THE SCHEDULE AND PHYSICAL CONDITION | A | A | | | | | | | |
| 46 | WHILE TAKING THE BATH, THE BED ROOM LIGHT IS PUT OFF AND CHANGED TO A WARM-COLOR LIGHT. THE FRAGRANCE OF LAVENDER IS WAFTING THROUGH THE AIR. IT LOOKS LIKE I AM GOING TO HAVE A GOOD SLEEP. | ENVIRONMENT CONTROL ACCORDING TO THE ACTION | A | A | | | | | | | |

FIG. 31C

| LIFE SCENE OF USER SETTING: 35 YEAR OLD SALESMAN WORKING AWAY FROM HOME. HOBBY IS WATCHING BASEBALL. STARTED DEALING IN STOCKS HALF YEAR AGO. DUE TO NATURE OF WORK, MANY OCCASIONS TO DRINK ALCOHOL. HAS BEEN PUTTING ON WEIGHT RECENTLY. TRYING TO CONTROL WEIGHT. | FUNCTION OF SYSTEM (PROVIDING INFORMATION, ENVIRONMENT CONTROL, ACTION SUPPORT) | NON-SENSOR BASED DATA USED (KNOWLEDGE DB ETC.) (INFORMATION USED FOR JUDGMENT AND PROVIDING) | | | | | | | | | | |
|---|---|---|---|---|---|---|---|---|---|---|---|
| | | MAP INFORMATION | SHOP · FACILITY INFORMATION | SCHEDULE | TIMETABLE · TRANSFER | MAIL · NEWS | WEATHER FORECAST | TRAFFIC INFORMATION | PERSONAL INFORMATION DB | HISTORY INFORMATION | WEB CAMERA | ADVICE DB | OTHER |
| TO HOME | | | | | | | | | | | | | |
| 41 BY USING THE WAITING TIME AND TRAVEL TIME OF THE TRAIN, TODAY'S NEWS IS DISPLAYED. AN IMAGE OF A VISITOR VISITED IN MY ABSENCE IS ALSO DISPLAYED. NOT BEING AT HOME IN THE DAY TIME HELPS ME. | DETECTING STATIONARY STATE AND INDICATING INFORMATION IN HIGHER PRIORITY ORDER | | | | A | A | | | | | | | |
| 42 SOON I AM GOING TO REACH HOME. LIGHTS IN THE ROOMS ARE PUT ON AND I RECEIVED A TRANSMITTED IMAGE OF A WEB CAMERA. SINCE IT'S DANGEROUS, IT'S BETTER TO CHECK THE SITUATION BEFORE RETURNING HOME. | DETECTING REACHING CLOSER TO HOME, AND CHECKING SITUATION AT HOME BY A HOME SENSOR | | | | | | | | | | A | | |
| 43 I ARRIVED AT HOME. THE PORCH LIGHT IS ALSO PUT ON, AND THE ROOM TEMPERATURE IS ALSO PLEASANT. SINCE IT'S LATE, THE HOT WATER BATH IS ALSO READY. | DETECTING REACHING CLOSER TO HOME, AND PERFORMING CONTROL SUCH AS LIGHTS, AIR-CONDITIONING, AND WATER HEATER ACCORDING TO TIME AND ROOM TEMPERATURE | | | | | | | | | | | | ENVIRONMENT CONTROL |

FIG. 31D

| | | NON-SENSOR BASED DATA USED (KNOWLEDGE DB ETC.) (INFORMATION USED FOR JUDGMENT AND PROVIDING) | | | |
|---|---|---|---|---|---|
| | OTHER | | | | ENVIRONMENT CONTROL |
| | ADVICE DB | | | HEALTH CARE | |
| | WEB CAMERA | | | | |
| | HISTORY INFORMATION | | | CUSTOM | CUSTOM |
| | PERSONAL INFORMATION DB | | | PHYSICAL CONDITION | PREFERENCE |
| | TRAFFIC INFORMATION | | | | |
| | WEATHER FORECAST | | A | | |
| | MAIL・NEWS | | | | |
| | TIMETABLE・TRANSFER | | A | | |
| | SCHEDULE | | A | A | A |
| | SHOP・FACILITY INFORMATION | | | | |
| | MAP INFORMATION | | | | |
| LIFE SCENE OF USER | | FUNCTION OF SYSTEM (PROVIDING INFORMATION, ENVIRONMENT CONTROL, ACTION SUPPORT) | | | |
| SETTING: 35 YEAR OLD SALESMAN WORKING AWAY FROM HOME. HOBBY IS WATCHING BASEBALL. STARTED DEALING IN STOCKS HALF YEAR AGO DUE TO NATURE OF WORK. MANY OCCASIONS TO DRINK ALCOHOL. HAS BEEN PUTTING ON WEIGHT RECENTLY. TRYING TO CONTROL WEIGHT. | TO HOME | | | | |
| | 44 | AS I CHANGED MY CLOTHES AND SETTLED, TOMORROW'S SCHEDULE WAS DISPLAYED. TOMORROW, THE SPECIAL CONFERENCE IS FROM 8 O'CLOCK. SCHEDULED TIME FOR LEAVING HAS ALREADY BEEN SET. | PREPARES AN ACTION PROGRAM FOR THE FOLLOWING DAY ACCORDING TO THE SCHEDULE | | |
| | 45 | IT LOOKS LIKE IT WOULD BE BETTER TO TAKE THE HOT TUB BATH AT ONCE AND GO TO SLEEP. THE ADVICE DISPLAYED IS SAYING THE SAME THING. | ADVISING TIMING FOR ACTION ACCORDING TO THE SCHEDULE AND PHYSICAL CONDITION | | |
| | 46 | WHILE TAKING THE BATH, THE BED ROOM LIGHT IS PUT OFF AND CHANGED TO A WARM-COLOR LIGHT. THE FRAGRANCE OF LAVENDER IS WAFTING THROUGH THE AIR. IT LOOKS LIKE I AM GOING TO HAVE A GOOD SLEEP. | ENVIRONMENT CONTROL ACCORDING TO THE ACTION | | |

INFORMATION DISPLAY SYSTEM

CROSS-REFERENCE TO RELATED APPLICATION

The present application is based upon and claims the benefit of priority from the prior Japanese Patent Application No.2005-111044 filed on Apr. 7, 2005; the entire contents of which are incorporated herein by reference.

BACKGROUND OF THE INVENTION

1. Field of the Invention

The present invention relates to an information display system which measures an active state of a user by a sensor which can be worn on user's body, and provides information suitable for user's situation.

2. Description of the Related Art

As a guiding information service, a system which guides flexibly a route up to a place or a spot on a way which a user wants to be guided is disclosed in Japanese Patent Application Laid-open Publication No. 2000-215211. In the system proposed in this patent document, it is possible not only to guide information of a spot, a route, and a facility etc., but also to guide practically or virtually. Moreover, in this system, it is possible to guide not only a travel to a place but also to guide with an elapsing of time.

In this case, for example, when the user makes an attempt to get on a train of a predetermined hour (clock time), when there is sufficient time, in many cases the user walks slowly to the station. Whereas, when the user makes an attempt to get a train of a predetermined hour, when there is no sufficient time, the user sometimes runs up to the station. Thus, information required by the user while walking slowly and while running differs. For example, when the user is heading for the station by walking slowly on a nice sunny day, information of "temperature and humidity on that day" is provided. Whereas, when the user is running to the station, information such as "in five minutes you will reach the station" is provided. It is desirable that this information is provided as the so called push information in which information required by the user is provided without performing intentionally an action of acquiring the required information.

Moreover, as another example, when the weather is good, while going to the station, the user sometimes wishes to walk upon selecting an aboveground route rather than an underground route. Thus, it is not possible to realize accurately the situation of the user only from information of a time and position where the user is.

SUMMARY OF THE INVENTION

According to the present invention, there can be provided an information display system which includes at least a measuring section which measures a state of each part of a body of a user, and active state identifying section which identifies an active state of the user based on a measurement result of the measuring section, an information estimating section which estimates information required by the user based on the active state identified by the active state identifying section, information storage section which stores at least the information required by the user, information selecting section which selects information from a plurality of information stored in the information storage section, the information required by the user estimated by the information estimating section, and information display section which displays the information required by the user selected by the information selecting section.

BRIEF DESCRIPTION OF THE DRAWINGS

FIG. 5 is a flow chart of an identification procedure of an active state by a clock etc;

FIG. 11 is a flow chart showing the identification procedure of the active state by a movement measuring sensor;

FIG. 15 is a flow chart showing a first estimation example of information;

FIG. 18 is a diagram showing a setting example of supplementary information;

FIG. 19 is a diagram showing the identification example of the active state by a TPO factor axis;

FIG. 20A and FIG. 20B are diagrams showing a relation of a measurement signal of a sensor and the TPO factor axis;

FIG. 21 is a diagram showing a relation of information displayed and the TPO factor axis;

FIG. 24A, FIG. 24B, FIG. 24C, and FIG. 24D are diagrams showing a first scenario of a day of a user in the second embodiment;

FIG. 25A, FIG. 25B, FIG. 25C, and FIG. 25D are diagrams showing a second scenario of the day of the user in the second embodiment;

FIG. 26A, FIG. 26B, FIG. 26C, and FIG. 26D are diagrams showing a third scenario of the day of the user in the second embodiment;

FIG. 27A, FIG. 27B, FIG. 27C, and FIG. 27D are diagrams showing a fourth scenario of the day of the user in the second embodiment;

FIG. 28A, FIG. 28B, FIG. 28C, and FIG. 28D are diagrams showing a fifth scenario of the day of the user in the second embodiment;

FIG. 29A, FIG. 29B, FIG. 29C, and FIG. 29D are diagrams showing a sixth scenario of the day of the user in the second embodiment;

FIG. 30A, FIG. 30B, FIG. 30C, and FIG. 30D are diagrams showing a seventh scenario of the day of the user in the second embodiment;

FIG. 31A, FIG. 31B, FIG. 31C, and FIG. 31D are diagrams showing an eighth scenario of the day of the user in the second embodiment;

DETAILED DESCRIPTION OF THE PREFERRED EMBODIMENTS

Embodiments of an information display system according to the present invention will be described below in detail based on diagrams. However, the present invention is not restricted to these embodiments.

First Embodiment

Figure 1:
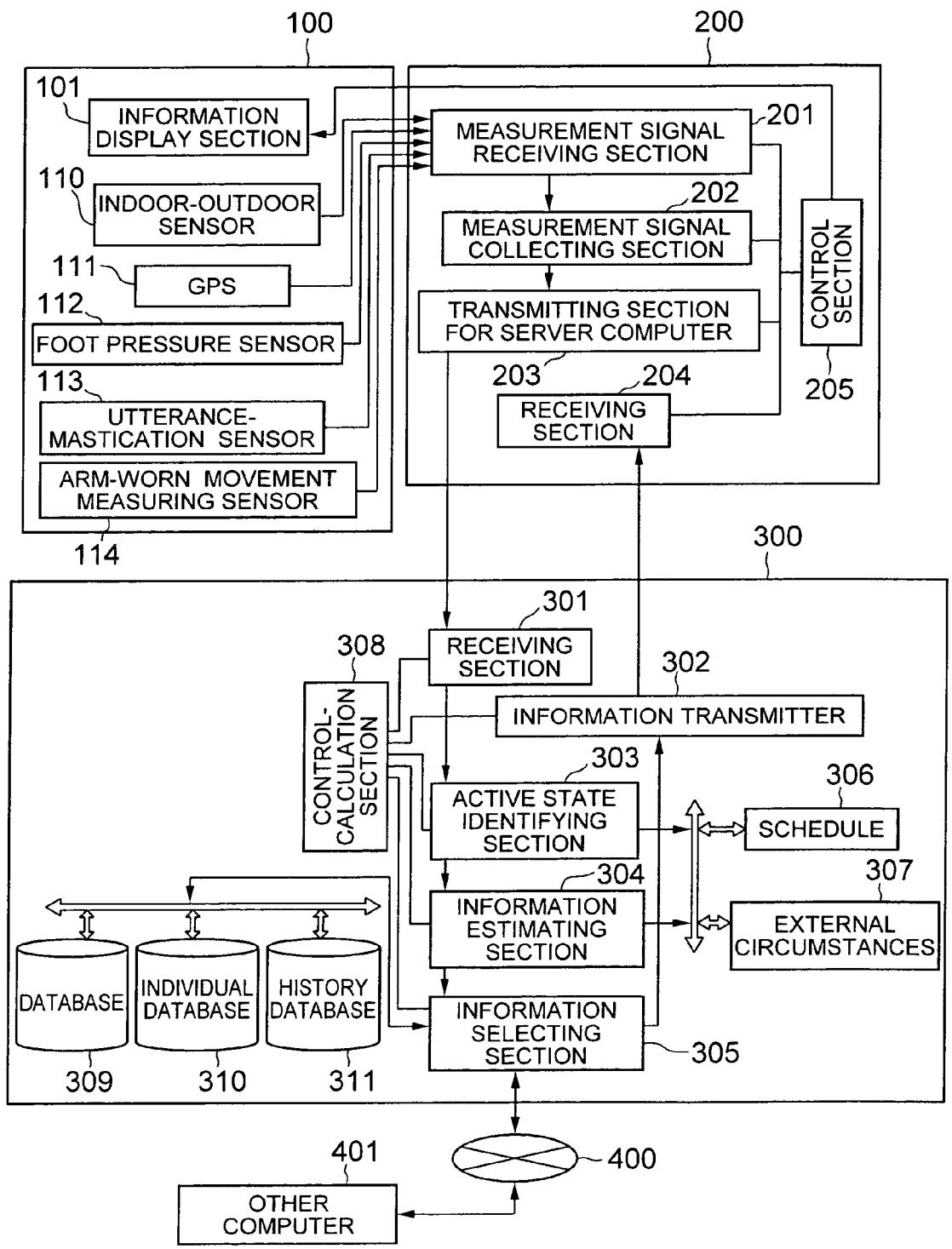
FIG. 1 is a diagram showing a functional block of an information display system according to a first embodiment.
Figure 2:
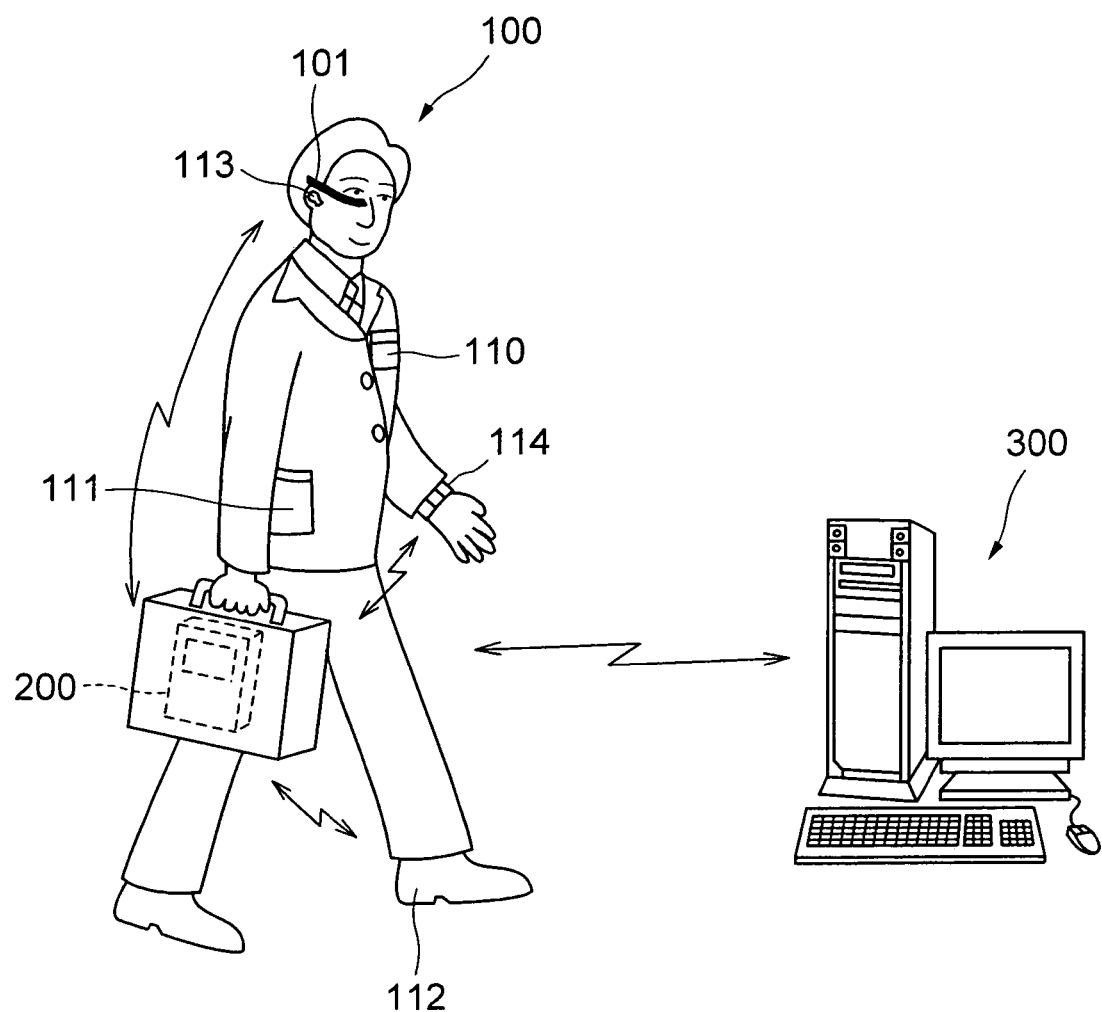
FIG. 2 is a diagram showing a schematic structure of the information display system according to the first embodiment.

FIG. 1 shows a functional block of an information display system according to a first embodiment. This information display system includes a group of various sensors worn by a user 100, a mobile gateway 200, and a server computer 300. FIG. 2 shows a schematic structure of the information display system.

First of all, a group of devices and sensors worn by the user 100 will be described. The user 100 is wearing on a body an indoor-outdoor sensor 110, a GPS (Global Positioning System) 111, a foot pressure sensor 112, an utterance-mastication sensor 113, and an arm-worn movement measuring sensor 114. Hereinafter, these sensors will be called as "sensor 110 etc". The sensor 110 etc. corresponds to a measuring means. Moreover, the user 100 wears an information display section 101 near one of eyes on head. A schematic structure and a function of the indoor-outdoor sensor 110, the GPS 111, the foot pressure sensor 112, the utterance-mastication sensor 113, and the arm-worn movement measuring sensor 114 will be described below. A detailed judging procedure of each of the sensors will be described later by using a flow chart.

(Indoor-Outdoor Sensor)

The indoor-outdoor sensor 110 performs a detection and judgment of whether the user 100 is indoors or outdoors. The indoor-outdoor sensor 110 includes an irradiating section, a receiving section, and a judging section. The irradiating section irradiates ultrasonic waves toward a reflecting object such as a ceiling. The receiving section receives ultrasonic waves reflected from the ceiling. Further, the judging section makes a judgment of whether the user 100 is indoors or outdoors based on a time required for returning of the ultrasonic waves upon being reflected, and an intensity of the reflected ultrasonic waves.

Moreover, when the user 100 uses an umbrella, the ultrasonic waves from the irradiating section are returned upon being reflected at an inner side of the umbrella which is a reflecting object. At this time, when a distance between the indoor-outdoor sensor 110 and the reflecting object is not more 40 cm for example, a judgment that the reflecting object is not a ceiling is made. Furthermore, by adjusting a sampling time and a storage time of the receiving section, a judgment result can be further optimized.

Moreover, the indoor-outdoor sensor 110 is not restricted to the ultrasonic waves, and may be a sensor which uses the following methods.

(1) Active optical method of irradiating beam of laser or of an infrared region and detecting reflection of the irradiated beam (application of a common distance sensor), (2) Passive ultraviolet rays method of detecting light of an ultraviolet region (making use of a fact that an amount of ultraviolet rays differs for indoor and outdoor)

(3) Passive infrared rays method of measuring a space temperature in an upper direction (amount of infrared rays from clouds etc.) by a pyroelectric sensor (making use of a fact that a temperature differs in the ceiling and the sky), and (4) Passive noise method of measuring a noise by a microphone (making use of a fact that a noise spectrum pattern differs for indoor and outdoor).

(GPS)

The user 100 wears the GPS 111 on the body. By the GPS 111, the whereabouts and a direction of the user 100 can be detected. Moreover, instead of the GPS 111, a position information service of a portable telephone can be used. The GPS corresponds to a position measuring means.

(Foot Pressure Sensor)

The foot pressure sensor 112 detects a pressure distribution of a sole of shoes worn by the user 100. Further, the foot pressure sensor 112 identifies a standing state, a sitting state, and a walking state of the user 100. The walking state includes a state of walking, a state of walking fast, a state of running with short steps such as jogging or tripping, and a state of running.

(Utterance-Mastication Sensor)

The utterance-mastication sensor 113 identifies whether the user 100 is in a state of uttering (talking) or in a state of masticating (chewing), in other words, the utterance-mastication sensor 113 identifies whether the user 100 is having a meal. The utterance-mastication sensor 113 is an earphone-type sensor worn on one of the ears of the user 100. Inside a casing of the earphone-type sensor, a bone conduction microphone and an external sound microphone are integrated.

The bone conduction microphone detects an internal body sound. The internal body sound is generated inside of the body during conversation and mastication, and is vibrations propagated in the body. Concrete examples of the internal body sound are vocal cord vibrations, a sound of biting food by teeth, a sound of food passing through the throat, and a sound of moving a jaw joint.

The external sound microphone detects an external sound of an environment of the user 100. The external sound includes in addition to a noise in the environment, vibrations propagated to the outside of the body according to utterance of the user 100, in other words, voice. Further, the utterance-mastication sensor 113, based on a detection result of the bone conduction microphone and the external sound microphone, identifies whether the user 100 is in the state of utterance or in the state of mastication according to the judging procedure which will be described later.

(Arm-Worn Movement Measuring Sensor)

The arm-worn movement measuring sensor 114 (hereinafter called as "movement measuring sensor") detects movement of an arm of the user 100. The movement measuring sensor 114 includes an acceleration sensor and an angular velocity sensor. Further, the movement measuring sensor 114 can identify further accurately daily actions and the walking state of the user 100 coordinating with a detection result of the foot pressure sensor described above. Examples of a method of wearing on the arm are such as a wrist watch type or affixing on the arm.

(Information Display Section)

The user 100 wears on the head the information display section 101 which displays information which will be described later. The information display section 101 is a light portable display unit to be worn on the head. The information display section 101 is structured such that with this information display section 101 worn by the user 100, a display section (not shown in the diagram) of a size not larger than few millimeters is positioned in front of one of the eyes of the user 100. The size of the display section is smaller than a size of a pupil of the user 100. Therefore, a proportion of an area occupied by the display section with respect to a region of field of view of the user 100 is substantially small. Accordingly, the user 100 perceives information from a normal field of view, as well as can perceive information displayed on the display section according to the requirement. In other words, the information display section 101 can be used with a sense of using as the so called see-through viewer. Moreover, hereinafter, the "information display section" will be called as "MEG" (Mobile Eye Glass).

Figure 3:
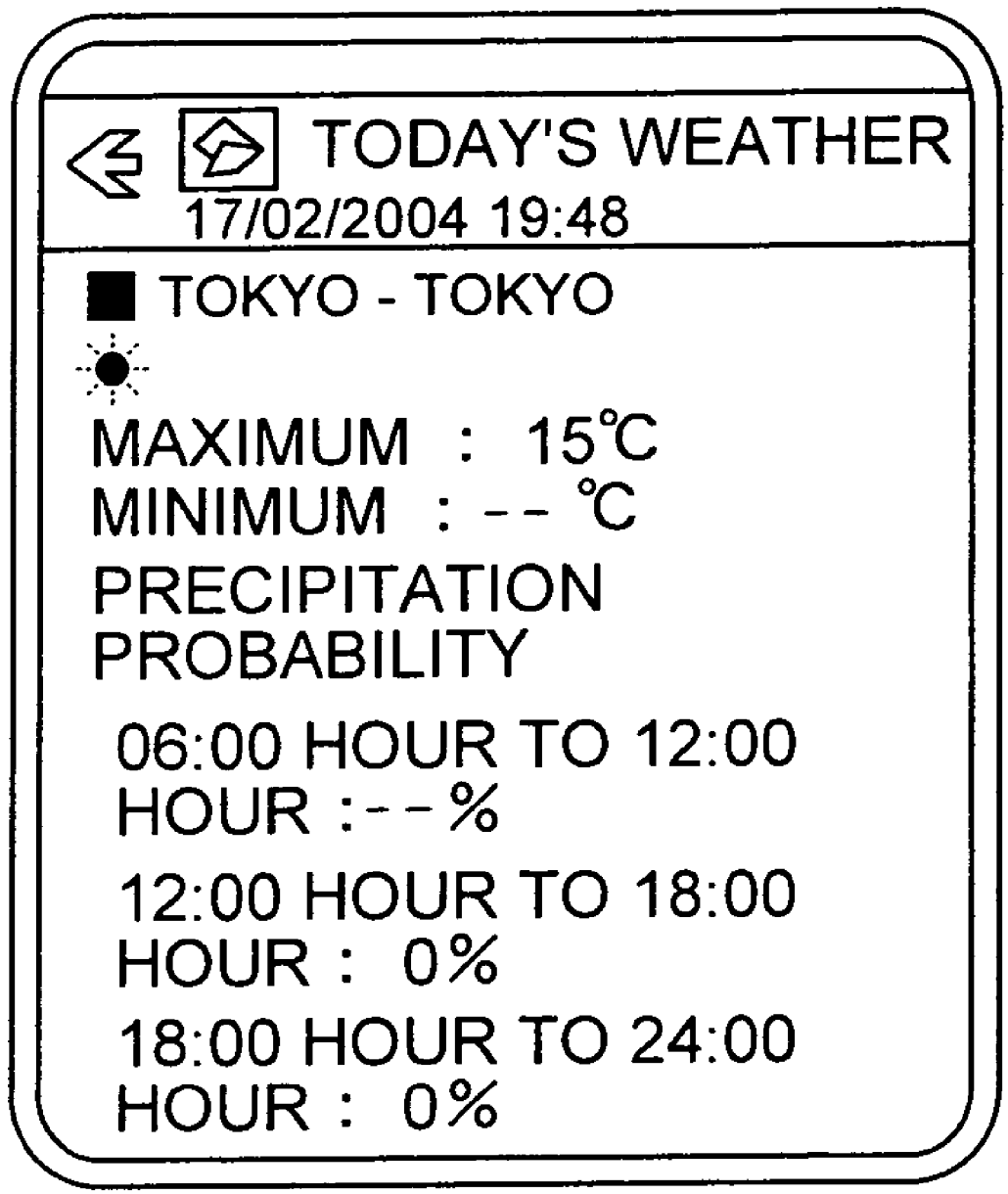
FIG. 3 is a diagram showing an example of information displayed.

FIG. 3 shows an example of information displayed on the display section of the information display section 101. The user 100, when walking outdoors, can perceive information such as a temperature of that day and a probability of precipitation. Such weather information is the so called push information which is information displayed upon being selected according to a procedure which will be described later. As a result, the user is not required to acquire the weather information intentionally. In other words, the user without performing a troublesome operation each time can acquire at any time the required information according to the circumstances.

Moreover, a Bluetooth chip (not shown in the diagram) for wireless communication is installed in each of the information display section 101, the indoor-outdoor sensor 110, the GPS 111, the foot pressure sensor 112, the utterance-mastication sensor 113, and the arm-worn movement measuring sensor 114. Further, measurement signals of the sensor 110 etc. are transmitted to the mobile gateway 200.

(Mobile Gateway)

The mobile gateway 200 will be described. The mobile gateway 200 has three functions. The first function is to collect information from each type of sensor from the sensor group described above. The second function is to perform communication with the server 300 which will be described later. The third function is to perform communication with the information display section 101. Further, the gateway 200 is accommodated for example, in shoes worn by the user 100.

In FIG. 1, a measurement signal receiving section 201 of the mobile gateway 200 includes a wireless tag (Bluetooth chip) which is a receiving section. The measurement signal receiving section 201 receives measurement signals from the indoor-outdoor sensor 110, the GPS 111, the foot pressure sensor 112, the utterance-mastication sensor 113, and the arm-worn movement measuring sensor 114 described above. The measurement signal collecting section 202 collects a plurality of measurement signals from these sensors as one signal. A transmitting section for server computer 203 transmits the collected measurement signal to the server computer 300. A receiving section 204 receives a signal from the server computer 300 which will be described later. Moreover, a control section 205, a CPU for example, controls the measurement signal receiving section 201, the measurement signal collecting section 202, the transmitting section for server computer 203, and the receiving section 204.

(Server Computer)

The server computer 300 will be described. The server computer 300 is installed at a position different than the position of the user 100. A receiving section 301 of the server computer 300 receives a measurement signal transmitted from the transmitting section for server computer 203 of the mobile gateway 200. An active state identifying section 303 identifies an active state of the user 100 based on the measurement signal received. An information estimating section 304 estimates the information required by the user 100 based on the active state identified by the active state identifying section 303.

The active state identifying section 303 and the information estimating section 304 refer to a schedule 306 and an external circumstances 307 respectively. The schedule 306 has a schedule of the user 100 stored therein. Moreover, the external circumstances 307 includes weather information and information of traffic jam.

A database 309, an individual database 310, and a history database 311 store the information required by the user 100 or information which becomes criteria when selecting information in an information selecting section 305. The individual database 310 stores information such as objects of hobby, preference, and interest, and action target (improvement in lifestyle habits and diet). The user 100 inputs information in the individual database 310. Moreover, the history database 311 stores information such as a place where the user 100 was on the previous day and actions on the previous day. Details of the information stored by a group of these databases will be described later. Moreover, a structure is not restricted to a structure in which the database group is integrated in the server computer 300. For example, a structure may be such that the database group is provided outside away from the server computer 300. The database 309, the individual database 310, and the history database 311 correspond to an information storage means.

Further, the information selecting section 305 selects the information required by the user 100 which is estimated by the information estimating section 304 from a plurality of information stored in the database 309, the individual database 310, and the history database 311 or from other computer based on this information. In this case, the information selecting section 305 is structured to enable communication with other computer 401 via a dedicated line or the Internet 400. Accordingly, the information selecting section 305 can acquire the information required by the user 100 via the other computer 401. Moreover, the information selecting section 305 can also acquire information from information-service vender (information-service provider company) via the Internet 400.

The information selecting section 305 uses metadata when selecting the information required by the user 100. The metadata means data in which contents about data are described. The metadata is created for helping to search target data from enormous data. For example, when the information selecting section 305 selects "news" information, if in the individual database, "sports" is registered as an object of interest of the user 100, the information selecting section 305 searches news to which metadata called sports is assigned, and selects such news on priority basis. Accordingly, it is possible to select exactly (filtering) data most suitable for the user 100 from information estimated to be desired by the user 100.

Moreover, a control-calculation section 308 performs optimization of information to be displayed for information which is selected by the information selecting section 305. In this case, when detail character information is displayed by using the information display section 101, sometimes contrarily the perception of information by the user 100 becomes difficult. Therefore, information to be displayed on the information display section 101 is abbreviated to brief information simplified by the optimization of information to be displayed.

The information transmitting section 302 transmits the information selected by the information selecting section 305 to the mobile gateway 200. Moreover, the control-calculation section 308 controls the receiving section 301, the information transmitting section 302, the active-state identifying section 303, the information estimating section 304, and the information selecting section 305.

In this case, the mobile gateway 200 has for example a mobile communication card installed therein, and is connected to the server computer 300 via the Internet. However, by using a high performance mobile PC (personal computer), it is also possible to integrate the mobile gateway 200 and the server computer 300 to one mobile PC. Moreover, for reducing an amount of communication data between each sensor and the mobile gateway 200, it is possible to structure such that from the foot pressure sensor 112 for example, by pre-processing, only a result in which an action state of a foot is identified is transmitted rather than transmitting the measurement data. Or, for reducing the amount of communication data between the mobile gateway 200 and the server computer 300, it is possible to structure such that a similar pre-processing is performed in the measurement signal collecting section 202.

Figure 4:
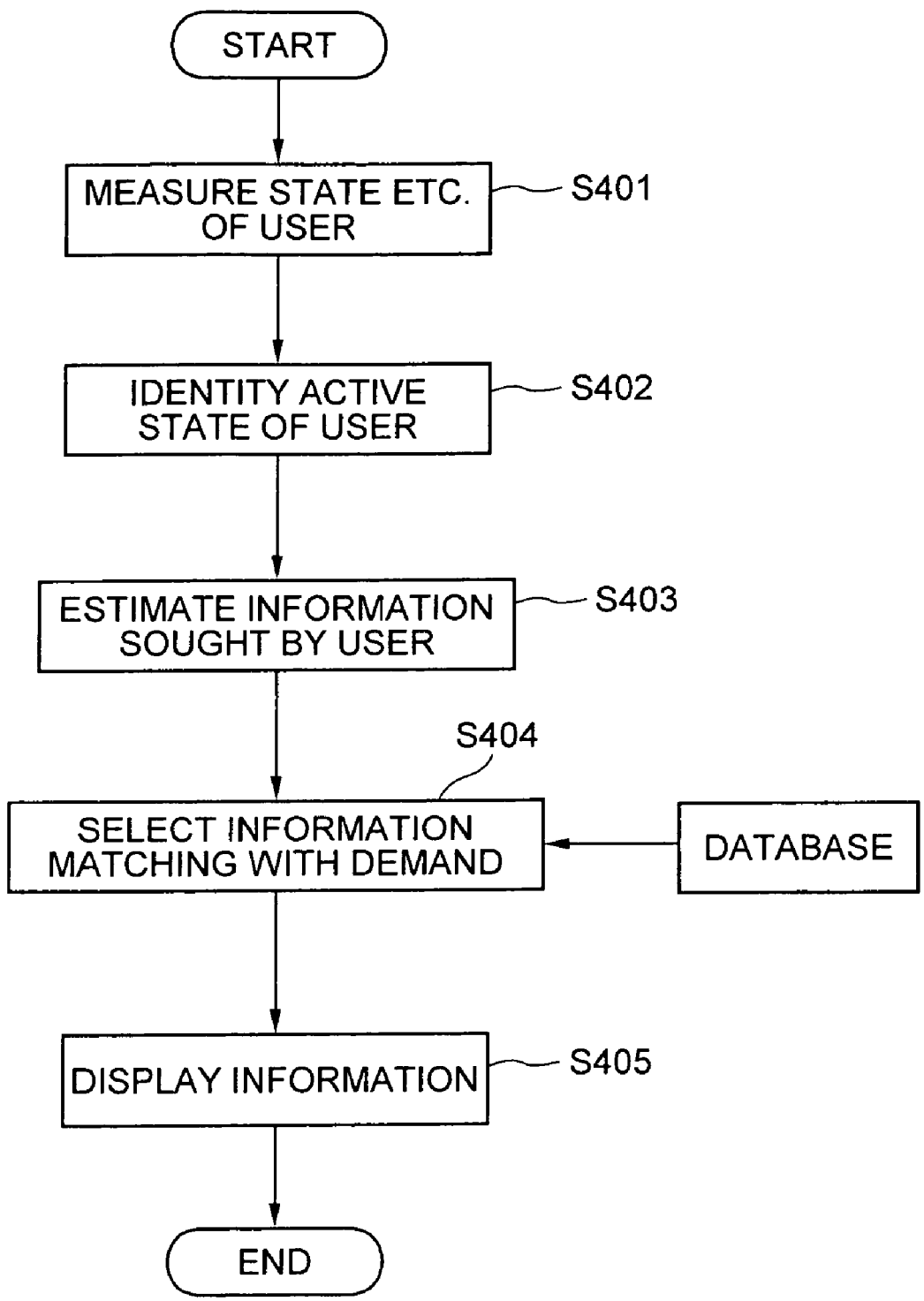
FIG. 4 is a flow chart showing processing procedure of the information display system according to the first embodiment.

FIG. 4 is a flow chart showing roughly a procedure of displaying information by the information display system. First of all, at step S401, the indoor-outdoor sensor 110, the GPS 111, the foot pressure sensor 112, the utterance-mastication sensor 113, and the arm-worn movement measuring sensor 114 measures a respective state of the body of the user 100.

At step S402, the active state identifying section 303 identifies an active state of the user 100 based on the measurement signal from the sensor 110 etc. At step S403, the information estimating section 304 refers to the active state which is identified and the schedule 306 for example, and estimates information that is thought to be sought by the user. At step S404, the information selecting section 305 selects information matching with the requirement sought by the user 100 from the database. At step S405, the information display section 101 displays the information which is selected.

Next, the procedure shown in the flow chart described above will be described in detail by using a concrete example.

(Function of Active State Identifying Section)

FIG. 5 is a flow chart showing a procedure of identifying the active state by the active state identifying section 303 by referring to the schedule 306 or information of elapsed time. Hereinafter, an item scheduled by the user 100 will be called as "event". Examples of an event are "meeting at "T" university" and "social gathering at GINZA hall".

At step S501, an action schedule of the user 100 is stored in the schedule 306. The schedule 306 can be stored in a memory (not shown in the diagram) in the server computer 300. At step S502, for example, the control-calculation section 308 of the server computer 300 creates a sub-schedule of further detailed contents based on the schedule 306.

Figure 6A:
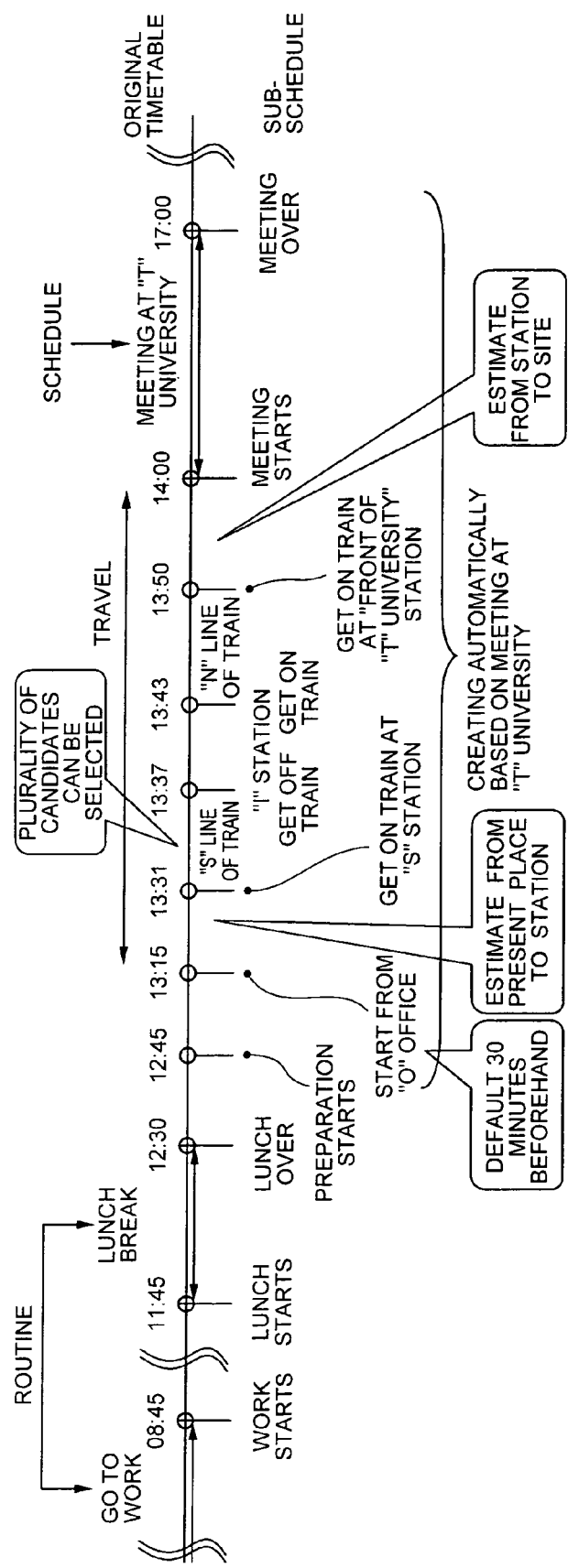
FIG. 6A and FIG. 6B are diagrams showing a schedule and a sub-schedule created from the schedule.
Figure 6B:
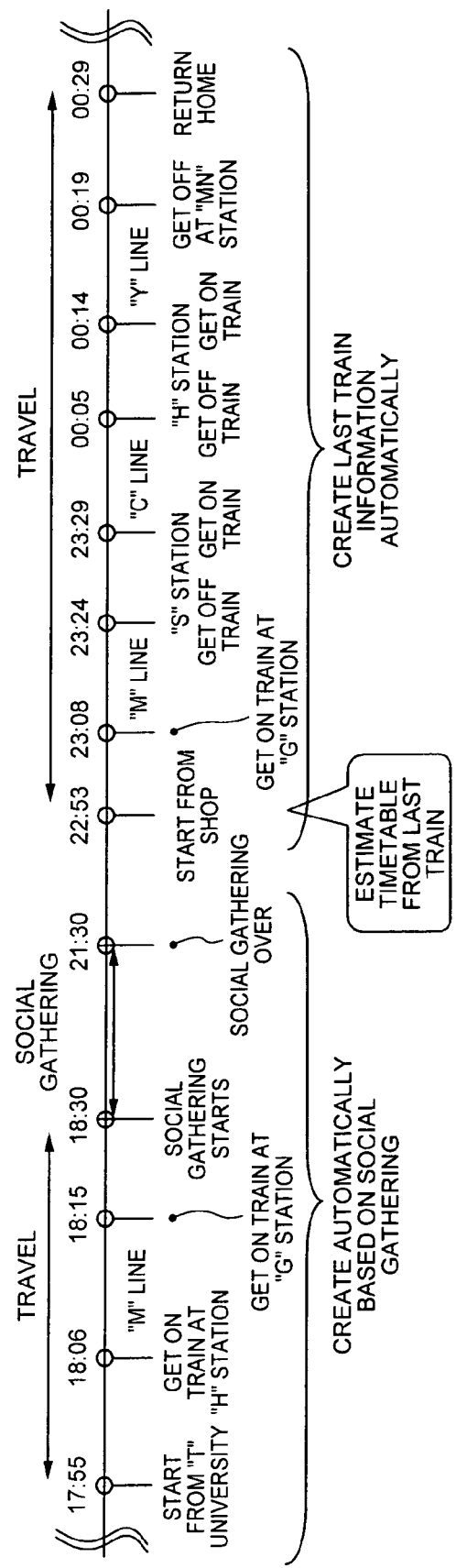

FIG. 6A and FIG. 6B show an example of a structure of the sub-schedule created. In a schedule for a certain day of the user 100, the following events (1), (2), and (3) are input beforehand.
(1) In the morning: go to an office of "O" company (hereinafter, called as "O" office)
(2) 14:00 hour~17:00 hour: meeting at "T" university,
(3) 18:30 hour~21:00 hour: social gathering at GINZA hall In this case, the nearest station from "O" office where the user 100 works is "S" station. Moreover, for attending the meeting scheduled in the afternoon at "T" university it is necessary to go up to "front of "T" university" station. The control-calculation section 308 has a plurality of routes for going from "S" station to "front of "T" university" station as candidates. The user 100 can select any route from the plurality of routes, but based on the information stored in the individual database 310, for example, according to a preference of the user 100, a route with the shortest time, a route with the lowest fare, a route with the shortest walking distance, and a route with the least transfers can be selectively set to be candidates. In this sub-schedule, a route used by transferring "S" line and "N" line of train is selected.

With a time of start of the meeting at "T" university (14:00 hour) as a basis, the control-calculation section 308 creates automatically a sub-schedule by estimating a time of starting preparation for leaving "O" office, a travel time up to "S" station, a travel time by train, and a travel time from "front of "T" university station" to a place of meeting.

Furthermore, the control-calculation section 308 creates automatically a sub-schedule from an end of the meeting at "T" university to an end of the social gathering. Accordingly, the user 100, based on a schedule (timetable) created in the sub-schedule, realizes that it is better to go from "front of "T" university" station" to "G" station by using "M" line.

Similarly, the control-calculation section 308 creates automatically a sub-schedule from a venue where the social gathering is held to home of the user 100. Accordingly, the user 100 can return home assuredly by the last train to "MN" station which is the nearest station from the home of the user 100.

The description will be continued upon coming back to FIG. 5. At step S504, a present time is acquired by a clock. The clock may be any one of worn by the user 100, being integrated in the mobile gateway 200, and being integrated in the server computer 300.

At step S503, based on the hour acquired, a judgment of whether it is Tmin before an event starting hour or not is made. The event starting hour Tmin can be set beforehand by the user 100 or can be set by memorizing an action of the user 100 by the control-calculation section 308. When a judgment result at step S503 is No, a judgment of step S503 is repeated. When the judgment result at step S503 is Yes, at step S505, the user 100 is identified to be at least in a preparation state of the event, and the process is advanced to step S507.

At step S507, based on a time acquired at step S506, a judgment of whether it is an event starting time or not is made. When a judgment result at step S507 is No, step S507 is repeated. When the judgment result at step S507 is Yes, at step S508, the user 100 is identified to be at least in an event starting state, and the process is advanced to step S510.

At step S510, based on the active state identified of the user 100 at step S509 based on the measurement result from the sensor 110 etc. mentioned above, a judgment of whether the event is started or not is made. When a judgment result at step S510 is No, the process is advanced to step S511. At step S511, a judgment of whether the schedule is changed or not is made. When a result at step S511 is Yes, at step S512, the event is identified to have been cancelled. When the judgment result at step S510 is Yes, at step S513, the user 100 is identified to be at least in an implementation state of the event, and the process is advanced to step S515.

At step S515, a judgment of whether the event is over or not is made based on the active state of the user 100 which is identified at step S514 based on the measurement result from the abovementioned sensor 110 etc. When a judgment result at step S515 is No, step S515 is repeated. When the judgment result at step S515 is Yes, at step S516, the user 100 is identified to be at least in a completion state of the event.

The event in the present flow chart is not restricted to be a single item. It is also possible to take states of a plurality of events having different contents at the same time. An example is a case in which event A is in an implementation state and even B is in a preparation state at the same time.

Based on the procedure shown in FIG. 5 mentioned above, the active state identifying section 303, based on the clock or the schedule 306, can identify an active state such as "event preparation state", an "event starting state", an "event cancellation state", an "event implementation state", and an "event completion state".

(Distinction of Position State by Indoor-Outdoor Sensor and GPS)

Figure 7:
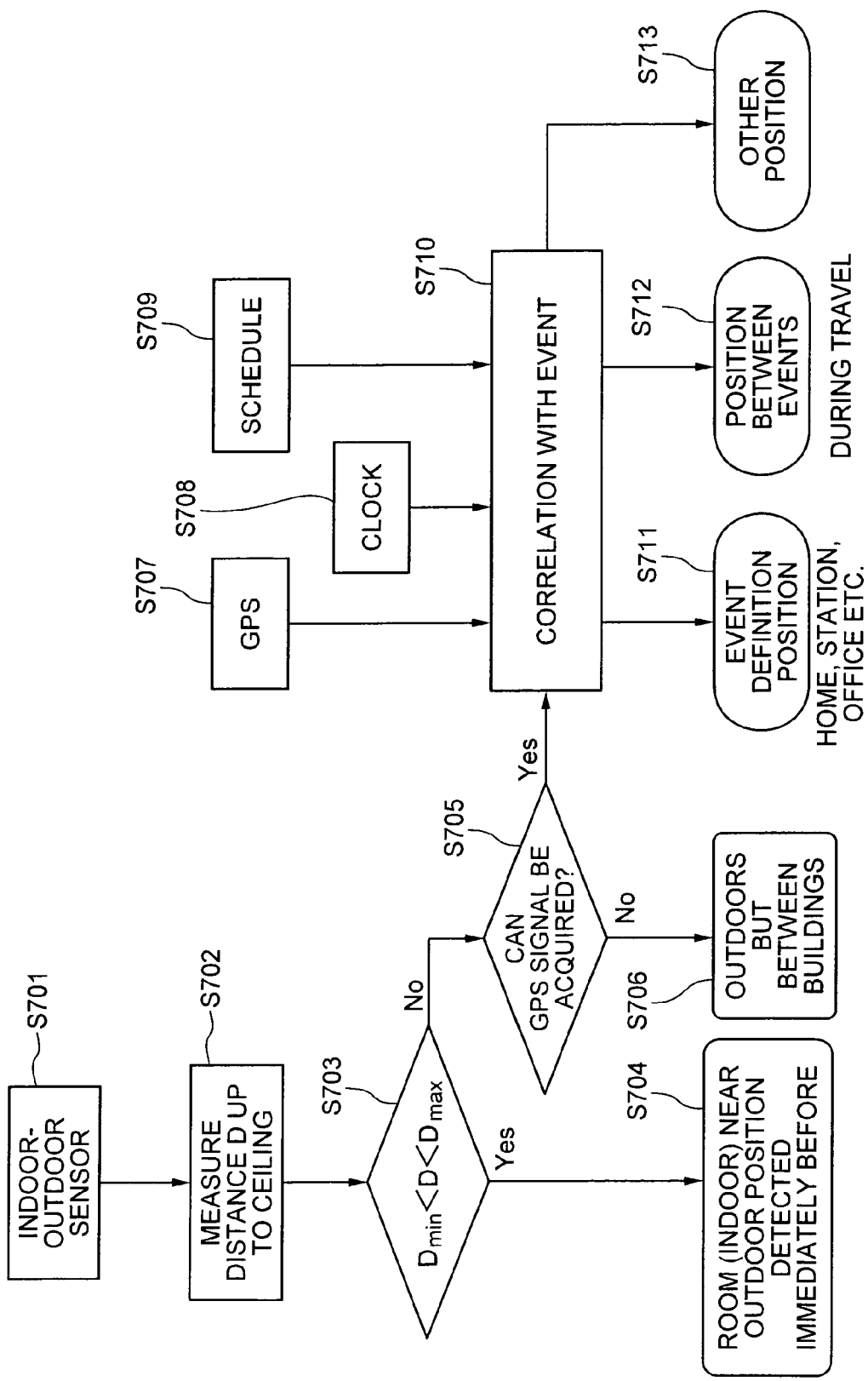
FIG. 7 is a flow chart showing the identification procedure of the active state by a GPS etc.

Next, based on FIG. 7, a procedure of identifying the active state of the user 100 by the active state identifying section 303 based on measurement signals from the indoor-outdoor sensor 110 and the GPS 111 will be described below. At step S701, the user 100 wears the indoor-outdoor sensor 110. At step S702, a distance D up to a ceiling at a position where the user 100 is, is measured by the indoor-outdoor sensor 110.

At step S703, a judgment of whether a relation $$Dmin<D<Dmax$$

is satisfied or not is made. Here, Dmin and Dmax are threshold values for distinguishing the ceiling. When a height above the floor level of the indoor-outdoor sensor 110 is about 120 cm (assuming that an adult user has kept the indoor-outdoor sensor 110 in a chest pocket), Dmin is about 70 cm (obstacle such as an umbrella) and Dmax is about 280 cm (height of a ceiling of a supermarket is about 3 meters to 4 meters). When a judgment result at step S703 is Yes, at step S704, the user is identified to be indoors near an outdoor position detected immediately before, and the process is advanced to step S705. However, when the user is identified to be using a means of transportation based on the schedule 306, thereafter, even if an outdoor state is detected continuously, the user 100 is identified to be traveling according to the schedule 306 or the sub-schedule mentioned above.

At step S705, a judgment of whether the measurement signal from the GPS 111 is acquired or not is made. When a judgment result at step S705 is No, at step S706 the user 100 is identified to be outdoors and in an environment such as between buildings where the GPS 111 cannot be used.

When the judgment result at step S705 is Yes, the process is advanced to step 710. At step S710, a correlation of as to how the present position is related to a nearby event definition position is checked by referring to the measurement signal from the GPS 111 at step S707, information of elapsed time by a clock at step S708, and the schedule 306 and the sub-schedule at step S709.

According to a correlation result at step S710, a judgment of the user 100 being at the event definition position (step S711), being at a position between the events (step S712), or being at some other position at step S713) is made. The event definition position at step S711 means for example home, station, and office etc., and when the present position is between the event definition position "office" immediately before and the event definition position "station" immediately after, at step S712, the user 100 is identified to be at a position between the events, and it is realized that the user 100 is traveling between the event definition positions.

(Foot Pressure Sensor)

The foot pressure sensor 112, as shown in FIG. 2 is provided for example in an interior of shoes worn by the user 100. The foot pressure sensor 112 is structured to detect a pressure of at least a heel portion. Moreover, the detection accuracy can be further improved by detecting a pressure of a planta (plantar, sole of foot) in addition to the heel portion. Moreover, a structure can be such that the foot pressure sensor 112 is formed in the shoes, or affixed to the planta of the user 100.

Figure 8:
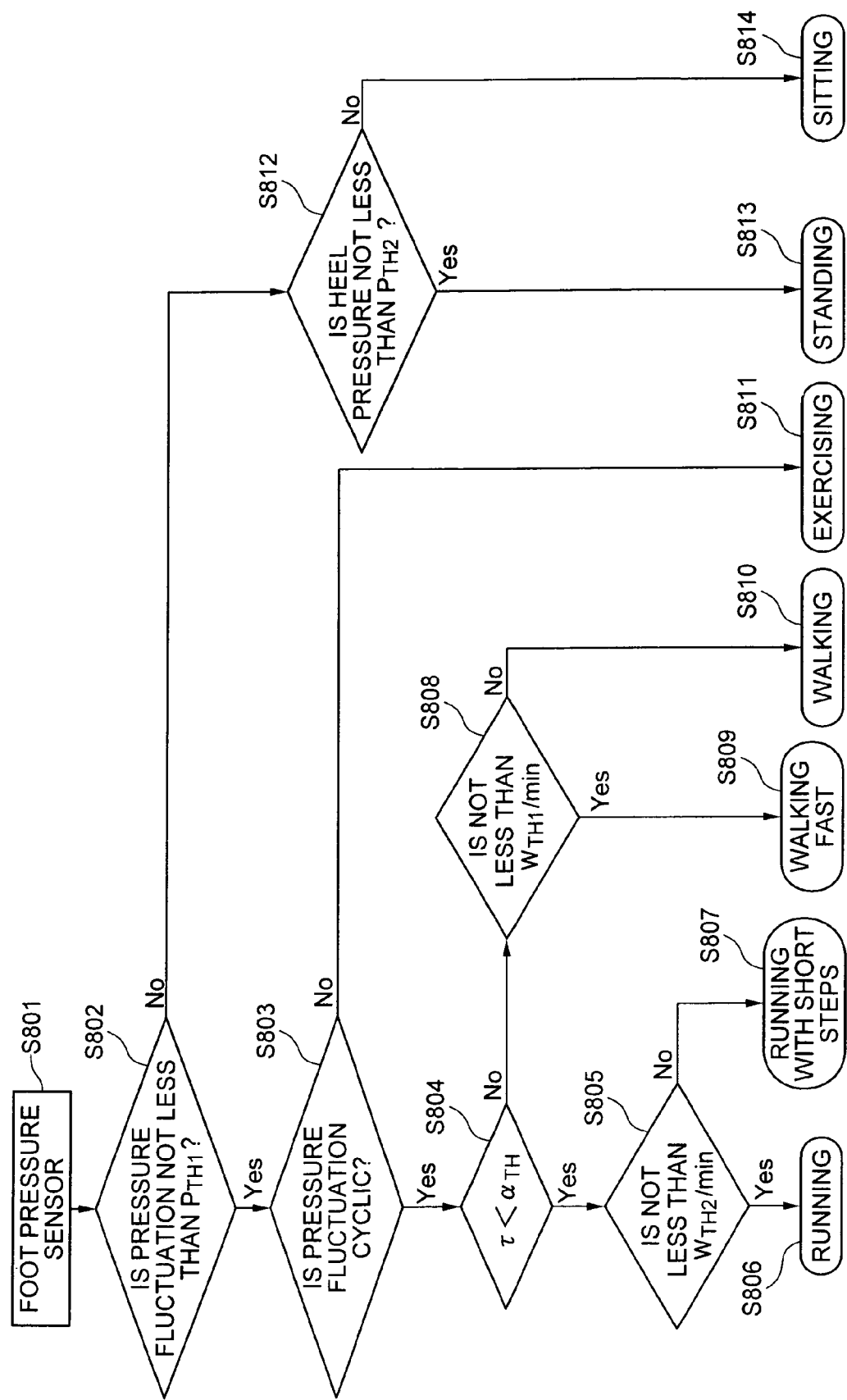
FIG. 8 is a flow chart of the identification procedure of the active state by a foot pressure sensor.

FIG. 8 is a flow chart showing a procedure for identifying the active state by the foot pressure sensor 112. At step S801, the user 100 wears shoes having the foot pressure sensor 112 integrated therein. At step S802, a judgment of whether a pressure fluctuation is not less than $P_{TH1}$ or less than $P_{TH1}$ is made. Here, $P_{TH1}$ is a pressure fluctuation threshold value for distinguishing traveling. When a judgment result at step 802 is Yes, the process is advanced to step S803. At step S803, a judgment of whether the pressure fluctuation is cyclic or not is made. When a judgment result at step S803 is Yes, the process is advanced to step S804.

At step S804, a judgment of whether a relation $\tau<\alpha_{TH}$ is satisfied or not is made. Here, $\tau$ denotes a proportion of time for which pressure is exerted on the heel in one cycle and $\alpha_{TH}$ denotes a duty threshold value for distinguishing walking and running. The duty threshold value $\alpha_{TH}$ varies from person to person, and is roughly 30% to 40%.

When a judgment result at step S804 is Yes, at step S805, a judgment of whether not less than $W_{TH2}$/min or less than $W_{TH2}$/min is made. Here, $W_{TH2}$/min is a threshold value of number of steps in one minute.

When a judgment result at step S805 is Yes, at step S806, the user 100 is identified to be in a running state. Moreover, when the result at step S805 is No, at step S807, the user 100 is identified to be in a state of running with short steps.

When a result at step S802 is No, the process is advanced to step S812. At step S812, a judgment of whether a pressure of the heel is not less than $P_{TH2}$ or less than $P_{TH2}$ is made. Here, $P_{TH2}$ is a pressure threshold value for distinguishing sitting and standing, and is set according to a body weight of the user 100.

When a judgment result at step S812 is Yes, at step S813, the user 100 is identified to be in a standing state. Moreover, when the judgment result at step S812 is No, at step S814, the user 100 is identified to be in a sitting state.

Furthermore, when the judgment result at step S803 is No, at step S811, the user 100 is identified to be in an exercising state. Moreover, when the judgment result at step S804 is No, the process is advanced to step S808. At step S808, a judgment of whether it is $W_{TH1}$/min or not is made. $W_{TH1}$/min is a threshold value of number of steps in one minute.

When a judgment result at step S808 is Yes, at step S809, the user 100 is identified to be in a fast walking state. Moreover, when the judgment result at step S808 is No, at step S810, the user 100 is identified to be in the walking state.

Each of the abovementioned threshold values $P_{TH1}$, $P_{TH2}$, $\alpha_{TH}$, $W_{TH1}$, and $W_{TH2}$ can be set according to the user 100 or can be set by memorizing the action of the user 100 by the learning function. Thus, as described above, based on the measurement signal of the foot pressure sensor 112, the active state of the user such as the "running state", the "running with short steps state", the "fast walking state", the "walking state", the "exercising state", the "standing state", and the "sitting state" can be identified.

(Utterance-Mastication Sensor)

Figure 9:
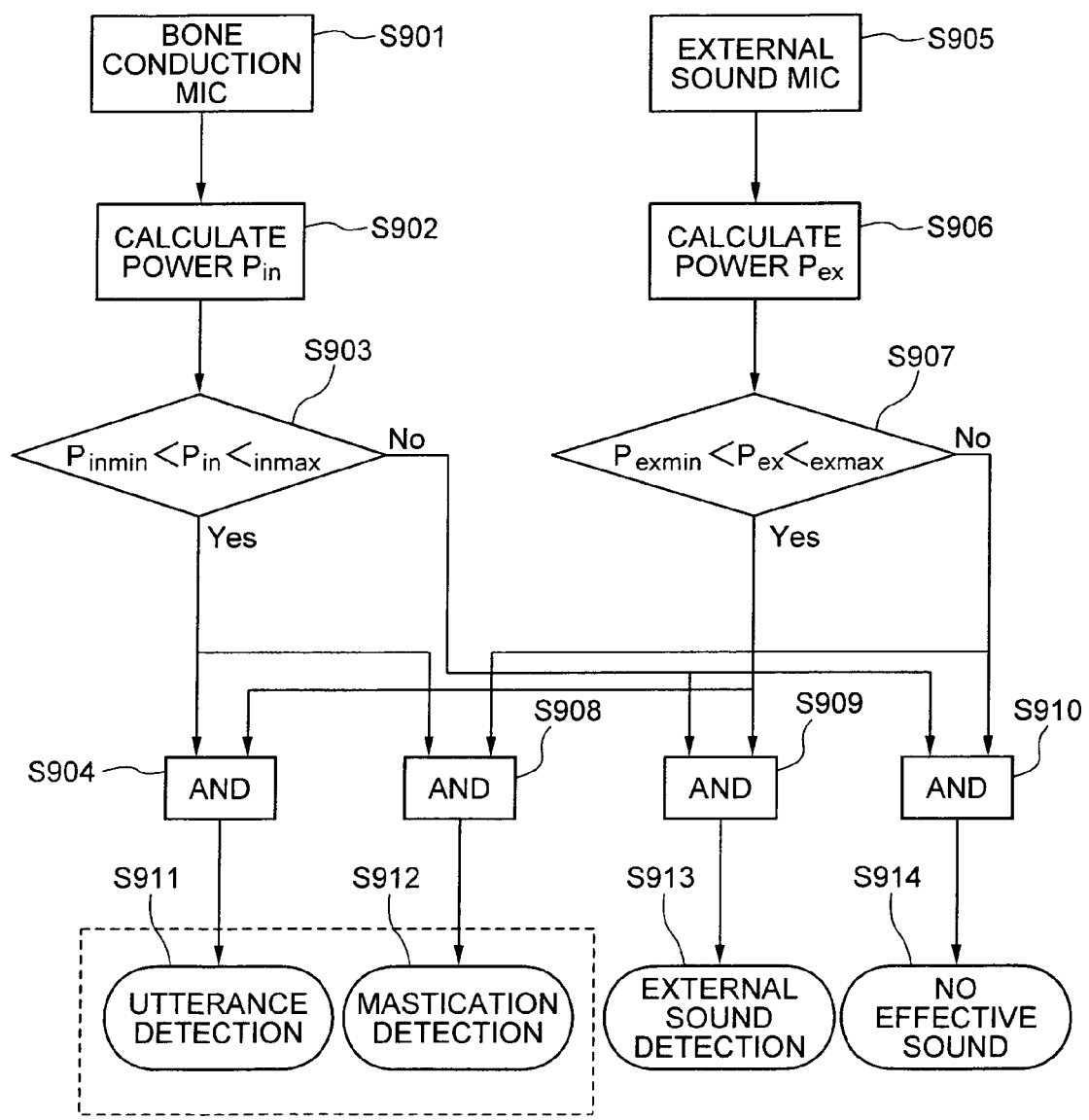
FIG. 9 is a flow chart showing the identification procedure of the active state by an utterance-mastication sensor.

FIG. 9 is a flow chart of a procedure for identifying the active state by the utterance-mastication sensor 113. The utterance-mastication sensor 113 is an earphone type sensor which includes the bone conduction microphone and the external sound microphone. First of all, at step S901, a measurement signal is acquired from the bone conduction microphone. At step S902, a power Pin of the signal from the bone conduction microphone is calculated. The power Pin is a power of bone conduction sound in a unit time.

At step S903, a judgment of whether a relation

Pin min<Pin<Pin max is satisfied or not is made. Here Pin min and Pin max are threshold values of the bone conduction sound power for eliminating noise. Pin min is set to cut off background noise when there is no mastication and utterance, and Pin max is set to cut off loud noise such as when the bone conduction microphone is touched. When a judgment result at step S903 is Yes, the process is advanced to step S904 and step S908. Moreover, when the judgment result at step S903 is No, the process is advanced to step S909 and step S910.

On the other hand, at step S905, a measurement signal from the external sound microphone is acquired. At step S906, power Pex of the signal from the external sound microphone is calculated. Power Pex is an external sound power in a unit time.

At step S907, a judgment of whether a relation

Pex min<Pex<Pex max is satisfied or not is made. Here Pex min and Pex max are threshold values of the external sound power for eliminating noise. Pex min is set to cut off background noise when there is no mastication and utterance, and Pex max is set to cut off loud noise such as when the bone conduction microphone is touched. When a judgment result at step S907 is Yes, the process is advanced to step S904 and step S909. Moreover, when the judgment result at step S907 is No, the process is advanced to step S908 and step S910.

At step S904, the judgment result at step S903 (Yes) and the judgment result at step S907 (Yes) are acquired. Further, at step S911, the user 100 is identified to be in an uttering state.

At step S908, the judgment result at step S903 (Yes) and the judgment result at step S907 (No) are acquired. Further, at step S912, the user 100 is identified to be in a masticating state.

At step S909, the judgment result at step S903 (No) and the judgment result at step S907 (Yes) are acquired. Further, at step S913, a state in which the external sound is detected is identified.

At step S910, the judgment result at step S903 (No) and the judgment result at step S907 (No) are acquired. Further, at step S914, a state in which an effective sound is detected is identified.

Figure 10:
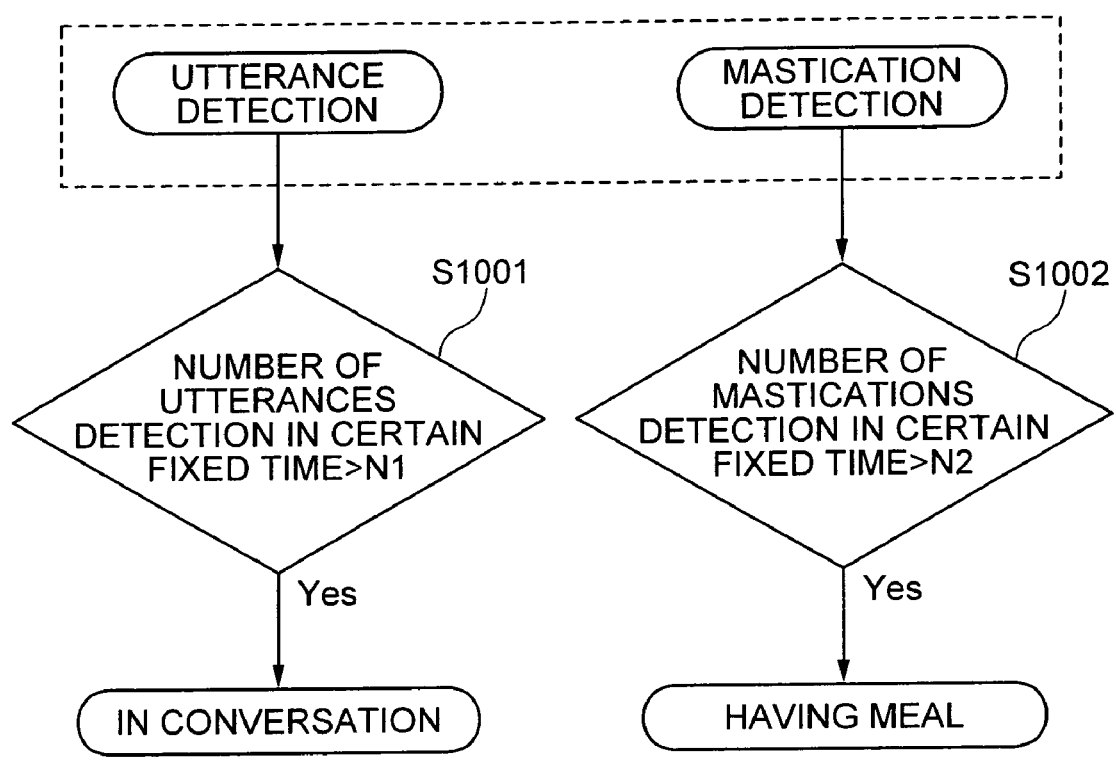
FIG. 10 is another flow chart of the identification procedure of the active state by the utterance-mastication sensor.

FIG. 10 is a flowchart showing a procedure for identifying a conversation state and a meal state based on the results achieved in the procedure shown in FIG. 9. When at step S911 in FIG. 9, the user 100 is in the uttering state, the process is advanced further to step S1001. At step S1001, a judgment of whether number of utterances detected in a fixed time>N1 or not is made. Here, N1 is a threshold value of number of utterances detected for distinguishing the conversation. When a judgment result at step S1001 is Yes, the user 100 is identified to be in conversation. For example, when an attempt is made to perform a process of detecting eight utterances every second, when utterances not less than 120 times in 60 seconds (corresponding to 15 seconds) are detected, the user is identified to be in conversation. Moreover, it is not shown in the diagram, but when the judgment result at step S1001 is No, although the utterance is detected, the user 100 is identified to be not having a conversation.

Moreover, when the user 100 is in the masticating state at step S912 in FIG. 9, the process is advanced further to step S1002. At step S1002, a judgment of whether number of mastications detected in a fixed time>N2 or not is made. Here, N2 is threshold value of number of mastications for distinguishing the meal. When a judgment result at step S1002 is Yes, the user 100 is identified to be having a meal. For example, when an attempt is made to perform a process of detecting eight mastications every second, when mastications not less than 120 times in 60 seconds (corresponding to 15 seconds) are detected, the user 100 is identified to be having a meal. Moreover, it is not shown in the diagram, but when the judgment result at step S1002 is Yes, although the mastication is detected, the user 100 is identified to be in a state of not having a meal.

(Arm-Worn Movement Measuring Sensor)

As shown in FIG. 2, the user 100 wears the movement measuring sensor 114 on an arm. Further, as mentioned above, the movement measuring sensor 114 includes the acceleration sensor and the angular velocity sensor. FIG. 11 is a flow chart showing a procedure for identifying the active state by the movement measuring sensor 114.

At step S1101, the user 100 wears the movement measuring sensor 114 on the arm. At step S1102, a judgment of whether an acceleration is not less than $A_{TH1}$ or less than $A_{TH1}$ is made. $A_{TH1}$ is an acceleration threshold value for distinguishing shaking of arm. When a judgment result at step S1102 is Yes, the process is advanced to step S1103. At step S1103, a judgment of whether a fluctuation in the acceleration is cyclic or not is made. When a judgment result at step S1103 is Yes, the process is advanced to step S1104. At step S1104, a judgment of whether $A_P>A_{TH2}$ or not is made. Here, $A_P$ denotes a peak value of acceleration in one cycle and $A_{TH2}$ denotes a peak value for distinguishing walking and running.

When a judgment result at step S1104 is Yes, the process is advanced to step S1105. At step S1105, a judgment of whether $W \geq W_{TH2}$ or not is made. W is number of steps per unit time and $W_{TH2}$ is a threshold value of number of steps per unit time for distinguishing "running" and "running with short steps". When a judgment result at step S1105 is Yes, at step S1106, the user is identified to be in the running state. When the judgment result at step 1105 is No, at step S1107, the user 100 is detected to be in the running with short steps state.

Moreover, when the judgment result at step S1102 is No, at step S1112, the user 100 is identified to have no arm movement. When the judgment result at step S1103 is No, at step S1111, the user 100 is identified to have an arm movement. For example, the user 100 is in a state such as a state of doing some work having to move a hand, a state of having a meal, and a state of having a conversation with gestures.

When the judgment result at step S1104 is No, the process is advanced to step S1108. At step S1108, a judgment of whether $W \geq W_{TH1}$ or not is made. W is number of steps per unit time and $W_{TH1}$ is a threshold value of number of steps per unit time for distinguishing "fast walking" and "normal walking". When a judgment result at step S1108 is Yes, at step S109, the user 100 is identified to be in the fast walking state. Moreover, when the judgment result at step S1108 is No, at step S1110, the user 1000 is identified to be in the walking state.

Each of the abovementioned threshold values $A_{TH1}$, $A_{TH2}$, $W_{TH1}$, and $W_{TH2}$ can be set according to the user 100 or can be set memorizing the action of the user by the learning function. Thus, as described above, based on the measurement signal of the movement measuring sensor 114, the active state of the user 100 such as the "running state", the "running with short steps state", the "fast walking state", the "walking state", the "arm movement state", and the "no arm movement state" can be identified.

In the abovementioned flow charts in FIG. 7 to FIG. 11, an active state which can be identified according to each of the sensor 110 etc. is described. Here, as shown in FIG. 2, the user 100 has worn a plurality of sensors 110 etc. Therefore, the active state identifying sensor 303 identifies the active state based on the plurality of measuring signals collected at the measurement signal collecting section 202. Example of identifying the active state of the user 100 based on the measurement signals from the plurality of sensors 110 etc. will be described below by using FIG. 12A, FIG. 12B, FIG. 13A, FIG. 13B, FIG. 14A, and FIG. 14B.

Figure 12A:
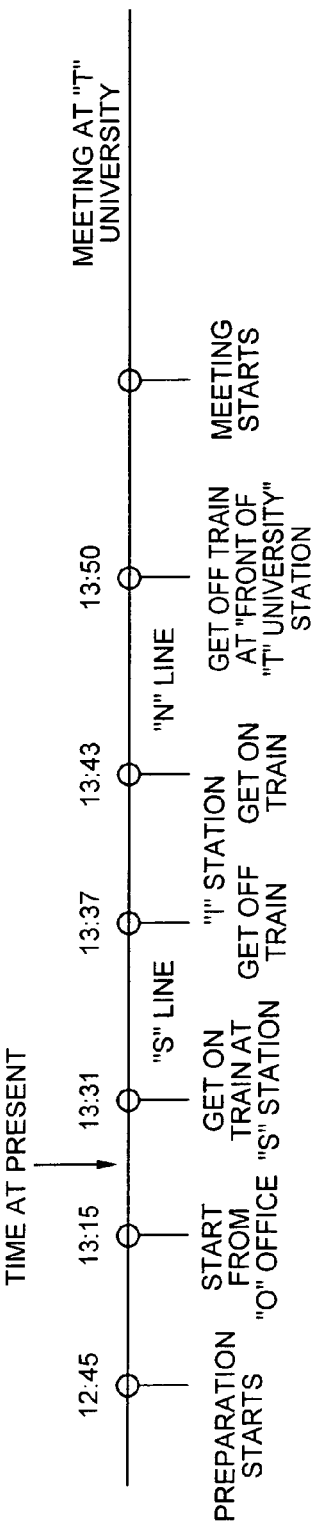
FIG. 12A and FIG. 12B are flow charts showing a first identification example of the active state.

FIG. 12A shows a portion from leaving "O" office up to starting the meeting at "T" university from the schedule and sub-schedule of the user 100. In this case, at the present time 13:20 hour, a state in which the user travels by running with short steps from "O" office toward "S" station is considered.

Figure 12B:
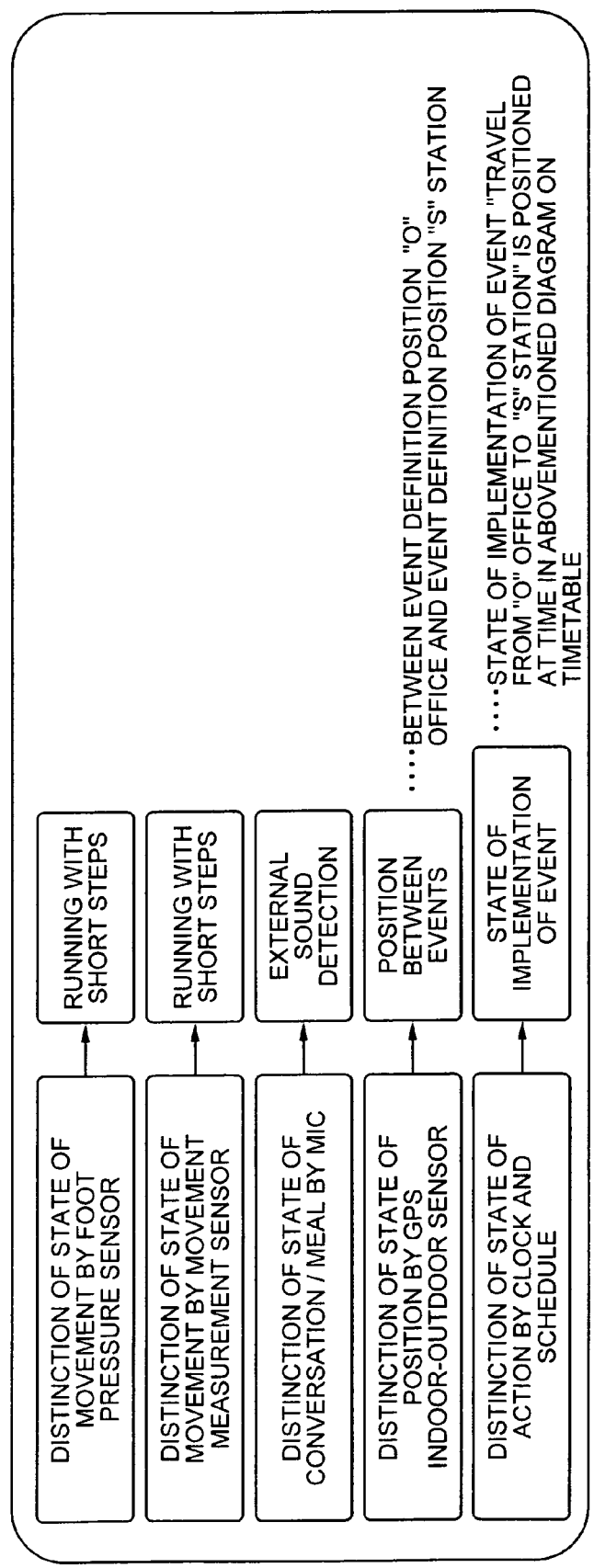

FIG. 12B shows identification result of the active state based on the sensors 110 etc. at this time. Based on the measurement signal from the foot step sensor 112, the user 100 is identified to be in the state of "running with short steps". Based on the measurement signal from the movement measuring sensor 114, the user 100 is identified to be in the state of "running with short steps". Based on the measurement signal from the utterance-mastication sensor 113, the state of "external sound detection" is identified. Based on the measurement signal from the GPS 111 and the indoor-outdoor sensor 110, the user 100 is identified to be in the state of "position between events", such as a state in which the user 100 is between "S" station and "O" office which are event definition positions. Moreover, based on the clock and the schedule 360, the user 100 is identified to be in the state of "event implementation", such as a state of implementation of an event "travel from "O" office to "S" station".

The active state identifying section 303, based on the identification result of each of the abovementioned states, identifies that the user 100 is in a state of "running with short steps from "O" office to "S" station".

Figure 13A:
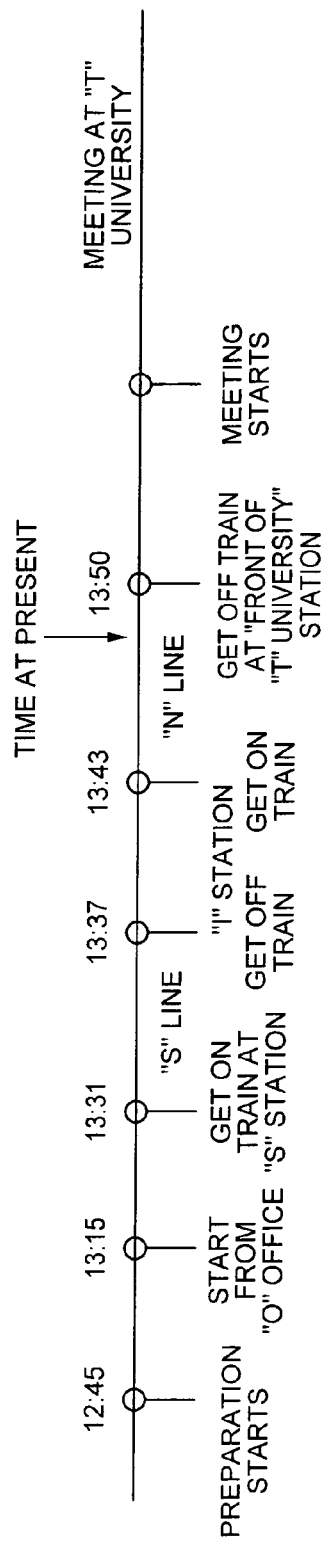
FIG. 13 is a flow chart showing a second identification example of the active state.

FIG. 13A shows a portion from leaving "O" office up to starting the meeting at "T" university from the schedule and the sub-schedule of the user 100. In this case, at the present time 13:40 hour, a state in which the user 100 talks with a colleague in a train is considered.

Figure 13B:
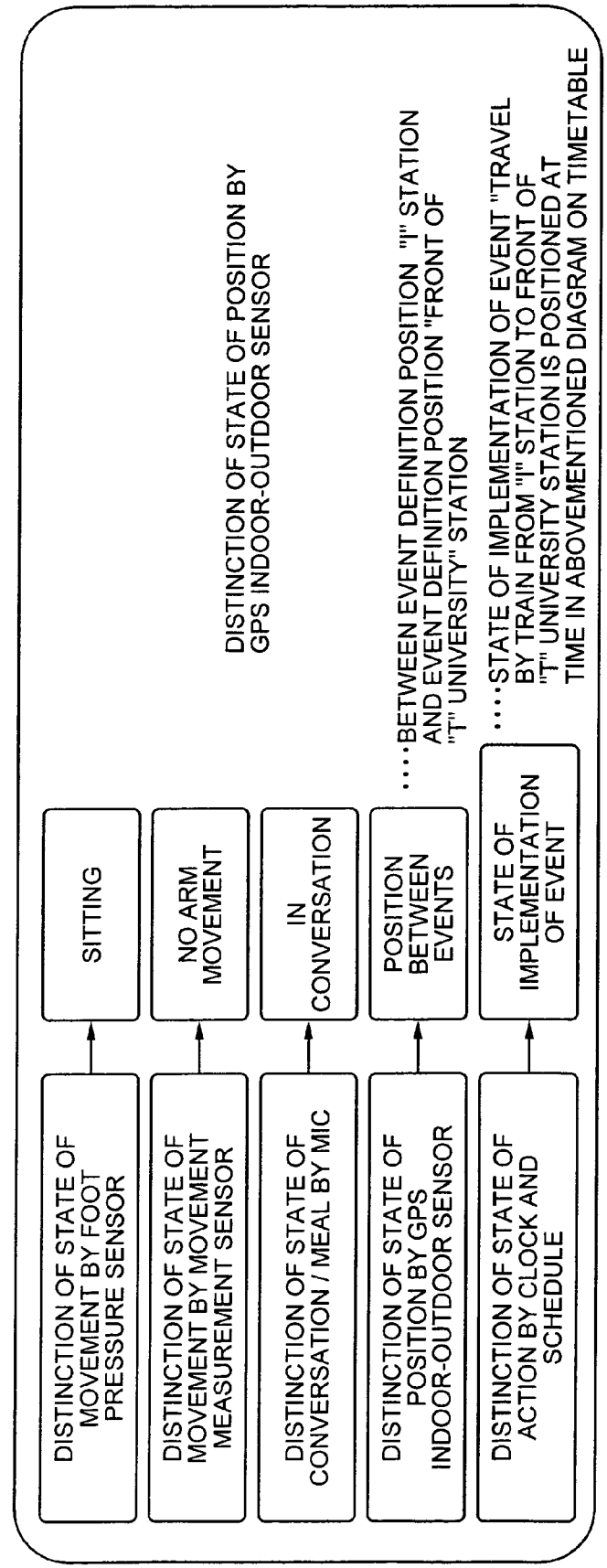

FIG. 13B shows identification result of the active state based on the sensors 110 etc. at this time. Based on the measurement signal from the foot step sensor 112, the user 100 is identified to be in the state of "sitting". Based on the measurement signal from the movement measuring sensor 114, the user 100 is identified to be in the state of "no arm movement". Based on the measurement signal from the utterance-mastication sensor 113, the user is identified to be in the state of "in conversation". Based on the measurement signal from the GPS 111 and the indoor-outdoor sensor 110, the user 100 is identified to be in the state of "position between events", such as a state in which the user 100 is between "T" station and "front of "T" university" station which are event definition positions. Moreover, based on the clock and the schedule 360, the user 100 is identified to be in the state of "event implementation", such as a state of implementation of an event "train travel from "T" station to "front of "T" university" station".

The active state identifying section 303, based on the identification result of each of the abovementioned states, identifies that the user 100 is in a state of "traveling from "T" station to "front of "T" university" station and having a conversation sitting in a seat". Moreover, when an arm movement is detected, the user 100 is identified to be in a state of having a conversation enthusiastically with gestures.

Figure 14A:
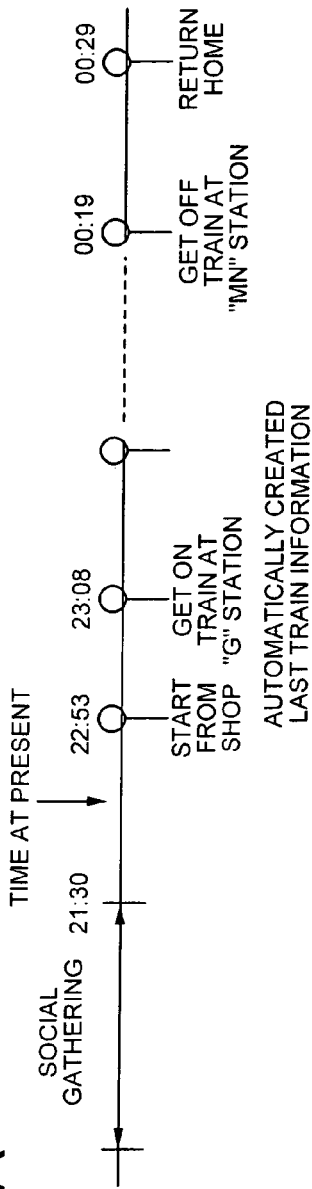
FIG. 14 is a flowchart showing a third identification example of the active state.

FIG. 14A shows a portion from end of the social gathering up to starting travel for returning home from the schedule and the sub-schedule of the user 100. In this case, at the present time 22:00 hour, a state in which the social gathering extended beyond the schedule time is over and the user 100 came out from a shop while talking is considered.

Figure 14B:
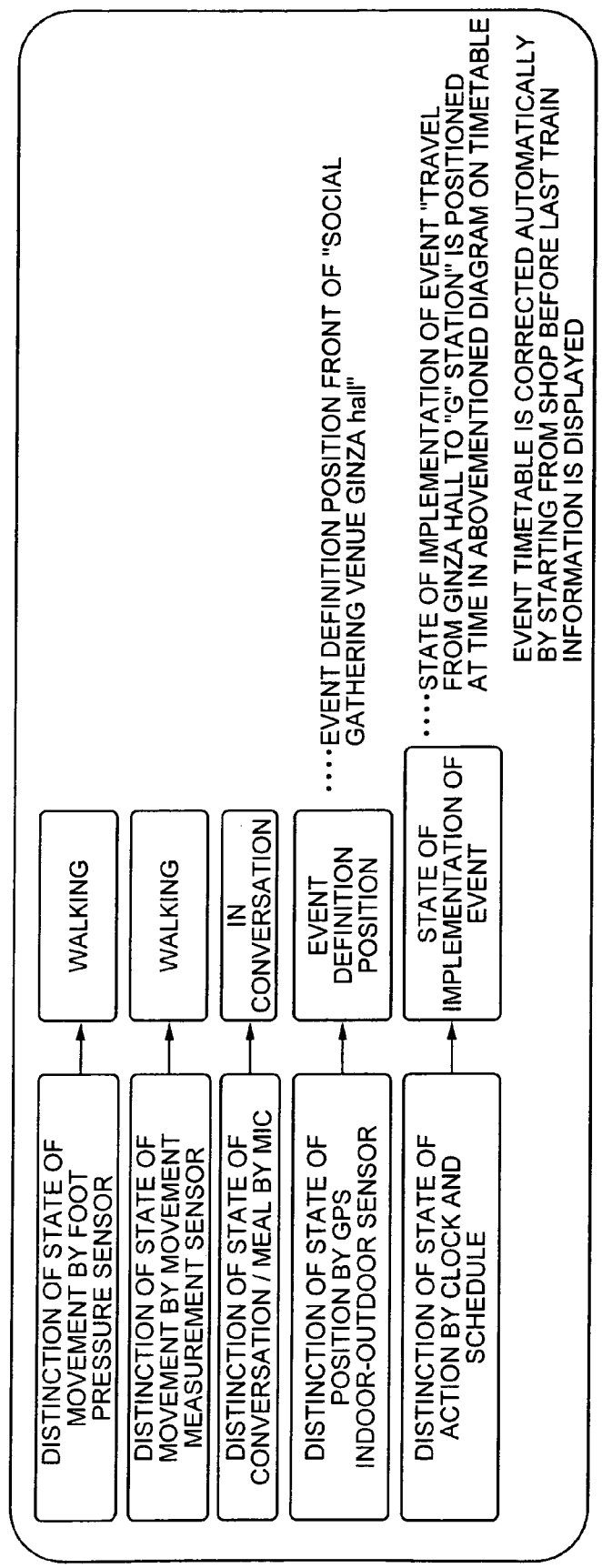

FIG. 14B shows identification result of the active state based on the sensors 110 etc. at this time. Based on the measurement signal from the foot step sensor 112, the user 100 is identified to be in the state of "walking". Based on the measurement signal from the movement measuring sensor 114, the user 100 is identified to be in the state of "walking". Based on the measurement signal from the utterance-mastication sensor 113, the user 100 is identified to be in the state of "in conversation". Based on the measurement signal from the GPS 111 and the indoor-outdoor sensor 110, the user is identified to be in the state of "event definition position", such as a state in which the user is in front of the "social gathering venue at GINZA hall" which is an event definition position. Moreover, based on the clock and the schedule 360, the user 100 is identified to be in the state of "event implementation", such as a state of implementation of an event "travel by walking from GINZA hall to "G" station". The active state identifying section 303, based on the identification result of each state, identifies that the user 100 "has left the social gathering venue and has started walking while talking".

In this case, in the sub-schedule which is created beforehand, since a schedule of returning home was not registered, as shown in FIG. 6A and FIG. 6B, an arrangement is made to create automatically a sub-schedule of returning home by the last train, and to be able to inform the latest time at which the user 100 has to leave the shop. On the other hand, as it is described here, the user 100 may also leave the shop for returning home by a train earlier than the last train. In this case, the start of travel of the user 100 being detected, the control-calculation section 308 of the server computer 300 corrects automatically an event time associated with returning home in the sub-schedule.

(Estimation and Selection of Information)

Next, concrete examples of a procedure for estimating, selecting, and displaying information required by the user 100 will be described by referring to FIG. 15, FIG. 16, and FIG. 17. FIG. 15 is a flow chart showing a procedure of a first example of estimating and selecting information. At step S1501, the active state identifying section 303 identifies the present active state of the user 100. For example, in the first example, a state in which the user 100 acting according to the schedule similar to the case in FIG. 12 is traveling by running with short steps from "O" office toward "S" station at the present time 13:20 hour is considered.

At step S1502, the active state identifying section 303 extracts an associated event at the present time from the schedule and the sub-schedule. For example, the active state identifying section 303 extracts an event "travel by walking from "O" office to "S" station" as an event in the implementation state, and extracts an event "travel by train from "S" station to "T" station" as an event in the preparation state.

Thus, at the present time, sometimes a plurality of associated events is extracted. Moreover, since as to how much in advance to enter into the preparation state of an event, varies according to the content of the event and an individual, as to how much in advance to enter into the preparation state of an event is let to be set beforehand.

At step S1503, the information estimating section 304 estimates information associated with the extracted event required by the user 100 (hereinafter called as "supplementary information"). In this case, estimation is made by using a supplementary information database such as a database in FIG. 18A and FIG. 18B in which supplementary information which is estimated based on an event and a state of the event is registered beforehand. Details of the supplementary information will be described later. For example, supplementary information in an implementation state of "travel by walking from "O" office to "S" station" includes information such as "route information", "scheduled time of arrival", "difference from expected time of arrival". In this case, for example, for places frequently visited such as home and office, normally, the route information being unnecessary, the route information can be set to be not displayed when deemed appropriate. Moreover, supplementary information in the preparation state of "travel by train from "S" station to "I" station" is "transfer information (station of getting on the train/station of getting off the train, departure time/arrival time, time required, and fare", and "train service information".

The information selecting section 305, at step S1504, estimates an expected time of arrival of the user 100 at "S" station. Moreover, the present time is obtained from the clock. The present position is obtained from the GPS 111. The walking speed is determined from a change in a position in a unit time or a walking state obtained from the foot pressure sensor 112 and the movement measuring sensor 114 etc.

Furthermore, the information selecting section 305 searches transfer information of "S" line toward "I" station at a time at which the user 100 can get on the train. The search of transfer information is performed by referring to the database 309 in the server computer 300 and the other computer via the Internet 400. Moreover, the information selecting section 305 further searches service information of the route such as "in normal service at present" and "delayed by ten minutes due to a car breakdown".

Moreover, as shown in FIG. 1, the information searched and selected (hereinafter called as "information provided") is transmitted to the information transmitting section 302 of the server computer 300. The receiving section 204 of the mobile gateway 200 receives the information provided which is transmitted from the server computer 300. Further, at step S1505, the information display section 101 displays the information provided. Accordingly, while walking toward "S" station, the user 100 can obtain station information of a train to get on at "S" station. Thus, the user 100 need not search by himself or herself intentionally the timetable and the transfer information of the train required by checking his or her schedule from then onward.

Figure 16:
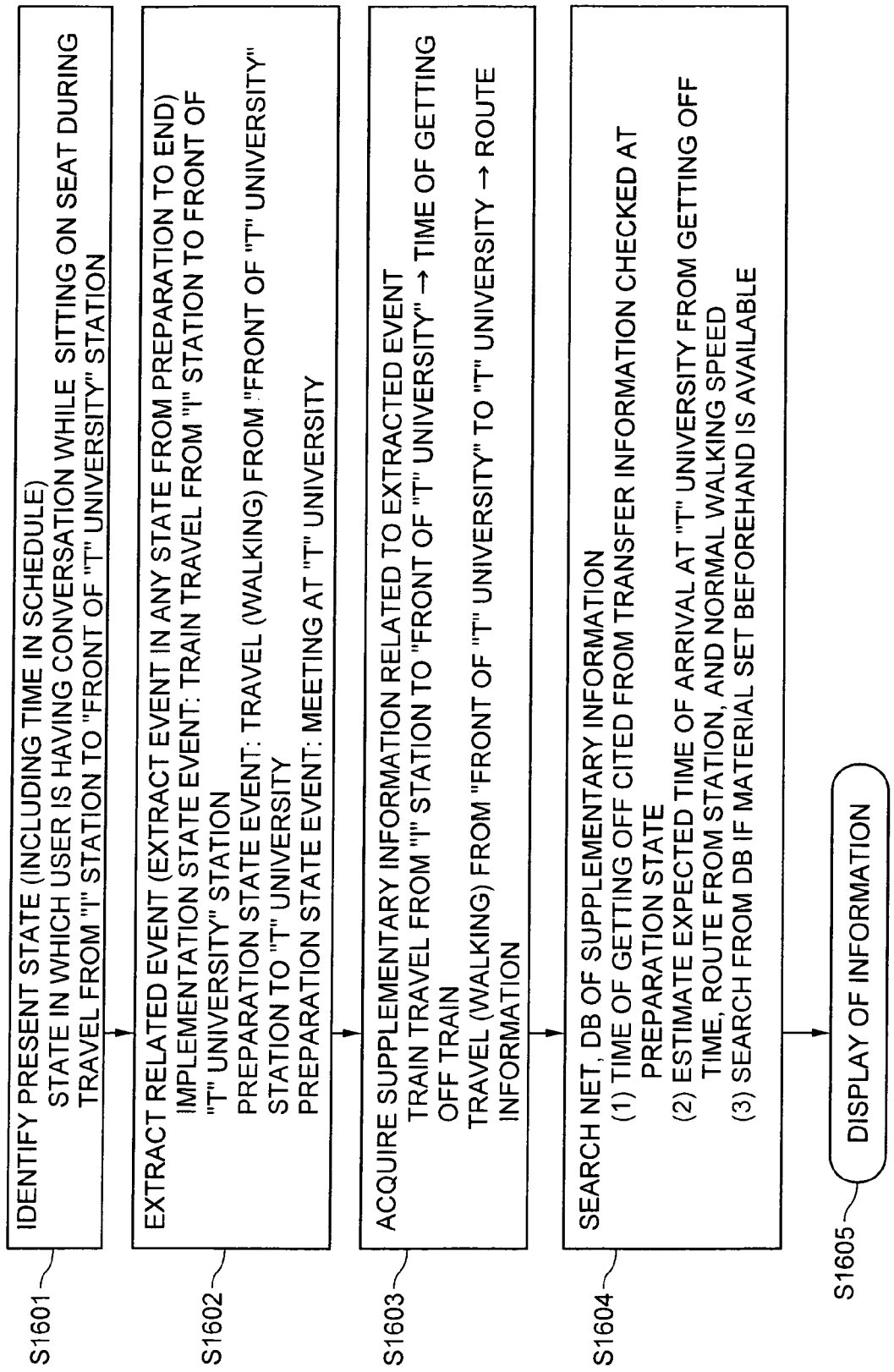
FIG. 16 is a flow chart showing a second estimation example of information.

FIG. 16 is a flow chart showing a procedure of a first example of estimating and selecting information required by the user 100. At step S1601, the active state identifying section 303 identifies the present state of the user 100. For example, in the second example, a state in which the user 100 acting according to a schedule similar to the case in FIG. 13 travels from "I" station to front of "T" university station, and while sitting and having a conversation at the present time 13:40 hour is considered.

At step S1602, the active state identifying section 303 extracts an associated event at the present time from the schedule and the sub-schedule. For example, the active state identifying section 303 extracts an event "travel by train from "I" station to front of "T" university station" as an event in the implementation state, and extracts an event "travel by walking from front of "T" university station to "T" university" as an event in the preparation state.

At step S1603, the information estimating section 304 estimates supplementary information associated with the extracted events. For example, supplementary information in the implementation state of the event "travel by train from "I" station to front of "T" university station" includes information such as "station of getting off the train", "arrival time", and "information such as mail and news set by the user 100". Moreover, supplementary information in the preparation state of the event "travel by walking from front of "T" university station to "T" university" includes information such as "place of departure/place of arrival", "departure time/arrival time", "time required", and "route information". Supplementary information in the preparation state of the event "meeting at "T" university" includes information such as "notification of preparation time" and "material". The supplementary information such as "material" can be set beforehand by the user 100.

At step S1604, information "station of getting off the train" and "time of arrival" is extracted from the transfer information checked at the time of preparation state, and "information such as mail and news set by the user" is searched from the Internet 400, the individual database 310, and the data base 309 in the server computer. Moreover, the user 100 estimates the expected time of arrival at "T" university based on the arrival time, route from the station, normal walking speed set beforehand or obtained by learning from the walking speed in the past.

The information selecting section 305, searches the preparation state of the meeting from the individual database 310 and the database 300 in the server computer 300 when there is "material" set beforehand by the user 100.

Further, as shown in FIG. 1, the information provided which is searched and selected is transmitted to the information transmitting section 302 of the server computer 300. The receiving section 204 of the mobile gateway 200 receives the information provided which is transmitted from the server computer 300. Further, at step S1605, the information display section 101 displays the information provided. Accordingly, while traveling by train from "I" station to front of "T" university station, the user 100 can obtain automatically the information such as "station of getting off the train", "arrival time", "route information after getting off the train", and "material for meeting", and can spend the time in the train efficaciously.

Figure 17:
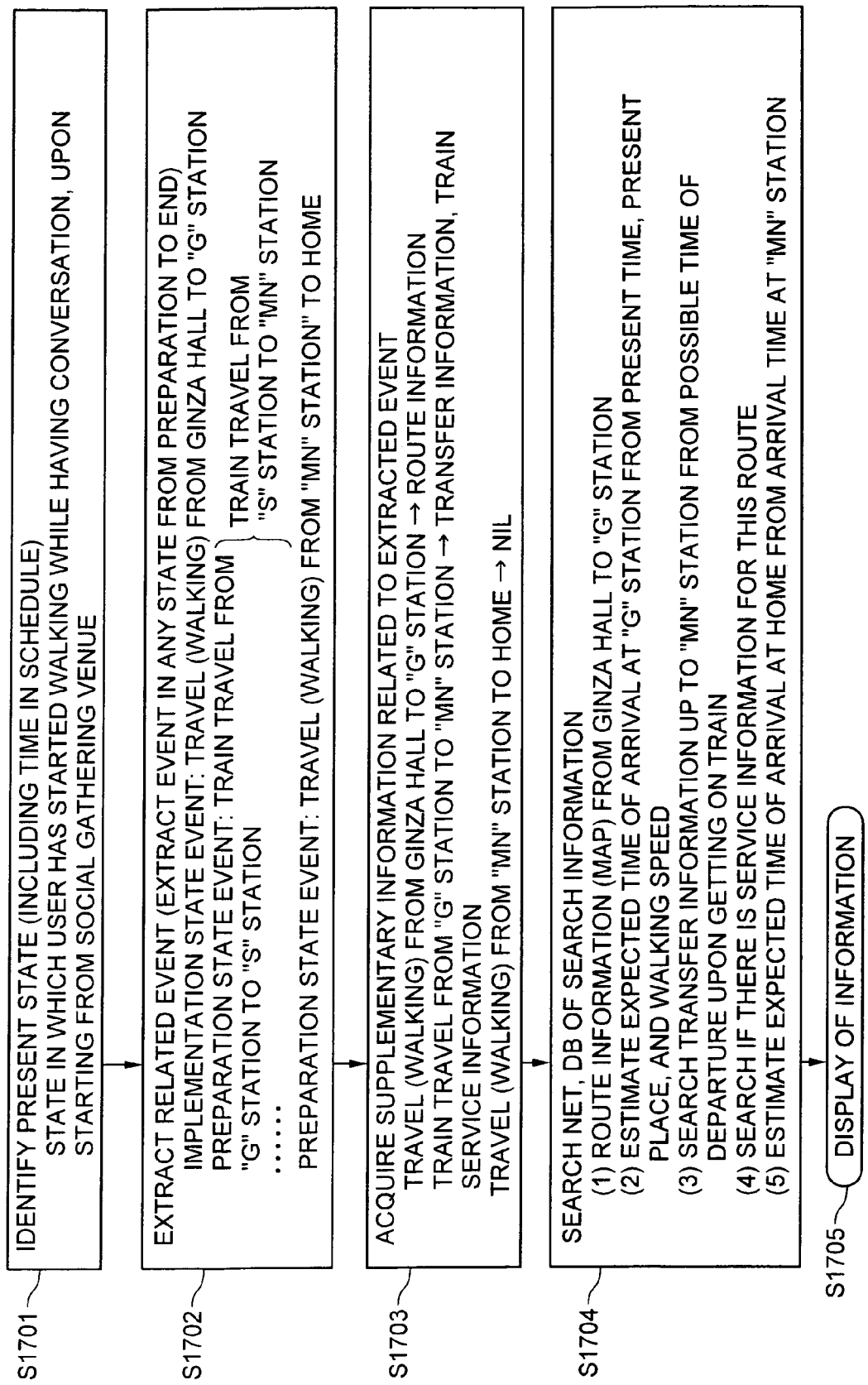
FIG. 17 is a flow chart showing a third estimation example of information.

FIG. 17 is a flow chart showing a procedure of a third example of estimating and selecting the information. At step S1701, the active state identifying section 303 identifies the present state of the user 100. For example, in the third example, a state in which the user 100 acting according to a schedule similar to the case in FIG. 14 has left the social gathering venue and started walking while talking at the present time 22:00 hour is considered.

At step S1702, the active state identifying section 303 extracts an associated event at the present time from the schedule and the sub-schedule. For example, the active state identifying section 303 extracts an event "travel by walking from GINZA hall to "G" station" as an event in the implementation state, and extracts an event "travel by train from "G" station to "MN" station" as an event in the preparation state.

At step S1703, the information estimating section 304 estimates supplementary information associated with the extracted events. For example, supplementary information in the implementation state of the event "travel by walking from GINZA hall to "G" station" includes information such as "route information", "scheduled time of arrival", "difference from expected time of arrival". Supplementary information in the preparation state of the event "travel by train from "G" station to "MN" station" includes information such as "transfer information" and "train service information". Supplementary information in the preparation state of the event "travel by walking from "MN" station to home" includes information such as "route information", "scheduled time of arrival", and "difference from the expected time of arrival". However, since such information is not necessary normally, it is desirable to set this information as not to be displayed.

At step S1704, the information selecting section 305 acquires information "route information map" from GINZA hall to "G" station by referring to the database 309 or the other computer 401. Moreover, the information selecting section 305 estimates the expected time of arrival at "G" station of the user 100 based on the present time, the present position, and the walking speed. Further, the information selecting section 305 searches transfer information up to "MN" station at a time at which the user 100 can get on the train. Moreover, the information selecting section 305 further searches "train service information" of the route. Further, the information selecting section 305 estimates "expected time of arrival at home" based on the time of arrival at "MN" station.

As shown in FIG. 1, the information searched and selected is transmitted to the information transmitting section 302 of the server computer 300. The receiving section 204 of the mobile gateway 200 receives the information provided which is transmitted from the server computer 300. Further, at step S1705, the information display section displays the information provided. Accordingly, the user 100 can obtain automatically the information such as "route information map", "transfer information", "train service information", and "time of arrival at "MN" station". Thus, the user 100 need not search by himself or herself intentionally such information, and is relieved from troublesome search.

(Supplementary Information)

Next, details of the supplementary information related to the extracted event will be described. FIG. 18A and FIG. 18B show an example of "supplementary information" set by estimating information required at each scene according to the event and each state of the event. In this case, "wake-up", "travel by train", "travel by walking", "conference, meeting", "work", "break during work", "meal", "travel inside facility", "watching movie etc.", "jogging", and "go to bed" are described as events.

When a predetermined event and a state of that predetermined event are detected, the corresponding supplementary information in FIG. 18A is revealed. The content of the corresponding supplementary information is searched and displayed. However, the basic information such as "information of time" and "background information" (so called wallpaper) can be set beforehand by the user 100 and can be displayed all the time. Moreover, emergency information can be set beforehand by the user 100 and can be displayed by interruption at any time. The emergency information includes information such as information related to safety of the user 100, emergency news of a disaster and accident, and notification of arrival of an important mail. Moreover, it is preferably desirable to set the display in order to avoid stress and cause of danger for the user 100. An example of avoiding is to display information by icons and to display only that information having a high level of interruption. Main items of the supplementary information shown in FIG. 18A and 18B will be described below.

First of all, the event "wake-up" will be described. The user 100 being sleeping in the preparation state of the event "wake-up", the display of the information is meaningless. However, since it is possible to set the most suitable time to wake-up according to the schedule, the weather, and the service condition of the means of transportation, although it is not specified in this system, the system can be structured to perform an environment control for a pleasant wake-up. For example, the server computer 300 can perform controls such as a control of brightness of light and environmental temperature of a bed room of the user 100 based on the preparation state of the "wake-up" which is identified. Moreover, in the implementation state of the event, information such as the present time, the weather forecast of that day, the outside conditions, the health condition of the user 100, and the schedule of that day becomes the supplementary information. The implementation state in this case means, for example, a state from waking up upon stopping a wake-up alarm till starting the activities, or till leaving the bed room.

Next, the event "travel by train" will be described. The implementation state in this case means a state from getting on the train till getting off the train. In the preparation state of the event, the station of getting on/getting off the train, departure/arrival time of the train, time required, fare, the train service condition, and the platform becomes the supplementary information. In the implementation state of the event, the station of getting off the train, the arrival time, and the information set by the user 100 such as mail and news becomes the supplementary information. In a completion state of the event, notification for getting off the train (by alarm) becomes the supplementary information. When the system is structured accordingly, for example, whet it is time for getting off the train, the user 100 can perceive via the MEG 101 the information provided "arrived at the station of getting off. Let's get off the train".

The event "travel by walking" will be described. In the preparation state of the event, information such as the place of arrival/departure, the time of arrival/departure, the time required, and the route information becomes the supplementary information. In the starting state of the event, the departure time is notified (by alarm). In the implementation state of the event, information such as the route information, the scheduled time of arrival, and the difference from the expected time of arrival becomes the supplementary information. By structuring the system in such manner, for example, in a case of the meeting schedule at 15:00 hour, the scheduled time of arrival is displayed as "15:00 hour" and if the travel is smooth the expected time of arrival is displayed as "two minutes in advance". The route information (navigation) is also displayed at the same time, but for places such as user's own house and office with which the user 100 is familiar, by setting beforehand the route etc. not to be displayed, it is also possible to prevent displaying the unnecessary information.

Concrete examples of such case will be described. For example, for going to "B" station from "A" station by a train leaving at 15:00 hour, while walking toward "A" station, it is a starting state of an event "travel by walking to "A" station". Moreover, it is a preparation state of an event "travel by train from "A" station to "B" station". Further, an information display as shown in Table 1 is displayed.

(Table 1)
Right at next signal (or navigation by a map)
Expected time of arrival at "A" station (14:58 hour), expected to arrive two minutes before.
Transfer Information:
From "A" station (15:00 hour) to "B" station (15:26 hour), time required: 26 minutes
Fare: 210 yen, Train service condition: favorable The event "conference meeting" will be described. In the preparation state of the event, information set beforehand by the user such as notification of preparation time (by alarm), material, and items to be arranged beforehand become the supplementary information. In the starting state of the event, notification of the starting time (by alarm) becomes the supplementary information. In the implementation state of the event, items set beforehand by the user such as material, and emotional control information becomes the supplementary information. The emotional control information is not particularly specified in this system, but is information displayed for cooling down the temper according to the tension and anger detected by measurement of an in-vivo signal such as heart beat and blood pressure when the user 100 is extremely tensed or angry. In such cases, many times one loses sight of himself or herself, but by perceiving such information, it is possible to keep ones cool. In the completion state of the event, schedule after that event becomes the supplementary information.

The event "work" will be described. In the preparation state of the event, the schedule and tasks thereon become the supplementary information. In the starting state of the event, notification of shift to a work mode (by alarm) is displayed. In the implementation state of the event, the work mode becomes the supplementary information. In this case, in the information estimating section 304, when the work mode is estimated as the supplementary information, the control-calculation section 308 controls the information selecting section 305 so as to select the information by conditions set beforehand by the user 100 such as prohibiting display of any information not related to work except the emergency information. In the completion state of the event, recovery from the work mode is displayed.

The event "break during work" will be described. In the implementation state of the event, information for diverting mind set beforehand by the user 100 becomes the supplementary information. In the completion state of the event, notification to evoke completion is displayed. Accordingly, it is possible to perform a function of an alarm to prevent excessive break.

The event "meal" will be described. In the preparation state of the event, advice regarding meal according to the health condition, dietary restrictions, and history and preference, information about nearby eating places while being outside becomes the supplementary information. In the starting state of the event, a recommended menu is displayed. In the implementation state of the event, information set beforehand by the user 100 such as mail and news becomes the supplementary information. Moreover, by entering an eating place while being outside, the state of the event changes to the "starting state". In the completion state of the event, the schedule after the meal is displayed.

The event "travel inside facility" will be described. Facility means places such as a station, a hotel, and a theme park. In the preparation state of the event, HP of the facility (tenants, entertainment etc.), and information of a nearest entrance from the present place, and information about the facility becomes the supplementary information. In the implementation state of the event, information about inside of the facility, such as tenants, elevator, escalator, and toilet becomes the supplementary information. In this case, it is desirable to display the information such as tenant information based on an action history and preference of the individual.

The event "watching movie etc." will be described. In the preparation state of the event, information set by the user 100 becomes the supplementary information. In the starting state of the event, notification of a shift to a sleep mode (by alarm) is displayed. In the implementation state of the event, the mode changes to the sleep mode. In this case, in the information estimating section 304, when the sleep mode is estimated as the supplementary information, the control-calculation section 308 controls the information selecting section 305 so as to select the information by conditions set beforehand by the user 100 such as prohibiting display of any information except the emergency information. In the completion state of the event, the mode is recovered from the sleep mode.

The event "jogging" will be described. In the preparation state of the event, motivation stimulating information becomes the supplementary information. In the starting state of the event, notification of the starting time (by alarm) is displayed. In the implementation state of the event, pace, exercise load, motivation maintenance information becomes the supplementary information. In the completion state of the event, information such as notification to evoke completion (alarm to prevent excessive exercise), display of effort effect, and compensation becomes the supplementary information.

The event "go to bed" will be described. In the preparation state of the event, next day's schedule, weather, and scheduled wake-up time become the supplementary information. In the starting state of the event, notification of time for going to bed is displayed. Accordingly, unwillingly sitting up till late can be prevented.

Next, by referring to FIG. 19, a concrete relation between the identification of the active state and the information provided will be described further by using simple examples. Here, a case of leaving home and heading toward the nearest station by using only sensors such as walking condition sensors like the GPS, the foot pressure sensor, and the clock is assumed.

When the user 100 is outdoor between the home and the nearest station and is walking hurriedly, for example, the user 100 is identified to be in the preparation state of an event "travel by train from the nearest station to "O" office", in the implementation state of an event "travel by walking to the nearest station", and in a state of "hurriedly heading for the station". At this time, for example, "time" is displayed. This concept will be described by using FIG. 19.

In FIG. 19, three orthogonal axes coordinate system (hereinafter, called as "TPO factor axes") having three axes namely an axis showing a place of the user 100, an axis showing the travel, and an axis showing time in the schedule is used. A state in which the user 100 is running with short steps toward the station during the time of travel from home to the nearest station is considered.

The active state identifying section 303 identifies the user 100 to be in a state surrounded by thick lines in three-dimensional space defined by TPO factor axes. Further, the active state identifying section 303 identifies events associated with this time by referring to the present time and the schedule as in the preparation state of an event "travel by train from the nearest station to "O" office", and in the implementation state of the event "travel by walking to the nearest station".

At this time, based on an estimation "in such state, the user 100 is ought to be bothered about the next transfer train" made by the information estimating section 304, the information selecting section 305 selects the timetable from the supplementary information "departure of the next train" which is set beforehand.

Thus, in this system, since the identification of the active state is performed based on time, place, and occasion, hereinafter called as "TPO estimation", and not being dependent only on occasion and time, it is possible to provide information complying with the user's interest. Moreover, to simplify the description, only the walking state is used as occasion, and as it is described earlier, by combining a plurality of axes such as a mastication and utterance state, it is possible to judge the situation in more detail.

FIG. 20A and FIG. 20B show still another relation of a measurement signal from the sensor 110 etc. and an active state which is identified. In FIG. 20A and FIG. 20B, seven sensors namely "a clock and a schedule", "a GPS", "an indoor-outdoor sensor", "a movement measurement sensor", "an external sound microphone", "a bone conduction microphone", and "a foot pressure sensor" are used as sensors. Based on measurement signals from these seven sensors, "conversation" and "holiday" are identified as timing, "daily life time" "daily working time", and "non-daily time" are identified as day and time, and "place" and "travel" are identified as space.

Examples of content of "conversation" identified are "talking", "listening", "none". Examples of content of "holiday" are "week day", "weekend", "holiday", and "first day after holiday". Examples of content of "daily life time" are "wake-up", "breakfast", "lunch", "dinner", and "go to bed". Examples of content of "daily working time" are "go to work", "work" during break and meeting, and "return home". Examples of content of "non-daily time" are "departure", "travel", "event" of business trip and leisure, "travel" and "return".

Moreover, examples of content of "place" which is identified are bed room, living room, dining room, and apart from these, "home", "station", "shop", "hospital", office room, conference room, resting room, and apart from this, "office", "movie theatre", "indoor stadium", "sightseeing spot", "town", "sea and mountain", and "outdoor other than these".

Moreover, examples of "travel" which is identified are "public transport", "drive by self" car and vehicle, "walking" "slowly" and "dash", and "no travel". Further, based on the measurement signals from the seven sensors 110 mentioned above, these active states are identified.

Next, based on the content of the identified active state, the information required by the user 100 is estimated and selected. FIG. 21 shows a relation of the "active state" and the "supplementary information". "Navigation" information as the supplementary information and concrete map information up to the destination will be described. A case in which the active state is "business trip" from the "non-daily time", and identified as "unfamiliar place" and "travel by walking". When these identifications are implemented at the same time, the information estimating section 304 estimates "map information up to the destination". Also for "news" and "mail" which are other items, when each "active state" described in TPO factor axes column in FIG. 21 is identified, the corresponding information is estimated and selected.

Thus, according to the first embodiment, it is possible identify the active state of the user 100, and to display timely the information required by the user 100 based on the active state which is identified.

Second Embodiment

Figure 22:
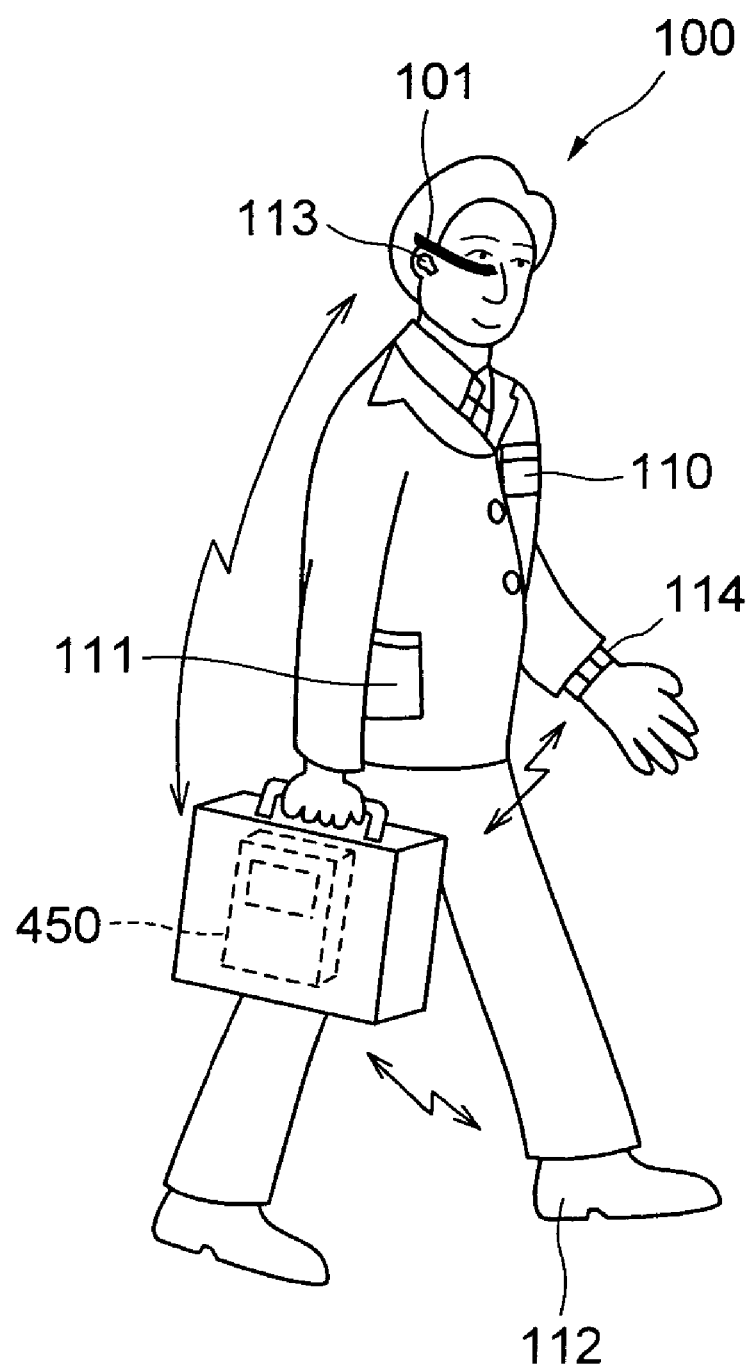
FIG. 22 is a diagram showing a schematic structure of an information display system according to a second embodiment.

An information display system according to a second embodiment of the present invention will be described. FIG. 22 shows a schematic structure of the information display system according to the second embodiment. In the first embodiment, the measurement signals from the sensor 110 etc. are transmitted to the server computer 300 via the mobile gateway 200. Moreover, the information provided from the server computer 300 is transmitted to the MEG 101 of the user 100 via the mobile gateway 200. Whereas, the second embodiment differs from the first embodiment at a point that a notebook (laptop) personal computer 450 serves functions of both the mobile gateway 200 and the server computer 300. The same reference numerals are used for sections same as in the first embodiment, and repeated description is omitted.

Figure 23:
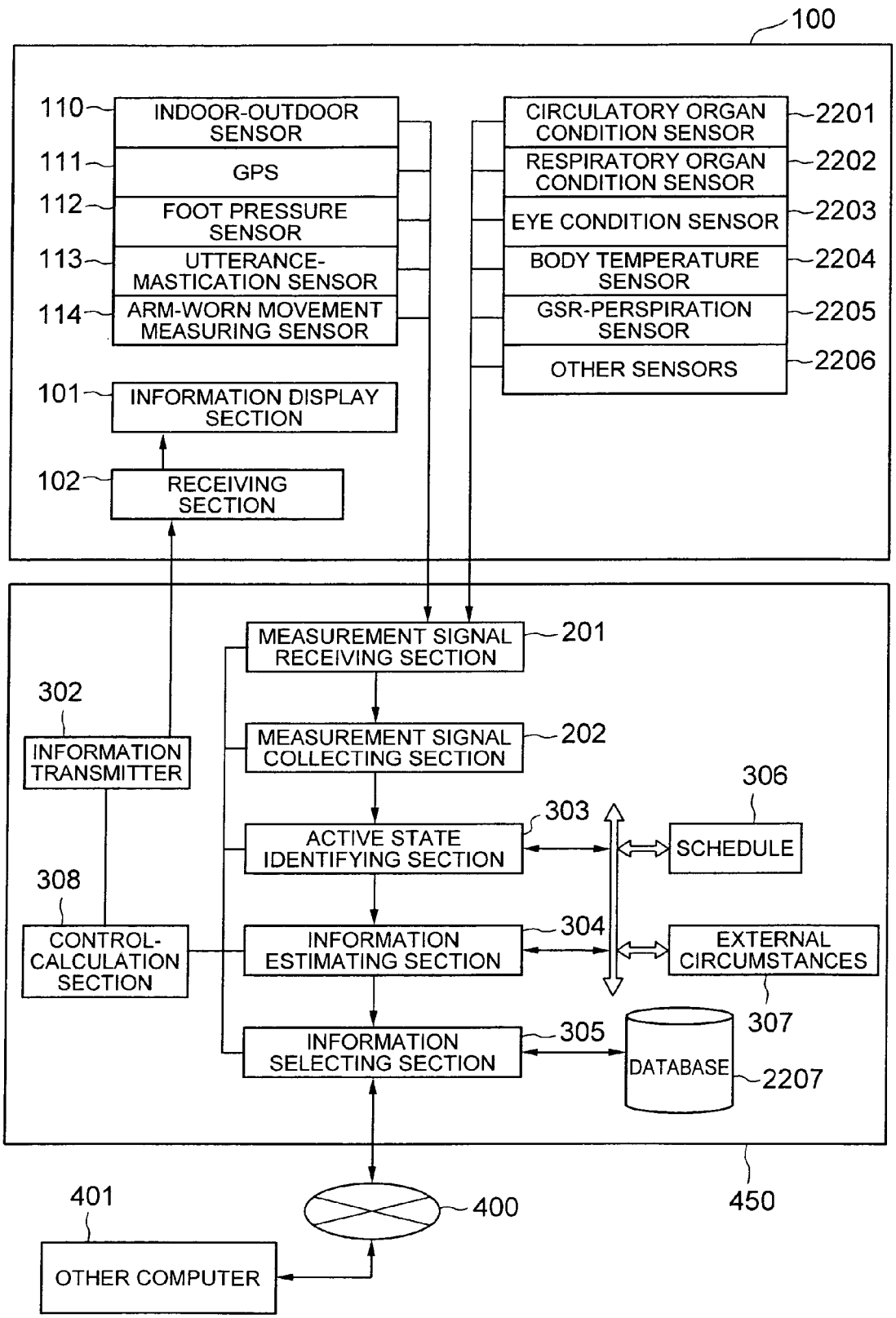
FIG. 23 is a diagram showing a functional block of the information display system according to the second embodiment.

FIG. 23 shows functional blocks of the information display system according to the second embodiment. This information display system includes a group of sensors worn by the user 100 and the notebook personal computer 450.

First of all, the group of sensors worn by the user 100 will be described. The user 100 wears on the body the indoor-outdoor sensor 110, the GPS 111, the foot pressure sensor 112, utterance-mastication sensor 113, and the arm-worn movement measuring sensor 114. These sensors 110 etc. have same structure as the structure of devices described in the first embodiment.

In the second embodiment, the user 100 wears further a circulatory organ condition sensor 2201, a respiratory organ condition sensor 2202, an eye condition sensor 2203, a body temperature sensor 2204, a GSR-perspiration sensor 2205, and other sensor 2206.

(Circulatory Organ Condition Sensor)

The circulatory organ condition sensor 2201 is such as a pulse oximeter and an arm-worn sphygmomanometer. The pulse oximeter measures oxygen saturation of arterial blood sent to peripheral tissues specified per heart beat or other peripheral tissues without collecting blood. Hemoglobin in human blood absorbs red color when not combined with oxygen. Whereas, when hemoglobin combines with oxygen, hemoglobin does not absorb much of red color. The pulse oximeter, by using this property, measures as to how much oxygen is included in the hemoglobin in blood. Accordingly, it is possible to know the oxygen saturation of arterial blood. As a result, it is possible to detect a condition of a circulatory organ such as heart and blood vessels of the user 100 by the pulse oximeter.

(Respiratory Organ Condition Sensor and Eye Condition Sensor)

Moreover, the respiratory organ condition sensor 2202 is a respiration sensor. The respiration sensor detects a respiration rate and a respiration frequency. The eye condition sensor 2203 is an eye camera for example. The eye camera detects an eye movement and papillary reflex of the user.

(GSR-Perspiration Sensor)

The GSR-perspiration sensor is a sensor which measures GSR (Galvanic Skin Response: skin electric resistance value). For measuring the GSR, a pair of electrodes is installed with a predetermined gap between the electrodes on a body surface of the user 100 such as palm or a platar. A feeble current is passed through both the electrodes and a potential difference and current are measured. By using the measured values, a resistance is calculated. Accordingly, it is possible to detect the perspiration condition of the user 100.

(Other Sensor)

The other sensor 2206 detects a tensed condition of the user 100. As a method for sensing an awaken state, the tensed condition, a fatigue condition, a physical condition, and an empty stomach condition is a normal method which uses heart beat and body temperature etc. Any of these conditions, unlike actions, is not a condition which can be measured directly. An example of a sensor for detecting the tensed condition of the user is an electroencephalogram.

In FIG. 22, to facilitate the understanding, the diagrammatic representation of the circulatory organ condition sensor 2201, the respiratory organ condition sensor 2202, the eye condition sensor 2203, the body temperature sensor 2204, the GSR-perspiration sensor 2205, and the other sensor 2206 is omitted.

Each of the sensor 110 etc. mentioned above, includes a Bluetooth chip (not shown in the diagram) for wireless communication. The measurement signal from the sensor 110 etc. is changed to digitalized data and is transmitted to the notebook personal computer 450.

(Notebook Personal Computer)

The notebook personal computer 450 will be described. The notebook personal computer 450 has a size which can be accommodated in a bag held by the user 100. The measurement signal receiving section 201 of the notebook personal computer receives a measurement signal transmitted from the sensor 110 etc.

The measurement signal collecting section 202 collects a plurality of measurement signals from the sensor 110 etc. as one signal. The active state identifying section 303 identifies the active state of the user 100 based on the measurement signal received. The information estimating section 304 estimates the information required by the user 100 based on the active state which is identified by the active state identifying section 303.

The active state identifying section 303 and the information estimating section 304 refer to the schedule 306 and the external circumstances 307 respectively. The schedule 306 includes the schedule of the user 100. Moreover, the external circumstances 307 includes the weather information and the information of traffic jam.

A database 2207 stores various types of information including the information required by the user 100. Moreover, the database 2207 is not restricted to have a structure integrated in the notebook personal computer 450. For example, the structure may be such that the database is provided outside the notebook personal computer 450.

The information selecting section 305 selects the information required by the user 100 which is estimated by the information estimating section 304 from the plurality of information stored in the database 2207. The information selecting section 305 is structured to enable communication with the other computer 401 via the dedicated line or the Internet. Accordingly, the information selecting section 305 can acquire the information required by the user 100 via the other computer 401.

The information transmitting section 302 transmits the information selected by the information selecting section 305 to a receiving section 102 of the MEG 101. Moreover, the control-calculation section 308 controls a measurement signal receiving section 201, the measurement signal collecting section 202, the active state identifying section 303, the information estimating section 304, the information selecting section 305, and the information transmitting section 302.

Further, the sensor 110 etc. and the notebook personal computer 450 include the wireless tag (Bluetooth chip) which is a receiving section. Accordingly, the sensor 110 etc. and the notebook personal computer 450 can perform the wireless communication by the Bluetooth.

Each of a function of the active state identifying section 303, a function of the information estimating section 304, and a function of the information selecting section 305 being the same, the description of these functions is omitted. In the second embodiment, as compared with the first embodiment, the circulatory organ condition sensor 2201, the respiratory organ condition sensor 2202, the eye condition sensor 2203, the body temperature sensor 2204, the GSR-perspiration sensor 2205, and the other sensor 2206 are used additionally. Therefore, the active state identifying section 303 can identify items of more detailed active state than in the first embodiment.

(A Day's Scenario of User)

For example, a case in which a profession of the user 100 is sales is considered. FIG. 24A, FIG. 24B, FIG. 24C, and FIG. 24D to FIG. 31A, FIG. 31B, FIG. 31C, and FIG. 31D show a life trend of a day of the user 100 who uses this information display system. A column "life scene of user" describes reaction with respect to information displayed in the MEG 101. A column "function of system" describes information provided to the user 100 and environment control of the surrounding etc. of the user 100. The environment control means controlling of peripheral equipment of the user 100 such as air-conditioning and lighting equipment by linking an environment control system with this information display system.

A column "sensor based data" shows the sensor 110 etc. referring to the identification of the active state etc. In FIG. 24A, FIG. 24B, FIG. 24C, and FIG. 24D to FIG. 31A, FIG. 31B, FIG. 31C, and FIG. 31D, "A" in the column "sensor based data" denotes that the measurement signal from the respective sensor is effective for identifying the active state. Moreover, "B" in the column "sensor based data" denotes a case in which the detection by the sensor is not easy. For example, when the detection becomes a burden for the user 100, it shows a case of detection of the measurement signal to be not easy. Therefore, a measurement signal from the sensor denoted by "B" denotes a state that the measurement signal from the sensor can be also used if required for the identification of the active state. Furthermore, "non-sensor based data used" shows data used for the identification of the active state, and information provided which is displayed. A part of the plurality of life scenes of the user 100 will be described below.

In the "non-sensor based data", "A" denote data used for identifying an active state, or the most suitable information which is provided, and "B" denotes information which may be used but having a lower degree of importance than "A".

The life scene of the user is expression of user's mind in writing, assuming that the user actually works in such system environment.

Moreover, in the "sensor based data used" column in FIG. 24A, FIG. 24B, FIG. 24C, and FIG. 24D to FIG. 31A, FIG. 31B, FIG. 31C, and FIG. 31D, "time (hour) and place" can be detected from the clock and the schedule. "Position and place" can be detected from the indoor-outdoor sensor 110 and the GPS 111. "Walking and exercising state" can be detected by the foot step sensor 112 and the movement measuring section 114.

(Before Leaving, at Home)

Item no. 1 in an extreme left column in FIG. 24A and FIG. 24C will be described. At the wake-up time of the user 100, the active state identifying section 303 identifies the active state of the user based on an "awaken state" detected by the "hour (clock time) and time (time period)", the "circulatory organ condition", the "respiratory organ condition", the "body temperature", and the other sensor. For example, the active state identifying section 303 identifies the user 100 to be in a "morning, awaken state on bed". The control-calculation section 308 performs functions such as lightening the bed room, controlling the temperature of the bed room to be pleasant for waking up, supplying a suitable fragrance for waking up, and supplying sounds (such as music) suitable for waking up. Accordingly, the user 100 can feel that "I have not been awakened by the alarm bell, and today also I woke up naturally and in a pleasant mood".

(During Commuting)

Item no. 10 in an extreme left column in FIG. 25A and FIG. 25C will be described. When the user 100 commutes, the active state identifying section 303 identifies the user 100 to be traveling based on the "hour and time", the "position and place", and the "walking and exercising state". The information estimating section 304 estimates information which supports the action, according to the schedule thereon. The information selecting section 305 selects the most suitable information related to the "map information", the "schedule", and the "timetable and transfer". For example, information related to the "timetable and transfer", as described in the first embodiment, includes information of the "service situation", in addition to the concrete departure time of the train. For example, in the normal commuting route, when the train is delayed due to an accident, a commuting route using other private railway is selected. The MEG 101 displays this information appropriately.

Accordingly, the user 100 can perceive that "as I started walking towards the station, the transfer information was displayed. The train traffic being affected due to the accident, use of a private railway line has been recommended. As I don't want to be delayed for the meeting, let's use the private railway line".

In this case, when detailed character information is displayed by using the MEG 101, sometimes contrarily the perception of information by the user becomes difficult. Therefore, it is desirable that information to be displayed on the MEG 101 is abbreviated to brief information simplified by the optimization of information to be displayed as described in the first embodiment.

(In Office)

Item no. 16 in an extreme left column in FIG. 26A and FIG. 26C will be described. When the user 100 is in the office, the active state identifying section 303 identifies the active state of the user based on the "hour and time" and the "position and place". The information estimating section 304 estimates information which supports an action such as setting the action time according to the schedule. The information selecting section 305 selects the most suitable information related to the "schedule". Accordingly, when the user 100 arranges the material for the meeting, an icon showing that the time for the meeting is coming closer which is the information provided is displayed on the MEG 101. As a result, the user 100 can perceive "in a moment, it's time for the meeting. Let's make a move".

Item no. 22 in an extreme left column in FIG. 27A and FIG. 27C will be described. When the user 100 is outside, the active state identifying section 303 identifies the user 100 to be traveling based on the "hour and time", the "position and location", and the "walking and exercising state". The information estimating section 304 estimates information which supports the action according to the action, such as navigation information according to the travel of the user 100. The information selecting section 305 selects the most suitable information related to the "map information", the "timetable and transfer". The MEG 101 displays this information appropriately.

Accordingly, the user 100 can perceive "even in a case of a place visiting for the first time, I am at ease since the information such as the most suitable place to get on the means of transport and exit of metro is provided".

(At Sales Destination)

Item no. 26 in an extreme left column in FIG. 28A and FIG. 28C, will be described. When the user 100 has gone out, the active state identifying section 303 identifies the user 100 to be traveling based on the "hour and time", the "position and place", and "the walking and exercising state". The information estimating section 304 estimates information which supports an action according to the action, such as navigation information according to the travel of the user 100. The information selecting section 305 selects the most suitable information related to the "map information" and the "timetable and transfer". The MEG 101 displays this information appropriately.

Accordingly, the user 100 can perceive "even in a case of a place visiting for the first time, since the MEG guides up to the sales destination, I don't have to hang around carrying the map".

Item no. 31 in an extreme left column in FIGS. 29A and 29C, will be described. When the user 100 has gone out, the active state identifying section 303 identifies the user 100 to have entered a commercial facility where the scheduled reception is held, based on the "position and place". The information estimating section 304 detects the entry of the user 100 in the commercial facility and changes to information inside the facility. Further, the information estimating section 304 estimates information inside the facility. The information selecting section 305 selects the most suitable information about the "shops and facility information". The MEG 101 displays this information appropriately.

Accordingly, the user 10 can perceive "I have arrived at the hotel. As I was thinking of buying a film before going to the venue, the display changed to the information inside the facility".

(After Returning to Office)

Item no. 35 in an extreme left column in FIGS. 30A and 30C will be described. When the user 100 has returned to the office, the active state identifying section 303 monitors the active state of the user 100, particularly the physical condition even during the work to prevent the overwork, based on the "hour and time", the "position and time", the "circulatory organ condition", the "respiratory organ condition", the "eye condition", the "body temperature", and the "fatigue condition" detected by the other sensor. The information estimating section 304 estimates information which encourages timely break. The MEG 101 displays this information appropriately.

Accordingly, the user 100 can perceive "I have finished preparing 70% of the material. Since there is an indication for a break, let's take a breather".

(To Home)

Item no. 41 in an extreme left column in FIG. 31A and FIG. 31C will be described. When the user 100 returns home, the active state identifying section 303 identifies the user 100 to be in a state on the way to home based on the "position and place" and the "walking and exercising condition". The information estimating section 304 estimates in order from information of highest priority based on the state on the way to home of the user 100. The information selecting section 305 selects the most suitable information related to the "timetable and transfer" and the "mail and news". The MEG 101 displays this information appropriately.

Accordingly, the user 100 can perceive "by using the waiting time and travel time of the train, today's news is displayed. An image of a visitor visited in my absence is also displayed. Not being at home in the day time helps me".

Thus, the information display, the environment control, and the action support by this information display system for typical life scenes from the life scene of the user 100 from waking up till returning home have been described. In FIG. 24A, FIG. 24B, FIG. 24C, and FIG. 24D to FIG. 31A, FIG. 31B, FIG. 31C, and FIG. 31D, the information display, the environment control, and the action support by this information display system for the other life scenes of the user 100 are performed according to the content described in the diagrams. Therefore, detailed description of other life scenes is omitted. According to the second embodiment, it is possible to identify the active state of the user 100, to display the information required by the user 100, to control the environment condition of the user 100, and to support the actions of the user 100.

Modified Embodiment

Figure 32:
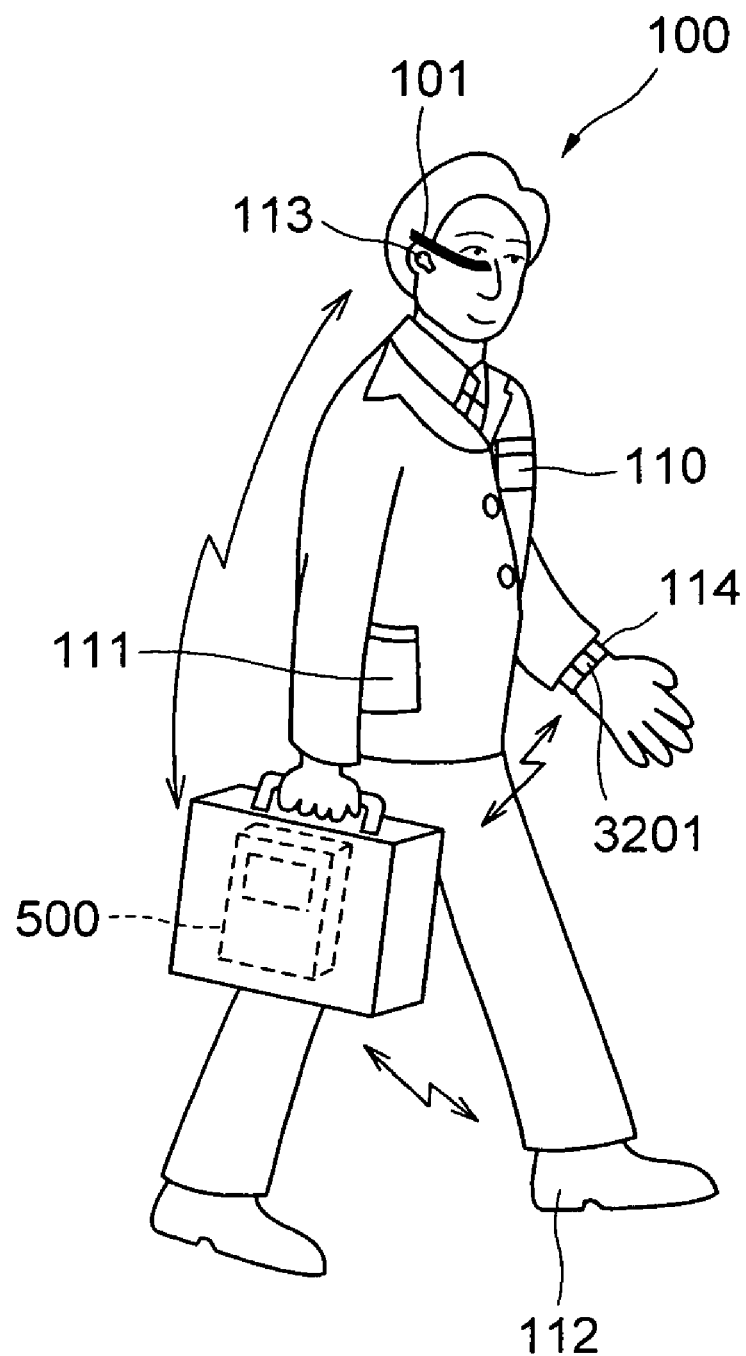
FIG. 32 is a diagram showing a schematic structure of an information display system according to a modified embodiment.

An information display system according to a modified embodiment of the present invention will be described. The same reference numerals are used for sections same as in the first and the second embodiment, and repeated description is omitted. FIG. 32 shows a schematic structure of the information display system according to the modified embodiment. In this information display system, lifestyle habits of the user 100 can be monitored.

The user 100 wears sensors such as the indoor-outdoor sensor 110, the GSP 111, the foot pressure sensor 112, the utterance-mastication sensor 113, and a pulse and blood pressure sensor 3201. The pulse and blood pressure sensor 3201 is a wrist watch type sensor to be worn on an arm. The pulse and blood pressure sensor 3201 detects a pulse rate, a pulse speed, regularity and irregularity, and a blood pressure. The measurement signals from the sensor 110 etc. are transmitted to a monitor terminal 500. Based on the measurement signals, the lifestyle habits of the user 100 are monitored.

Contents of the lifestyle habits which can be monitored according to the modified embodiment will be described. For example, regarding "sleep", lifestyle habits include a timing of going to bed, sleeping time, and a nature of sleep. Regarding "meal", the lifestyle habits include timing of having a meal, time for taking a meal, and a nature (mastication frequency) Regarding "exercise", the lifestyle habits include time of doing exercise, time for how long the exercise is continued, and balance of body parts such hands and legs. Regarding "action pattern", the lifestyle habits include time for how long one is outside and amount of conversation. By monitoring these lifestyle habits, it is possible to prevent a lifestyle-related disease, and to have detection at an early stage of a mental and physical disorder caused due to aging. As a result, it is possible to reduce medical expense. Moreover, it has been indicated that mental disorder such as juvenile amnesia which has been pointed out in recent years has a deep relevancy with the time of conversation with others and time of staying outside, and this modified embodiment can be used as a tool for health care and modification support.

APPLICATION EXAMPLE

Figure 33:
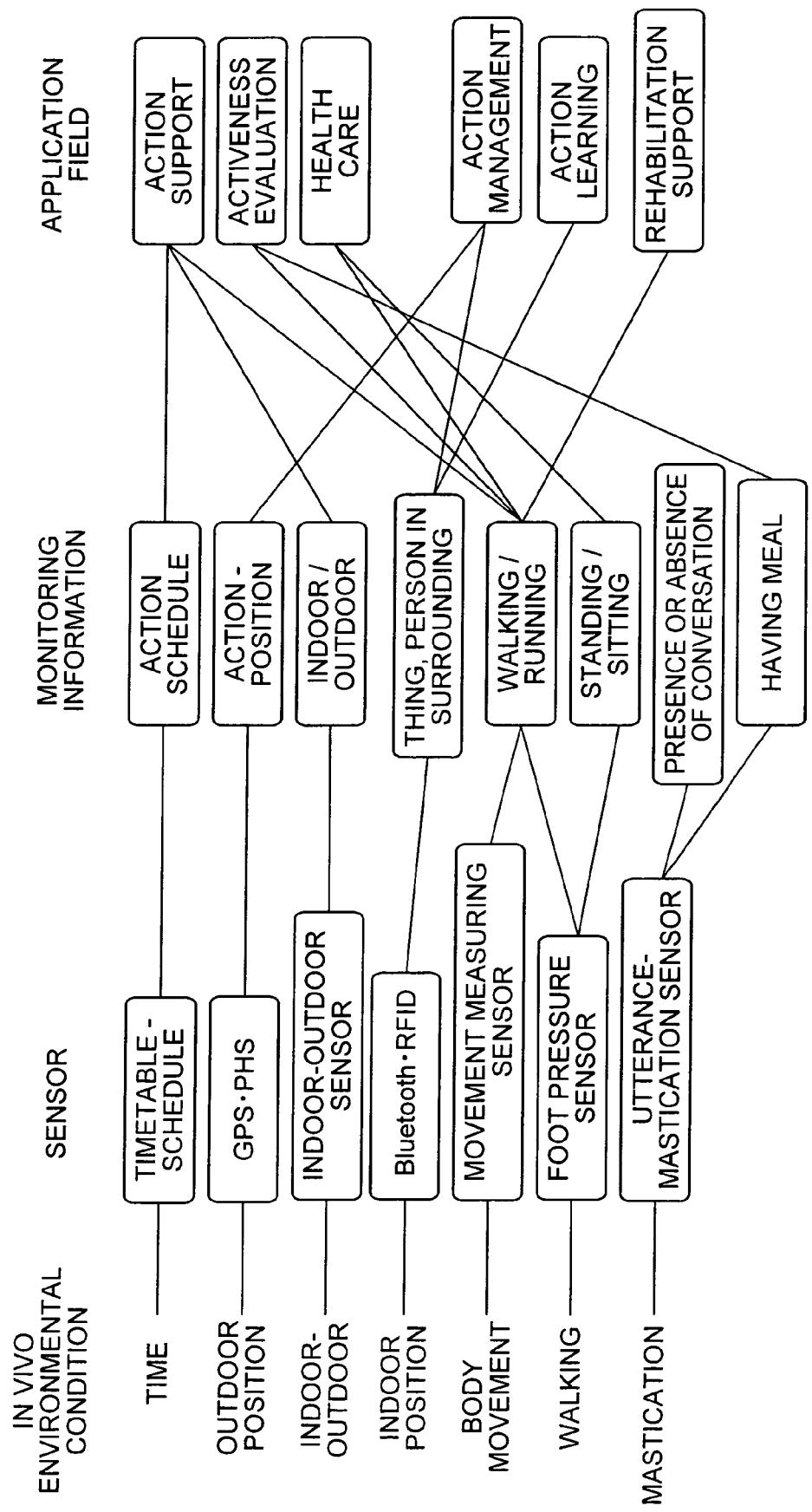
FIG. 33 is a diagram showing an application example of the information display system of the present invention.

An application example of the information display system according to the present invention will be described based on FIG. 33 and FIG. 34. FIG. 33 shows a relation of an identified active state and a field of application. The active state of the user 100 (corresponds to "in vivo environment condition" in FIG. 33), is a state such as a "time travel", an "outdoor position", an "indoor-outdoor", an "indoor position", a "physical exercise", a "walking state", and a "masticating state". The sensor 110 etc. described in the first and the second embodiment is used. In this case, an RFID (Radio Frequency Identification) can also be used. The RFID stores data in a tag having an excellent environment resistance, and communicates with a reader by electric waves or electromagnetic waves. The tag has various shapes such as a label shape, a card shape, a coin shape, and a stick shape, and the shape of the tag can be selected according to an application. By using such RFID, it is possible to distinguish and control the user 100 by a minute wireless chip.

Further, information such as an "schedule", "action and position", "indoor/outdoor", "things and persons around", "walking/running", "standing/sitting" "presence or absence of conversation", and "having meal" can be identified (monitored). Accordingly, by this information display system, it is possible to perform the "action support", an "evaluation of degree of action", the "health care", the "action control", the "action learning", and a "rehabilitation support".

Figure 34:
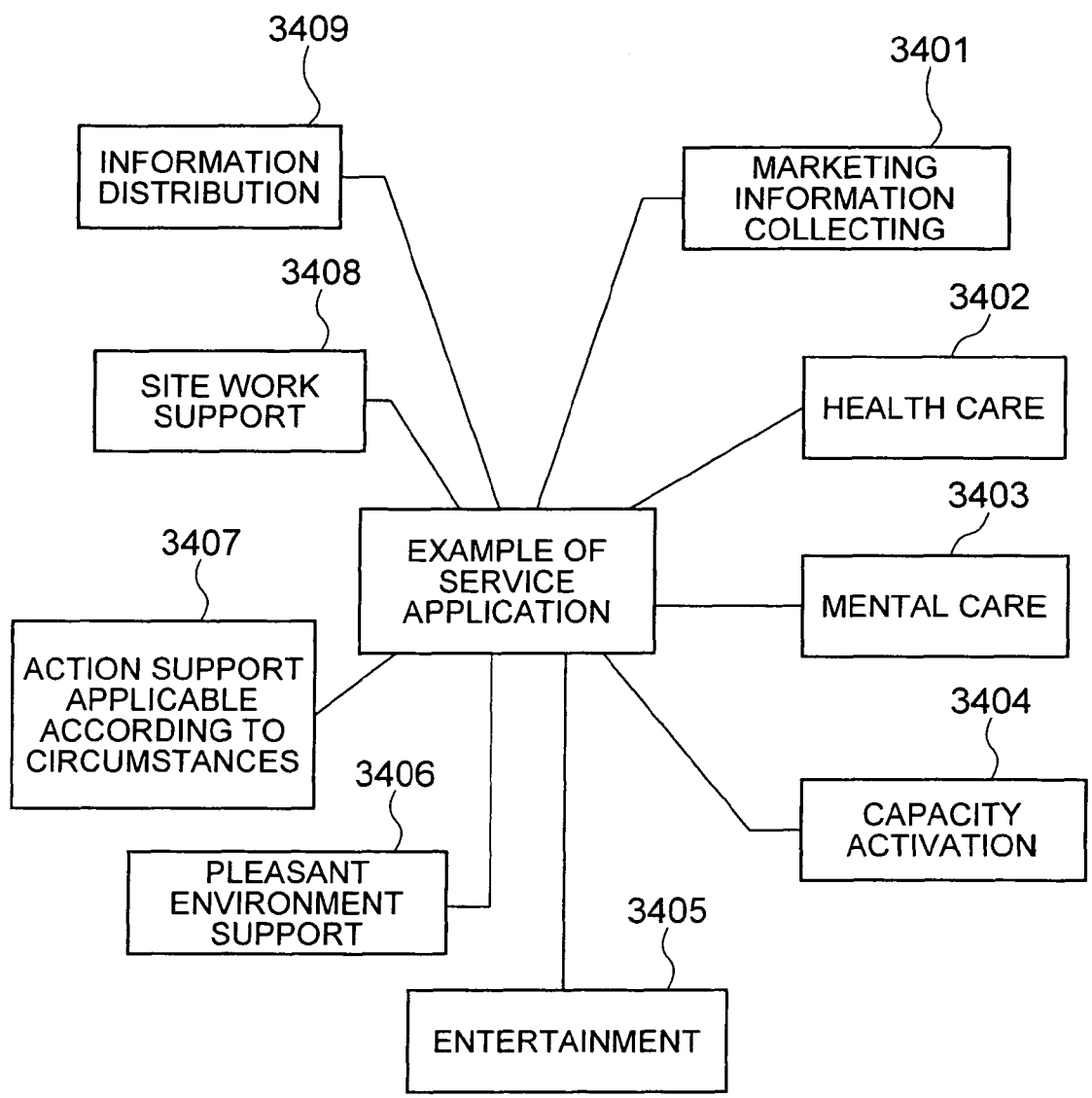
FIG. 34 is another diagram showing an application example of the information display system of the present invention.

FIG. 34 shows another application example of this information display system. A marketing information collecting 3401 is performed by detecting user's preference, action/traffic line, a degree of interest, a degree of excitation, and comfort. Accordingly, it is possible to analyze customer's preference by keeping a PHS (Personal Handyphone System) in user's shopping basket or by using customer's PDA (Personal Digital Assistance) for guidance. Moreover, it is possible to acquire an objective questionnaire by collecting information about feeling of the user during test driving a car, or by collecting user's reaction at an exhibition.

A health care 3402 is performed by collecting a log (record) of a pattern of an amount of exercise and the action of the user, and by collecting a log of in vivo information. Accordingly, it is possible to perform a healthy dietary life support, a body rehabilitation support, a sound sleep support by the environment control, a health monitoring service, a prevention of thrombus, and a prevention of fatigue. Particularly, in an effective support of workout for example, it is possible to give real-time recommendations, in other words to recommend by beneficial information provided in real time.

A mental care 3403 is performed by a log of a degree of tension or TPO, a conversation log, an action pattern log, and a neural balance log. Accordingly, it is possible to perform a mental counseling, a biofeedback, a stress parameter display, a mental care of an old person by a safety support and a rehabilitation support, an objective evaluation of a therapeutic effect for a professional athlete, and to have a greater value added content of a random delivery service such as fortune-telling and today's maxim.

A capacity activation 3404 is performed by a detecting a brain condition and stimulating brain. Accordingly, it is possible to perform a right-brain workout, a concentration nurturing, a meditation support, and a breathing method support. Moreover, in an entertainment 3405, it is possible to perform a virtual game in a field by a detection log of movements of the user.

Pleasant environment support 3406 is performed for example by a TPO detection by the GPS, a schedule interpretation, and an autoscheduler. Accordingly, it is possible to perform an air-conditioning control, a lighting control, a fragrance control, and a BGM (Back Ground Music) control.

An action support applicable according to circumstances 3407 is performed for example by the TPO detection by a clock and the GPS etc., the schedule interpretation, and the autoscheduler. Accordingly, it is possible to perform prevention of leaving things behind (forgetting things), waking up, and the timetable display.

In a site work support 3408, it is possible to perform supports such as a nursing support, a safe-driving support, a dangerous-work support by detecting a deterioration of a work environment and a health problem, an operation-efficiency improvement support, a cooking preparation support, and a restaurant waiter timing support. In the nursing support, a nurse who is nursing a patient performs actions at a site of treatment following instructions from a doctor. At this time, sometimes instructions of the doctor are changed at the eleventh hour. In such case, by using this information display system, it is possible to obtain information immediately. Moreover, by using the MEG, it is possible to perform smooth treatment support with both hands remaining free.

An information distribution 3409 is performed by a sensibility, the TPO detection, and a preference detection. Accordingly, it is possible to acquire a navigation of the schedule, the position and the direction of travel, and information inside the commercial facility, preference applicable information such as information of shops, work information of newspaper and stocks, private information, reminder, personal information, and mail.

Thus, the information display system according to the present invention can be used suitably for an application range of an extremely wide variety. Moreover, by using the MEG etc., it is possible to perform a seamless information display which can be perceived in all scenes in the daily life of the user. Further, through the seamless information display, action support and health care of the user is achieved.

(Computer Program)

As a computer program for hardware of the information system, it is desirable to use a computer program for the information display system readable by a computer, which when executed by the computer causes the computer to perform functions of a measuring means which measures a state of at least each port of a body of the user, an active state identifying means which identifies the active state of the user based on the measurement result of the measuring means, an information estimating means which estimates the information required by the user based on the active state identified by the active state identifying means, an information storage means which stores at least the information required by the user, an information selecting means which selects the information required by the user estimated by the information estimating means from a plurality of information stored in the information storage means, and an information display means which displays information required by the user selected by the information selecting means.

Functions of the active state identifying section 303, the information estimating section 304, the information selecting section 305, and the control-calculation section 308 can be realized by using a CPU for example. Further, it is also possible to realize the functions of the active state identifying section 303, the information estimating section 304, the information selecting section 305, and the control-calculation section 308 by causing the server computer 300 to read the computer program from an information recording medium.

Moreover, as the information recording medium, it is possible to use various media readable by the computer such as a flexible disc, a CD-ROM (Compact Disc—Read Only Memory), a magneto-optical disc, an IC card (Integrated Circuit card), a ROM cartridge (Read Only Memory cartridge), a printed matter such as a punch card and a bar code having codes printed thereon, and an internal storage unit (memory such as a RAM (Random Access Memory) and ROM) of the computer. A reading method of the computer program may be a contact method or a non-contact method.

Furthermore, instead of the information storage medium, it is also possible to realize each of the functions mentioned above by downloading the computer program for realizing each function from a host device via a transmission path.

Thus, in the information display system according to the present invention, the measuring means measures a state of at least each part of the body of the user such as the arm movement or the leg movement. The active state identifying means identifies the active state of the user such as the sitting state, based on the measurement result of the measuring means. The information estimating means estimates the information required by the user based on the active state which is identified by the active state identifying means. The information storage means stores at least the information required by the user which is estimated by the information estimating means. Next, the information selecting means selects the information required by the user which is estimated by the information estimating means from the plurality of information stored in the information storage means. The information display means display the information required by the user which is selected by the information selecting means. Thus, in the present invention, the information estimating means estimates the information required by the user based on the active state which is identified by the active state identifying means. Accordingly, it is possible to estimate information having the most suitable content according to the active state of the user. Further, the information display means displays the information required by the user which is selected by the information selecting means. Therefore, the required information is displayed for the user. As a result, it is possible to acquire the required information without selecting and acquiring intentionally the predetermined information by the user. In other words, According to the present invention, it is possible to identify the active state of the user, and to display timely the information required by the user based on the active state which is identified.

Moreover, in the first embodiment and the second embodiment, a network communication using the Bluetooth is used. However, the present invention is not restricted to the communication network using the Bluetooth and a communication mode between the mobile gateway and the server computer and a communication mode between the sensor 110 etc. and the notebook personal computer may be any mode which can perform a data transfer such as a PHS communication line, a portable telephone communication line, a wireless LAN, and an infrared communication. Thus, the present invention can have appropriate modifications which fall within a scope of basic teaching herein set forth.

Thus, the information display system according to the present invention is useful for a system which identifies the active state of the user and displays the required information, particularly a system which includes a small size information display section such as the MEG.

What is claimed is:

1. An information display system comprising:
    a measuring section configured to measure a state of a plurality of parts of a body of a user;
    an active state identifying section which identifies an active state of the user based on a measurement result of the measuring section;
    an information estimating section which estimates information required by the user based on the active state identified by the active state identifying section;
    an information storage section which stores at least the information estimated to be required by the user by the information estimating section;
    an information selecting section which selects the information estimated to be required by the user from a plurality of information items stored in the information storage section; and
    an information display section which displays the information estimated to be required by the user and selected by the information selecting section;

wherein the information stored in the information storage section comprises information to which metadata is fixed beforehand, and the information selecting section performs filtering by referring to the metadata for selecting the information required by the user.

2. The information display system according to claim 1, wherein the measuring section includes a position measuring instrument configured to measure a position and a direction of the user.

3. The information display system according to claim 2, wherein the position measuring instrument has a GPS function.

4. The information display system according to claim 1, wherein the measuring section includes at least a detector which is configured to detect at least one of an arm movement, a leg movement, a voice, and a sound inside the body of the user.

5. The information display system according to claim 4, wherein a detector which is configured to detect the leg movement includes a pressure sensor which is configured to detect a pressure at at least one location on a planta.

6. The information display system according to claim 5, wherein the pressure sensor is configured to detect a pressure of at least a heel portion.

7. The information display system according to claim 6, wherein the detector which is configured to detect the leg movement makes a judgment of the user to be in a halted state when a pressure fluctuation of the heel portion is not higher than a predetermined first threshold value and when a pressure is not less than a predetermined second threshold value, and makes a judgment of the user to be in a sitting state when the pressure fluctuation of the heel portion is not higher than the predetermined first threshold value and when the pressure is less than the predetermined second threshold value.

8. The information display system according to claim 7, wherein the predetermined second threshold value is set according to a body weight of the user.

9. The information display system according to claim 6, wherein the detector which is configured to detect the leg movement calculates a proportion $\tau$ which is a ratio of a time for which a pressure is exerted on the heel to a time period of one cycle when the pressure fluctuation of the heel portion is higher than the predetermined first threshold value and when the pressure fluctuation is cyclic, and the detector is configured to detect the user to be in a running state when the pressure fluctuation of the heel portion is higher than the predetermined first threshold value and when the proportion $\tau$ is less than a predetermined third threshold value, and the detector is configured to detect the user to be in a walking state when the pressure fluctuation of the heel portion is higher than the predetermined first threshold value and when the proportion $\tau$ is not less than the predetermined third threshold value.

10. The information display system according to claim 4, wherein the detector which is configured to detect the sound inside the body includes a bone conduction microphone.

11. The information display system according to claim 1, wherein the measuring section includes a detector for measuring whether the user is indoors or outdoors.

12. The information display system according to claim 11, wherein the detector includes an ultrasonic sensor, and is configured to detect whether the user is indoors or outdoors by measuring a distance from the detector to a ceiling by using reflection of ultrasonic waves.

13. The information display system according to claim 11, wherein the detector includes an optical sensor including a light emitting and receiving section, and is configured to detect whether the user is indoors or outdoors by measuring a distance from the detector to a ceiling by using reflection of light.

14. The information display system according to one of claims 12 and 13, wherein the detector is configured to detect the user to be indoors under a roof when the distance measured up to the ceiling is in a predetermined range which is set beforehand.

15. The information display system according to claim 11, wherein the detector includes a detector which measures an amount of light in an ultraviolet region.

16. The information display system according to claim 11, wherein the detector includes a pyroelectric sensor.

17. The information display system according to claim 11, wherein the detector includes a microphone.

18. The information display system according to claim 1, wherein the measuring section includes a detector which is configured to detect a pressure of a planta of the user for measuring a movement of a leg.

19. The information display system according to claim 1, wherein the active state identifying section identifies the active state of the user based on measurement data measured by the measuring section and a scheduled action data of the user stored beforehand.

20. The information display system according to claims 1, wherein the measuring section is wearable.

21. The information display system according to claim 1, wherein the information display section is a small size display wearable on a head.

22. The information display system according to claim 1, wherein the measuring section includes a bone conduction microphone and an external sound microphone, and is configured to measure whether the user is in an uttering state or not, and measure whether the user is in a masticating state or not, based on a signal power detected by each microphone.

23. The information display system according to claim 22, wherein the measuring section includes a conversation detector which is configured to detect the user to be in conversation when a proportion of time during which the user is in the uttering state in a predetermined time is not less than a predetermined threshold value.

24. The information display system according to claim 22, wherein the measuring section includes a meal detector which is configured to detect the user to be having a meal when a proportion of time during which the user is in the masticating state in a predetermined time is not less than a predetermined threshold value.

25. The information display system according to claim 1, wherein the information storage section is configured to further store information which is used for selecting the information by the information selecting section.

26. The information display system according to claim 1, wherein the information selecting section is configured to communicate with another computer via a dedicated line or the Internet.

27. An information display system comprising:
a measuring section configured to measure a state of a plurality of parts of a body of a user;
an active state identifying section which identifies an active state of the user based on a measurement result of the measuring section;
an information estimating section which estimates information required by the user based on the active state identified by the active state identifying section;

an information storage section which stores at least the information estimated to be required by the user by the information estimating section;
an information selecting section which selects the information estimated to be required by the user from a plurality of information items stored in the information storage section;
an information display section which displays the information estimated to be required by the user and selected by the information selecting section; and
a schedule storage section which is configured to store at least a schedule of the user,
wherein the active state identifying section identifies the active state of the user by referring to the schedule stored in the schedule storage section.

28. The information display system according to claim 27, further comprising:
a control-calculation section which creates a sub-schedule by estimating at least a travel time based on at least the schedule of the user stored in the schedule storage section.

29. The information display system according to claim 28, wherein the control-calculation section which creates the sub-schedule sets a last hour to start returning home based on a timetable of a last train up to home.

30. An information display system comprising:
a measuring section configured to measure a state of a plurality of parts of a body of a user;
an active state identifying section which identifies an active state of the user based on a measurement result of the measuring section;
an information estimating section which estimates information required by the user based on the active state identified by the active state identifying section;
an information storage section which stores at least the information estimated to be required by the user by the information estimating section;
an information selecting section which selects the information estimated to be required by the user from a plurality of information items stored in the information storage section;
an information display section which displays the information estimated to be required by the user and selected by the information selecting section; and
an external circumstances storage section which is configured to store at least one of a weather forecast information and traffic information,
wherein the information estimating section estimates the information required by the user by referring to at least one of the weather forecast information and the traffic information stored in the external circumstances storage section.

31. An information display system comprising:
a measuring section configured to measure a state of a plurality of parts of a body of a user;
an active state identifying section which identifies an active state of the user based on a measurement result of the measuring section;
an information estimating section which estimates information required by the user based on the active state identified by the active state identifying section;
an information storage section which stores at least the information estimated to be required by the user by the information estimating section;
an information selecting section which selects the information estimated to be required by the user from a plurality of information items stored in the information storage section;
an information display section which displays the information estimated to be required by the user and selected by the information selecting section;
wherein the information storage section includes at least one of an individual database which stores at least one of information such as information of objects of the user's hobby, preference, and interest, an action target, a history database which stores at least one of information such as places the user has visited before and an action history in the past, and data base in which general data is stored.

32. An information display system comprising:
a measuring section configured to measure a state of a plurality of parts of a body of a user;
an active state identifying section which identifies an active state of the user based on a measurement result of the measuring section;
an information estimating section which estimates information required by the user based on the active state identified by the active state identifying section;
an information storage section which stores at least the information estimated to be required by the user by the information estimating section;
an information selecting section which selects the information estimated to be required by the user from a plurality of information items stored in the information storage section;
an information display section which displays the information estimated to be required by the user and selected by the information selecting section; and
a control-calculation section which performs optimization of display information such that detailed character information at a time of displaying the information by the information display section is abbreviated to brief information.

33. An information display system comprising:
a measuring section configured to measure a state of a plurality of parts of a body of a user;
an active state identifying section which identifies an active state of the user based on a measurement result of the measuring section;
an information estimating section which estimates information required by the user based on the active state identified by the active state identifying section;
an information storage section which stores at least the information estimated to be required by the user by the information estimating section;
an information selecting section which selects the information estimated to be required by the user from a plurality of information items stored in the information storage section;
an information display section which displays the information estimated to be required by the user and selected by the information selecting section; and
a schedule storage section which is configured to store at least a schedule of the user,
wherein the measuring section includes:
a position measuring section which is configured to measure a position and a direction of the user, and
an indoor-outdoor detector for measuring whether the user is indoors or outdoors, and
wherein the active state identifying section identifies the user to be indoors near a position measured immediately before by the position measuring section when the indoor-outdoor detector detects the user to be indoors even when the position measuring section is in an environment where it is not possible to measure the position, and thereafter, the active state identifying section identifies the user to be at a position according to at least the schedule of the user which is stored in the schedule storage section till the position measuring section once again enters an environment where it is possible to measure the position.

* * * * *